US008426473B2

(12) United States Patent
Ebdrup

(10) Patent No.: US 8,426,473 B2
(45) Date of Patent: *Apr. 23, 2013

(54) PHENOXY ACETIC ACIDS AS PPAR DELTA ACTIVATORS

(75) Inventor: Soren Ebdrup, Roskilde (DK)

(73) Assignee: High Point Pharnaceuticals, LLC, High Point, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/466,191

(22) Filed: May 8, 2012

(65) Prior Publication Data

US 2012/0232080 A1    Sep. 13, 2012

Related U.S. Application Data

(60) Continuation of application No. 13/080,425, filed on Apr. 5, 2011, now Pat. No. 8,217,086, which is a division of application No. 11/917,811, filed as application No. PCT/EP2006/063703 on Jun. 29, 2006, now Pat. No. 7,943,669.

(30) Foreign Application Priority Data

Jun. 30, 2005 (EP) ...................... 05105937
Dec. 22, 2005 (EP) ...................... 05112755

(51) Int. Cl.
*A61K 31/75* (2006.01)
*A61K 31/15* (2006.01)

(52) U.S. Cl.
USPC .......................... 514/717; 514/764

(58) Field of Classification Search .................. 514/717, 514/764
See application file for complete search history.

(56) References Cited

U.S. PATENT DOCUMENTS

| | | | |
|---|---|---|---|
| 4,920,132 A | 4/1990 | Huang et al. | |
| 5,324,743 A | 6/1994 | Dillard et al. | |
| 5,538,768 A | 7/1996 | Marden et al. | |
| 6,448,293 B1 | 9/2002 | Andrews et al. | |
| 6,525,094 B1 | 2/2003 | Zhang et al. | |
| 6,630,504 B2 | 10/2003 | Andrews et al. | |
| 6,869,975 B2 | 3/2005 | Abe et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,244,763 B2 | 7/2007 | Bratton et al. | |
| 7,816,385 B2 | 10/2010 | Sauerberg et al. | |
| 7,943,612 B2 | 5/2011 | Sauerberg | |
| 7,968,723 B2 | 6/2011 | Havranek et al. | |
| 2004/0192743 A1 | 9/2004 | Mjalli et al. | |
| 2004/0209936 A1 | 10/2004 | Bratton et al. | |
| 2005/0113440 A1 | 5/2005 | Auerbach et al. | |
| 2007/0082907 A1 | 4/2007 | Canada et al. | |

FOREIGN PATENT DOCUMENTS

| | | |
|---|---|---|
| GB | 2279659 | 11/1995 |
| JP | 2003-171275 | 6/2003 |
| WO | WO 01/25226 | 8/1997 |
| WO | WO 97/27847 | 8/1997 |
| WO | WO 97/27857 | 8/1997 |
| WO | WO 97/28115 | 8/1997 |
| WO | WO 97/28137 | 8/1997 |
| WO | WO 97/28149 | 8/1997 |
| WO | WO 98/27974 | 7/1998 |
| WO | WO 99/04815 | 2/1999 |
| WO | WO 99/20275 | 4/1999 |
| WO | WO 01/00603 | 1/2001 |
| WO | WO 01/25181 | 4/2001 |
| WO | WO 01/34137 | 5/2001 |
| WO | WO 01/34200 | 5/2001 |
| WO | WO 01/79197 | 5/2001 |
| WO | WO 01/60807 | 8/2001 |
| WO | WO 01/66098 | 9/2001 |
| WO | WO 02/014291 | 2/2002 |
| WO | WO 02/28434 | 4/2002 |
| WO | WO 02/46154 | 6/2002 |
| WO | WO 02/50048 | 6/2002 |
| WO | WO 02/053547 | 7/2002 |
| WO | WO 02/059098 | 8/2002 |
| WO | WO 02/062774 | 8/2002 |
| WO | WO 02/070011 | 9/2002 |
| WO | WO 02/076957 | 10/2002 |
| WO | WO 02/079162 | 10/2002 |
| WO | WO 02/080899 | 10/2002 |
| WO | WO 02/098840 | 12/2002 |
| WO | WO 02/100812 | 12/2002 |
| WO | WO 03/002081 | 1/2003 |
| WO | WO 03/016265 | 2/2003 |
| WO | WO 03/016291 | 2/2003 |
| WO | WO 03/024395 | 3/2003 |
| WO | WO 03/033453 | 4/2003 |
| WO | WO 03/033493 | 4/2003 |
| WO | WO 03/035603 | 5/2003 |
| WO | WO 03/072100 | 9/2003 |
| WO | WO 03/074050 | 9/2003 |
| WO | WO 03/074051 | 9/2003 |
| WO | WO 03/074052 | 9/2003 |
| WO | WO 03/074495 | 9/2003 |
| WO | WO 03/084916 | 10/2003 |
| WO | WO 03/097607 | 11/2003 |
| WO | WO 2004/000315 | 12/2003 |
| WO | WO 2004/000762 | 12/2003 |
| WO | WO 2004/005253 | 1/2004 |
| WO | WO 2004/007439 | 1/2004 |

(Continued)

OTHER PUBLICATIONS

Reusch JEB. Diabetes, microvascular complications, and cardiovascular complications: what is it about glucose? J Clin Invest. Oct. 1, 2003; 112(7): 986-988.*

(Continued)

*Primary Examiner* — Paul Zarek
(74) *Attorney, Agent, or Firm* — Samuel B. Rollins

(57) ABSTRACT

The present invention describes phenoxy-acetic acids and pharmaceutical compositions containing the same and methods of using the same. The phenoxy-acetic acids are activators of PPAR-δ and should be useful for treating conditions mediated by the same.

4 Claims, No Drawings

FOREIGN PATENT DOCUMENTS

| | | |
|---|---|---|
| WO | WO 2004/056740 | 7/2004 |
| WO | WO 2004/060871 | 7/2004 |
| WO | WO 2004/063165 | 7/2004 |
| WO | WO 2004/063166 | 7/2004 |
| WO | WO 2004/071447 | 8/2004 |
| WO | WO 2004/073606 | 9/2004 |
| WO | WO 2004/080943 | 9/2004 |
| WO | WO 2004/080947 | 9/2004 |
| WO | WO 2004/092117 | 10/2004 |
| WO | WO 2004/093879 | 11/2004 |
| WO | WO 2004/099170 | 11/2004 |
| WO | WO 2005/054176 | 6/2005 |
| WO | WO 2005/097098 | 10/2005 |
| WO | WO 2005/097762 | 10/2005 |
| WO | WO 2005/097763 | 10/2005 |
| WO | WO 2005/105726 | 11/2005 |
| WO | WO 2005/113506 | 12/2005 |
| WO | WO 2007/101864 | 9/2007 |

OTHER PUBLICATIONS

Berger, J. and Wagner, J., "Physiological and Therapeutic Roles of Peroxisome Proliferator-Activated Receptors," Diabetes Technology & Therapeutics, vol. 4(2), pp. 163-174 (2002).
Berger, Joel et al., "Novel Peroxisome Proliferator-activated Receptor (PPAR) gamma and PPAR delta Ligands Produce Distinct Biological Effects" Journal of Biological Chemistry, vol. 274, No. 10, pp. 6718-6725 (1999).
Chilonczyk et al., "Hypolipidaemic and antiplatelet agents", 2001, Expert Opin. Ther. Patents, 11 (8), pp. 1301-1327.
Colagiuri et al., American Journal of Public Health, Sep. 2006, vol. 96, No. 9, pp. 1562-1569.
Curtis et al., The Journal of the American Board of Family Practice, vol. 18, pp. 37-43, (2005).
Dressel, U. et al., Mol Endocrinol, 2003, vol. 17, Part 12, pp. 2477-2493.
Epple et al., Bioorganic & Medicinal Chemistry Letters 2006, 16, 4376-4380.
European Search Report for European Patent Application No. 05112755.3 dated May 10, 2006.
Everett, L., et al., "The role of hepatic peroxisome proliferator-activated receptors (PPARs) in health and disease," Liver, vol. 20, pp. 191-199 (2000).
Fruchart, J., "PPAR and Cardiovascular Risk: Overview," J. Cardiovasc. Risk, vol. 8(4), pp. 185-186 (Aug. 2001).
Golub et al., Science, vol. 286, Oct. 15, 1999, pp. 531-537.
Gross et al., Best Practice & Research Clinical Endocrinology & Metabolism 2007, 21, 687-710.
Havranek et al., "E/Z Isomerization of 3,3-disubstituted allylic thioethers" Tetrahedron Lett., vol. 48, pp. 6970-6973 (2007).
Hoist, D. et al., Biochem Biophys Acta, 2003, vol. 1633, pp. 43-50.
Hussain et al., Diabetes Research and Clinical Practice 2007, 76, 317-326.
International Preliminary Report on Patentability for PCT/EP06/063703 dated Jan. 17, 2008.
International Search Report for PCT/EP06/063703 dated Apr. 10, 2006.
Jones, B., "Peroxisome Proliferative-Activated Receptor (PPAR) Modulators: Diabetes and Beyond," Medicinal Research Reviews, vol. 21(6), pp. 540-552 (Nov. 2001).
Kaplan, F., et al., "PPARs, Insulin Resistance and Type 2 Diabetes," J. Cardiovasc. Risk, vol. 8(4), pp. 211-217 (Aug. 2001).
Kersten, S., et al., "Roles of PPARs in health and disease," Nature, vol. 405, pp. 421-424 (May 2000).
Landreth et al., Neurobiology of Aging, 2001, 22, 937-944.
Lee, C.H. et al., "PPAR-delta regulates glucose metabolism and insulin sensitivity", Proceedings of the National Academy of Sciences of the USA, 2006, vol. 103, No. 9, pp. 3444-3449.
Lee, C-H et al., Science, 2003, vol. 32, pp. 453-457.
Leibowitz, Mark D. et al., "Activation of PPAR delta alters lipid metabolism in db/db mice" FEBS Letters, 473:333-336 (2000).
Liu, K., et al., "Identification of a Series of PPAR gamma/delta Dual Agonists via Solid-Phase Parallel Synthesis," Bioorg. Med. Chem. Lett., vol. 11, pp. 2959-2962 (Nov. 2001).
Luquet, S. et al., Faseb J, 2003, vol. 17, Part 13, pp. 209-226.
Michalik, L., and Wahli, W., "Peroxisome proliferator-activated receptors: three isotypes for a multitude of functions," Curr. Opin. Biotechnology, vol. 10, pp. 564-570 (1999).
Miller, A., and Etgen, G., "Novel peroxisome proliferator-activated receptor ligands for type 2 diabetes and the metabolic syndrome," Expert Opin. Investig. Drugs, vol. 12(9), pp. 1489-1500 (2003).
Mital, A., "PPARs: Nuclear Receptors for Antidiabetics," CRIPS, vol. 3(1), pp. 5-8 (Jan.-Mar. 2002).
Muoio, Deborah M. "Fatty Acid Homestasis and Induction of Lipid Regulatory Genes in Skeletal Muscles of Peroxisome Proliferator-activated Receptor (PPAR) Knock-out Mice" Journal of Biological Chemistry, vol. 277, No. 29, Issue of Jul. 19, pp. 26089-26097, 2002.
Notice of Allowance for U.S. Appl. No. 11/579,712, dated Dec. 10, 2010.
Oliver, William R. Jr. et al., "A Selective peroxisome proliferator-activated receptor delta agonist promotes reverse cheolesterol transport" Proceedings of the National Academy of Sciences, vol. 98, No. 9, pp. 5306-5311, Apr. 24, 2001.
Park, Diabetes Research and Clinical Practice 66S (2004), S33-S35.
Pending Claims for U.S. Appl. No. 12/958,237, dated Dec. 1, 2010.
Pending Claims for U.S. Appl. No. 10/777,488 dated Nov. 5, 2008.
Peters et al., Biochimica et Biophysica Acta 2009, 1796, 230-241.
Sauerberg et al., Identification and Synthesis of a Novel Selective Partial PPAR-delta Agonist with Full Efficacy on Lipid Metabolism In Vitro and In Vivo J. Med. Chem., vol. 50, pp. 1495-1503 (2007).
Schiffrin et al., "Peroxisome Proliferator-Activated Receptors: Vascular and Cardiac Effects in Hypertension", Hypertension, 2003, 42; pp. 664-668.
Tanaka et al., "Activation of peroxisome proliferator-activated receptor delta induces fatty acid beta-oxidation in skeletal muscle and attenuates metabolic syndrome" PNAS, vol. 100(26), pp. 15924-15929 (2003).
Tanaka, T. et al., PNAS, 2003, vol. 100, Part 26, pp. 15924-15929.
Tiikkainen, M., et al., "Effects of Rosiglitazone and Metformin on Liver Fat Content, Hepatic Insulin Resistance, Insulin Clearance, and Gene Expression in Adipose Tissue in Patients with Type 2 Diabetes," Diabetes, vol. 53, pp. 2169-2176 (Aug. 2004)
Torra, I., et al., "Peroxisome proliferator-activated receptors: from transcriptional control to clinical practice," Curr. Opin. Lipidol., vol. 12, p. 245-254 (2001)
Vamecq, J. and Latruffe, N., "Medical significance of peroxisome proliferator-activated receptors," The Lancet, vol. 354, pp. 141-148 (Jul. 10, 1999)
Wahli, W., "Peroxisome Proliferator-Activated Receptors (PPARs): from metabolic control to epidermal wound healing," Swiss Med. Weekly, vol. 132, pp. 83-91 (2002)
Wang et al., "Peroxisome-proliferator-activated receptor delta activates fat metabolism to prevent obesity" Cell, vol. 113, pp. 159-170 (2003).
Wilson et al., "The PPARs: From Orphan Receptors to Drug Discovery" J. Med. Chem., vol. 43(4), pp. 527-550 (2000).

* cited by examiner

PHENOXY ACETIC ACIDS AS PPAR DELTA ACTIVATORS

CROSS-REFERENCE TO RELATED APPLICATIONS

The present application is a continuation application of U.S. patent application Ser. No. 13/080,425, which is a divisional application of U.S. patent application Ser. No. 11/917,811, which is the United States national stage application, under 35 U.S.C. §371, of PCT Application No. PCT/EP2006/063703, filed Jun. 29, 2006, which in turn claims priority to European Patent Application Nos. 05105937.6, filed Jun. 30, 2005, and 05112755.3, filed Dec. 22, 2005. Each of the foregoing applications is incorporated by reference as though fully set forth herein in its entirety.

FIELD OF THE INVENTION

The present invention relates to novel phenoxy-acetic acids, pharmaceuticals comprising the same, and methods of using the same. The phenoxy-acetic acids are activators of peroxisome proliferator-activated receptors (PPAR)-δ.

BACKGROUND OF THE INVENTION

Coronary artery disease (CAD) is the major cause of death in Type 2 diabetic and metabolic syndrome patients (i.e., patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities, although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content.

PPAR-δ activation was initially reported not to be involved in modulation of glucose or triglyceride levels. (Berger et al., J. Biol. Chem. 1999, 274, 6718-6725). Later it was shown that PPAR-δ activation leads to increased levels of HDL cholesterol in db/db mice (Leibowitz et al., FEBS letters 2000, 473, 333-336). Further, a PPAR-δ agonist when dosed to insulin-resistant middle-aged obese rhesus monkeys caused a dramatic dose-dependent rise in serum HDL cholesterol while lowering the levels of small dense LDL, fasting triglycerides and fasting insulin (Oliver et al., PNAS 2001, 98, 5306-5311). The same paper also showed that PPAR-δ activation increased the reverse cholesterol transporter ATP-binding cassette A1 and induced apolipoprotein A1-specific cholesterol efflux. The involvement of PPAR-δ in fatty acid oxidation in muscles was further substantiated in PPAR-α knockout mice. Muoio et al. (J. Biol. Chem. 2002, 277, 26089-26097) showed that the high levels of PPAR-δ in skeletal muscle can compensate for deficiency in PPAR-α. In addition to the effects on cholesterol homeostasis, PPARδ treatment was observed to lower plasma glucose and insulin and improve insulin sensitivity in diabetic ob/ob and db/db mice and high fat diet induced insulin resistant mice (PNAS 2003, 100, 15924-15929; PNAS 2006, 103, 3444-3449). Taken together these observations suggest that PPAR-δ activation is useful in the treatment and prevention of Type 2 diabetes, cardiovascular diseases and conditions including atherosclerosis, hypertriglyceridemia, and mixed dyslipidaemia (WO 01/00603).

A number of PPAR-δ compounds have been reported to be useful in the treatment of hyperglycemia, hyperlipidemia and hypercholesterolemia (WO 02/59098, WO 01/603, WO 01/25181, WO 02/14291, WO 01/79197, WO 99/4815, WO 97/28149, WO 98/27974, WO 97/28115, WO 97/27857, WO 97/28137, and WO 97/27847). WO 2004093879, WO 2004092117, WO 2004080947, WO 2004080943, WO 2004073606, WO 2004063166, WO 2004063165, WO 2003072100, WO 2004060871, WO 2004005253, WO 2003097607, WO 2003035603, WO 2004000315, WO 2004000762, WO 2003074495, WO 2002070011, WO 2003084916, US 20040209936, WO 2003074050, WO 2003074051, WO 2003074052, JP 2003171275, WO 2003033493, WO 2003016291, WO 2002076957, WO 2002046154, WO 2002014291, WO 2001079197, WO 2003024395, WO 2002059098, WO 2002062774, WO 2002050048, WO 2002028434, WO 2001000603, WO 2001060807, WO 9728149, WO 2001034200, WO 9904815, WO 200125226, WO 2005097098; WO 2005097762; WO 2005097763.

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia. This indicates that research for compounds displaying various degree of PPAR-δ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e., impaired glucose tolerance, insulin resistance, hypertrigyceridaemia and/or obesity), cardiovascular diseases (including atherosclerosis) and hypercholesteremia.

SUMMARY OF THE INVENTION

In an aspect, the present invention provides novel phenoxy-acetic acids or pharmaceutically acceptable salts thereof that are useful as PPAR-δ activators.

In another aspect, the present invention provides novel pharmaceutical compositions comprising a pharmaceutically acceptable carrier and a therapeutically effective amount of at least one of the compounds of the present invention or a pharmaceutically acceptable salt thereof.

In another aspect, the present invention provides a novel method of treating type 2 diabetes comprising administering to a patient in need thereof a therapeutically effective amount of at least one compound of the present invention or a pharmaceutically acceptable salt thereof.

In another aspect, the present invention provides a novel method of treating a disease comprising administering to a patient in need thereof a therapeutically effective amount of at least one compound of the present invention or a pharmaceutically acceptable salt thereof, wherein the disease is selected from dyslipidemia, syndrome X (including the metabolic syndrome, e.g., hypertension, impaired glucose tolerance (IGT), insulin resistance, hypertrigyceridaemia, and obesity), cardiovascular diseases (e.g., atherosclerosis, coronary artery disease, and myocardial ischemia), hyperglycemia, hyperlipidemia, and hypercholesterolemia.

In another aspect, the present invention provides a novel method of treating a disease comprising administering to a patient in need thereof a therapeutically effective amount of at least one compound of the present invention or a pharmaceutically acceptable salt thereof, wherein the disease is selected from non-insulin requiring Type 2 diabetes to insulin requiring Type 2 diabetes, decreasing apoptosis in mammalian cells (e.g., beta cells of Islets of Langerhans), renal diseases (e.g., glomerulonephritis, glomerulosclerosis, nephrotic syndrome, and hypertensive nephrosclerosis), improving cognitive functions in dementia, treating diabetic complications, psoriasis, polycystic ovarian syndrome (PCOS), prevention and treatment of bone loss (e.g., osteoporosis), and lowering the bio-markers of atherosclerosis (e.g., c-reactive protein (CRP), TNF-α, and IL-6).

In another aspect, the present invention provides novel compounds for use in therapy.

In another aspect, the present invention provides the use of novel compounds for the manufacture of a medicament for the treatment of type 2 diabetes.

These and other objects, which will become apparent during the following detailed description, have been achieved by the inventors' discovery that compounds of formula I:

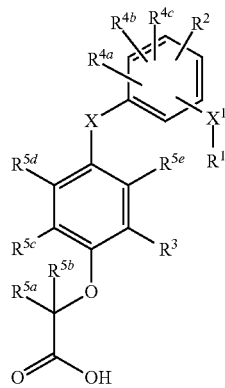

or pharmaceutically acceptable salts thereof, are PPAR-δ activators.

DESCRIPTION OF THE INVENTION

In a first embodiment, the present invention provides a novel compound of formula I:

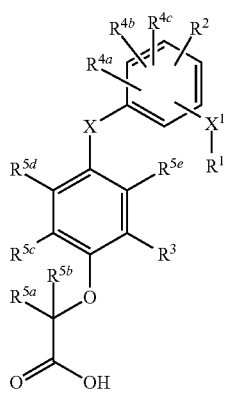

or a pharmaceutically acceptable salt thereof, wherein:
X is selected from O, S, $OCH_2$, and $SCH_2$;
$X^1$ is O or S;

$R^1$ is selected from H, $C_{1-8}$ alkyl, $C_{2-8}$ alkenyl, aryl, heteroaryl, $C_{3-10}$ cycloalkyl, and a heterocyclyl, wherein each $R^1$ group is substituted with 0-4 $R^{1a}$;

$R^{1a}$, at each occurrence, is selected from S substituted with 0-1 $R^{1b}$, O substituted with 0-1 $R^{1b}$, halogen, $NH_2$ substituted with 0-2 $R^{1b}$, —CN, $NO_2$, $C_{1-6}$ alkyl substituted with 0-3 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, heteroaryl substituted with 0-2 $R^{1b}$, $C_{3-10}$ cycloalkyl substituted with 0-2 $R^{1b}$, and heterocycle substituted with 0-2 $R^{1b}$;

$R^{1b}$, at each occurrence, is selected from S substituted with 0-1 $R^{1c}$, O substituted with 0-1 $R^{1c}$, halogen, methanesulfonyl, $NH_2$ substituted with 0-2 $R^{1c}$, —CN, $NO_2$, $C_{1-6}$ alkyl substituted with 0-3 $R^{1c}$, $C_{2-6}$ alkenyl substituted with 0-2 $R^{1c}$, aryl substituted with 0-2 $R^{1c}$, heteroaryl substituted with 0-2 $R^{1c}$, $C_{3-10}$ cycloalkyl substituted with 0-2 $R^{1c}$, and a heterocycle substituted with 0-2 $R^{1c}$;

$R^{1c}$, at each occurrence, is selected from S substituted with 0-1 $R^{1d}$, O substituted with 0-1 $R^{1d}$, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, heteroaryl substituted with 0-2 $R^{1d}$, $C_{3-10}$ cycloalkyl substituted with 0-2 $R^{1d}$, and a heterocycle substituted with 0-2 $R^{1d}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH=CH—$R^{2a}$, aryl substituted with 0-3 $R^{2a}$, and heteroaryl substituted with 0-3 $R^{2a}$;

$R^{2a}$, at each occurrence, is selected from S substituted with 0-1 $R^{2b}$, O substituted with 0-1 $R^{2b}$, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, heteroaryl substituted with 0-2 $R^{2b}$, $C_{3-10}$ cycloalkyl substituted with 0-2 $R^{2b}$, and a heterocycle substituted with 0-2;

$R^{2b}$, at each occurrence, is selected from S substituted with 0-1 $R^{2c}$, O substituted with 0-1 $R^{2c}$, halogen, methanesulfonyl, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, heteroaryl substituted with 0-2 $R^{2c}$, $C_{3-10}$ cycloalkyl substituted with 0-2 $R^{2c}$, and a heterocycle substituted with 0-2 $R^{2c}$;

$R^{2c}$, at each occurrence, is selected from S substituted with 0-1 $R^{2d}$, O substituted with 0-1 $R^{2d}$, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, heteroaryl substituted with 0-2 $R^{2d}$, $C_{3-10}$ cycloalkyl substituted with 0-2 $R^{2d}$, and a heterocycle substituted with 0-2 $R^{2d}$ $R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH$—$C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and $N(C_{1-4}$ alkyl$)_2$;

$R^{4b}$, at each occurrence, is selected from H, halogen, and $C_{1-6}$ alkyl substituted with 0-2 $R^{4e}$;

$R^{4e}$, at each occurrence, is selected from OH, O, halogen, $NH_2$, NH—$C_{1-4}$ alkyl, and $N(C_{1-4}$ alkyl$)_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and $N(C_{1-4}$ alkyl$)_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

In another embodiment, the present invention provides a novel compound of formula I or a pharmaceutically acceptable salt thereof, wherein:

X is selected from O, S, $OCH_2$, and $SCH_2$;

$X^1$ is O or S;

$R^1$ is selected from H, $C_{1-8}$ alkyl, $C_{2-8}$ alkenyl, aryl, 5-10 membered heteroaryl consisting of carbon atoms and 1-4 heteroatoms selected from O, N, and $S(O)_{0-2}$, $C_{3-10}$ cycloalkyl, and a 3-8 membered heterocycle consisting of carbon atoms and 1-3 heteroatoms selected from O, N, and $S(O)_{0-2}$, wherein each $R^1$ group is substituted with 0-4 $R^{1a}$;

$R^{1a}$, at each occurrence, is selected from OH substituted with 0-1 $R^{1b}$, SH substituted with 0-1 $R^{1b}$, S, O, halogen, $NH_2$ substituted with 0-2 $R^{1b}$, —CN, $NO_2$, $C_{1-6}$ alkyl substituted with 0-3 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-3 heteroatoms selected from O, N, and $S(O)_{0-2}$;

$R^{1b}$, at each occurrence, is selected from OH substituted with 0-1 $R^{1c}$, SH substituted with 0-1 $R^{1c}$, S, O, halogen, methanesulfonyl, $NH_2$ substituted with 0-2 $R^{1c}$, —CN, $NO_2$, $C_{1-6}$ alkyl substituted with 0-3 $R^{1c}$, $C_{2-6}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-10}$ cycloalkyl substituted with 0-2 $R^{1c}$, and a 3-8 membered heterocycle substituted with 0-2 $R^{1c}$ and consisting of carbon atoms and 1-3 heteroatoms selected from O, N, and $S(O)_{0-2}$;

$R^{1c}$, at each occurrence, is selected from OH substituted with 0-1 $R^{1d}$, SH substituted with 0-1 $R^{1d}$, S, O, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-10}$ cycloalkyl substituted with 0-2 $R^{1d}$, and a 3-8 membered heterocycle substituted with 0-2 $R^{1d}$ and consisting of carbon atoms and 1-3 heteroatoms selected from O, N, and $S(O)_{0-2}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH=CH—$R^{2a}$ substituted with 0-2 $R^{2a}$, aryl substituted with 0-3 $R^{2a}$, and 5-10 membered heteroaryl substituted with 0-3 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, S, O, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-10}$ cycloalkyl substituted with 0-2 $R^{2b}$, and a 3-8 membered heterocycle substituted with 0-2 $R^{2b}$ and consisting of carbon atoms and 1-3 heteroatoms selected from O, N, and $S(O)_{0-2}$;

$R^{2b}$, at each occurrence, is selected from OH substituted with 0-1 $R^{2c}$, SH substituted with 0-1 $R^{2c}$, S, O substituted with 0-1 $R^{2c}$, halogen, methanesulfonyl, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-10}$ cycloalkyl substituted with 0-2 $R^{2c}$, and a 3-8 membered heterocycle substituted with 0-2 $R^{2c}$ and consisting of carbon atoms and 1-3 heteroatoms selected from O, N, and $S(O)_{0-2}$;

$R^{2c}$, at each occurrence, is selected from OH substituted with 0-1 $R^{2d}$, SH substituted with 0-1 $R^{2d}$, S, O, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, 5-10 membered heteroaryl substituted with 0-2 $R^{2d}$ and consisting of carbon atoms and 1-4 heteroatoms selected from O, N, and $S(O)_{0-2}$, $C_{3-10}$ cycloalkyl substituted with 0-2 $R^{2d}$, and a 3-8 membered heterocycle substituted with 0-2 $R^{2d}$ and consisting of carbon atoms and 1-3 heteroatoms selected from O, N, and $S(O)_{0-2}$;

$R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH$—$C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and $N(C_{1-4}$ alkyl$)_2$;

$R^{4b}$, at each occurrence, is selected from H, halogen, and $C_{1-6}$ alkyl substituted with 0-2 $R^{4e}$ $R^{4e}$, at each occurrence, is selected from OH, O, halogen, $NH_2$, NH—$C_{1-4}$ alkyl, and $N(C_{1-4}$ alkyl$)_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and $N(C_{1-4}$ alkyl$)_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

In another embodiment, the present invention provides a novel compound of formula I or a pharmaceutically acceptable salt thereof, wherein:

X is selected from O, S, $OCH_2$, and $SCH_2$;

$X^1$ is O or S;

$R^1$ is selected from H, $C_{1-8}$ alkyl, $C_{2-8}$ alkenyl, aryl, 5-10 membered heteroaryl consisting of carbon atoms and 1-4 heteroatoms selected from O, N, and $S(O)_{0-2}$, $C_{3-10}$ cycloalkyl, and a 3-8 membered heterocycle consisting of carbon atoms and 1-3 heteroatoms selected from O, N, and $S(O)_{0-2}$, wherein each $R^1$ group is substituted with 0-4 $R^{1a}$;

$R^{1a}$, at each occurrence, is selected from OH substituted with 0-1 $R^{1b}$, SH substituted with 0-1 $R^{1b}$, S, O, halogen, $NH_2$ substituted with 0-2 $R^{1b}$, —CN, $NO_2$, $C_{1-6}$ alkyl substituted with 0-2 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-3 heteroatoms selected from O, N, and $S(O)_{0-2}$;

$R^{1b}$, at each occurrence, is selected from OH substituted with 0-1 $R^{1c}$, SH substituted with 0-1 $R^{1c}$, S, O, halogen, $NH_2$ substituted with 0-2 $R^{1c}$, —CN, $NO_2$, $C_{1-6}$ alkyl substituted with 0-2 $R^{1c}$, $C_{2-6}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-10}$ cycloalkyl substituted with 0-2 $R^{1c}$, and a 3-8 membered heterocycle substituted with 0-2 $R^{1c}$ and consisting of carbon atoms and 1-3 heteroatoms selected from O, N, and $S(O)_{0-2}$;

$R^{1c}$, at each occurrence, is selected from OH substituted with 0-1 $R^{1d}$, SH substituted with 0-1 $R^{1d}$, S, O, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-10}$ cycloalkyl substituted with 0-2 $R^{1d}$, and a 3-8 membered heterocycle substituted with 0-2 $R^{1d}$ and consisting of carbon atoms and 1-3 heteroatoms selected from O, N, and $S(O)_{0-2}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH=CH—$R^{2a}$ substituted with 0-2 $R^{2a}$, aryl substituted with 0-3 $R^{2a}$, and 5-10 membered heteroaryl substituted with 0-3 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, S, O, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-10}$ cycloalkyl substituted with 0-2 $R^{2b}$, and a 3-8 membered heterocycle substituted with 0-2 $R^{2b}$ and consisting of carbon atoms and 1-3 heteroatoms selected from O, N, and $S(O)_{0-2}$;

$R^{2b}$, at each occurrence, is selected from OH substituted with 0-1 $R^{2c}$, SH substituted with 0-1 $R^{2c}$, S, O, halogen, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-10}$ cycloalkyl substituted with 0-2 $R^{2c}$, and a 3-8 membered heterocycle substituted with 0-2 $R^{2c}$ and consisting of carbon atoms and 1-3 heteroatoms selected from O, N, and $S(O)_{0-2}$;

$R^{2c}$, at each occurrence, is selected from OH substituted with 0-1 $R^{2d}$, SH substituted with 0-1 $R^{2d}$, S, O, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, 5-10 membered heteroaryl substituted with 0-2 $R^{2d}$ and consisting of carbon atoms and 1-4 heteroatoms selected from O, N, and $S(O)_{0-2}$, $C_{3-10}$ cycloalkyl substituted with 0-2 $R^{2d}$, and a 3-8 membered heterocycle substituted with 0-2 $R^{2d}$ and consisting of carbon atoms and 1-3 heteroatoms selected from O, N, and $S(O)_{0-2}$;

$R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH$—$C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$ $R^{4d}$, at each occurrence, is selected from OH, O, halogen, $NH_2$, NH—$C_{1-4}$ alkyl, and $N(C_{1-4}$ alkyl$)_2$;

$R^{4b}$, at each occurrence, is selected from H, halogen, and $C_{1-6}$ alkyl substituted with 0-2 $R^{4e}$ $R^{4e}$, at each occurrence, is selected from OH, O, halogen, $NH_2$, NH—$C_{1-4}$ alkyl, and $N(C_{1-4}$ alkyl$)_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and $N(C_{1-4}$ alkyl$)_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

In a embodiment, the present invention provides a novel compound of formula Ia:

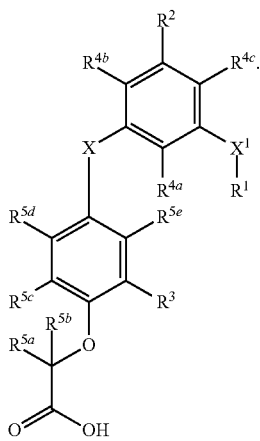

Ia or a pharmaceutically acceptable salt thereof.

In another embodiment, the present invention provides a novel compound of formula II:

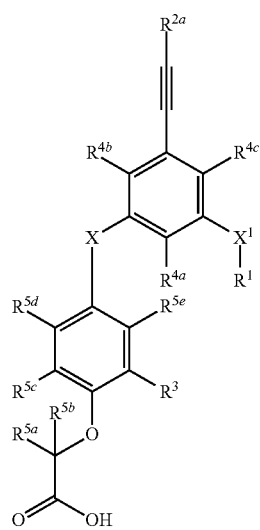

II or a pharmaceutically acceptable salt thereof, wherein:

$R^1$ is H, $C_{1-8}$ alkyl, heteroaryl, and $C_{3-10}$ cycloalkyl, wherein each $R^1$ group is substituted with 0-4 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$ $R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$ and, $C_{3-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, methanesulfonyl, $C_{1-4}$ alkyl substituted with 0-2 $R^{2c}$, $C_{2-4}$ alkenyl substituted with 0-2 $R^{2c}$, aryl substituted with 0-2 $R^{2c}$, heteroaryl substituted with 0-2 $R^{2c}$, $C_{3-6}$ cycloalkyl substituted with 0-2 $R^{2c}$, and a heterocycle substituted with 0-2 $R^{2c}$ $R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and heteroaryl substituted with 0-2 $R^{2d}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

In another embodiment, the present invention provides a novel compound of formula II or a pharmaceutically acceptable salt thereof, wherein:

$R^1$ is H, $C_{1-8}$ alkyl, 5-10 membered heteroaryl consisting of carbon atoms and 1-4 heteroatoms selected from O, N, and $S(O)_{0-2}$, and $C_{3-10}$ cycloalkyl, wherein each $R^1$ group is substituted with 0-4 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, methanesulfonyl, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2c}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and, $R^{5e}$, at each occurrence, is selected from H, Cl, F, and $CH_3$.

In another embodiment, the present invention provides a novel compound of formula II or a pharmaceutically acceptable salt thereof, wherein:

$R^1$ is H or $C_{1-4}$ alkyl substituted with 1-4 $R^{1a}$;

$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2e}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and, $R^{5e}$, at each occurrence, is selected from H, Cl, F, and $CH_3$.

In another embodiment, the present invention provides a novel compound of formula IIa:

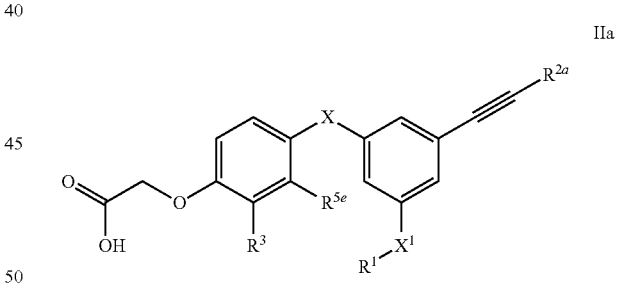

IIa or a pharmaceutically acceptable salt thereof, wherein:

$R^1$ is H, $C_{1-6}$ alkyl, aryl, heteroaryl, and $C_{3-10}$ cycloalkyl, wherein each $R^1$ group is substituted with 0-1 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, heteroaryl substituted with 0-2 $R^{1b}$ and, $C_{5-6}$ cycloalkyl substituted with 0-2 $R^{1b}$, and a heterocycle substituted with 0-2 $R^{1b}$ and;

$R^{1b}$, at each occurrence, is selected from OH, SH, Cl, F, $NH_2$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{5-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{5-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH substituted with 0-1 $R^{2c}$, SH, Cl, F, $NH_2$, —CN, $NO_2$, methanesulfonyl, $C_{1-4}$ alkyl, $C_{2-4}$ alkenyl, aryl, heteroaryl, $C_{5-6}$ cycloalkyl, and a heterocycle;

$R^{2c}$, at each occurrence, is $C_{1-4}$ alkyl;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

In another embodiment, the present invention provides a novel compound of formula IIa or a pharmaceutically acceptable salt thereof, wherein:

$R^1$ is H, $C_{1-6}$ alkyl, aryl, 5-6 membered heteroaryl consisting of carbon atoms and 1-4 heteroatoms selected from O, N, and $S(O)_{0-2}$, and $C_{3-10}$ cycloalkyl, wherein each $R^1$ group is substituted with 0-1 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{5-6}$ cycloalkyl substituted with 0-2 $R^{1d}$, and a 5-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O, N, and $S(O)_{0-2}$;

$R^{2b}$, at each occurrence, is selected from OH substituted with 0-1 $R^{2c}$, SH, Cl, F, $NH_2$, —CN, $NO_2$, methanesulfonyl, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$;

$R^{2c}$, at each occurrence, is $C_{1-4}$ alkyl;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

In another embodiment, the present invention provides a novel compound of formula IIa or a pharmaceutically acceptable salt thereof, wherein:

$R^1$ is H or $C_{1-4}$ alkyl substituted with 1 $R^{1a}$;

$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{5-6}$ cycloalkyl substituted with 0-2 $R^{1d}$, and a 5-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O, N, and $S(O)_{0-2}$;

$R^{2b}$, at each occurrence, is selected from OH, SH, Cl, F, $NH_2$, —CN, $NO_2$, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

In another embodiment, the present invention provides a novel compound of formula IIa or a pharmaceutically acceptable salt thereof, wherein:

$R^1$ is H, $C_{1-6}$ alkyl, aryl, heteroaryl, $C_{3-10}$ cycloalkyl, wherein each $R^1$ group is substituted with 0-1 $R^{1a}$;

$R^{1a}$, at each occurrence, is selected from $C_{1-4}$ alkyl substituted with 0-3 $R^{1b}$; $C_{2-6}$ alkynyl substituted with 0-1 $R^{1b}$, aryl substituted with 0-1 $R^{1b}$, heteroaryl substituted with 0-1 $R^{1b}$, $C_{5-6}$ cycloalkyl substituted with 0-1 $R^{1b}$, and a heterocycle substituted with 0-1 $R^{1b}$;

$R^{1b}$, at each occurrence, is selected from Cl, F, methanesulfonyl, and $C_{1-4}$ alkyl substituted with 0-3 $R^{1c}$, and;

$R^{1c}$, at each occurrence, is selected from Cl, F and a heterocycle;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH optionally substituted with $C_{1-4}$ alkyl, Cl, F, methanesulfonyl, aryl, heteroaryl, $C_{5-6}$ cycloalkyl, and a heterocycle;

$R^3$ is selected from Cl, F, $CH_3$, and $CH_2CH_3$.

In another embodiment, the present invention provides a novel compound of formula IIa or a pharmaceutically acceptable salt thereof, wherein:

$R^1$ is H, $C_{1-6}$ alkyl, aryl, 5-6 membered heteroaryl consisting of carbon atoms and 1-2 heteroatoms selected from O and N; $C_{3-10}$ cycloalkyl, wherein each $R^1$ group is substituted with 0-1 $R^{1a}$;

$R^{1a}$, at each occurrence, is selected from $C_{1-4}$ alkyl substituted with 0-3 $R^{1b}$; $C_{2-6}$ alkynyl substituted with 0-1 $R^{1b}$ aryl substituted with 0-1 $R^{1b}$, 5-6 membered heteroaryl substituted with 0-1 $R^{1b}$ and consisting of carbon atoms and 1-2 heteroatoms selected from O and N, $C_{5-6}$ cycloalkyl substituted with 0-1 $R^{1b}$, and a 5-6 membered heterocycle substituted with 0-1 $R^{1b}$;

$R^{1b}$, at each occurrence, is selected from Cl, F, methanesulfonyl, and $C_{1-4}$ alkyl substituted with 0-3 $R^{1c}$, and;

$R^{1c}$, at each occurrence, is selected from Cl, F and a 5-6 membered heterocycle consisting of carbon atoms and 1-2 heteroatoms selected from O and N;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O and N;

$R^{2b}$, at each occurrence, is selected from OH optionally substituted with $C_{1-4}$ alkyl, Cl, F, methanesulfonyl, aryl, 5-6 membered heteroaryl consisting of carbon atoms and 1-2 heteroatoms selected from O and N, $C_{5-6}$ cycloalkyl, and a 5-6 membered heterocycle consisting of carbon atoms and 1-2 heteroatoms selected from O and N;

$R^3$ is selected from Cl, F, $CH_3$, and $CH_2CH_3$.

In another embodiment, the present invention provides a novel compound of formula IIb

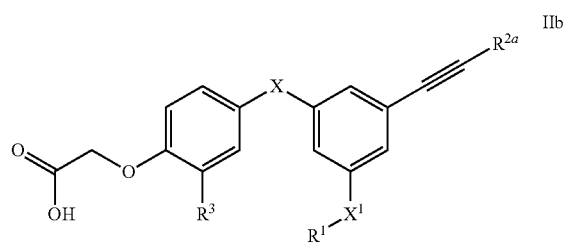

or a pharmaceutically acceptable salt thereof.

In another embodiment, the present invention provides a novel compound of formula IIb, wherein $R^1$ is $C_{1-6}$ alkyl.

In another embodiment, the present invention provides a novel compound of formula IIb, wherein $R^{2a}$ is $C_{1-4}$ alkyl substituted with a heterocycle.

In another embodiment, the present invention provides a novel compound of formula IIb, wherein $R^{2a}$ is $C_{1-4}$ alkyl substituted with morpholinyl.

In another embodiment, the present invention provides a novel compound of formula IIb, wherein $R^3$ is selected from Cl and $CH_3$.

In another embodiment, the present invention provides a novel compound of formula IIb, wherein X is selected from S and $SCH_2$ In another embodiment, the present invention provides a novel compound of formula IIb, wherein X is S.

In another embodiment, the present invention provides a novel compound of formula IIb, wherein X is $SCH_2$.

In another embodiment, the present invention provides a novel compound of formula IIb, wherein $X^1$ is O.

In another embodiment, the present invention provides a novel compound of formula IIb, wherein $X^1$ is S.

In another embodiment, the present invention provides a novel compound of formula IIb, wherein: $R^1$ is aryl substituted with 0-1 $R^{1a}$; wherein $R^{1a}$, at each occurrence, is selected from OH, SH, Cl, F, $NH_2$, —CN, $NO_2$, $C_{1-4}$ alkyl.

In another embodiment, the present invention provides a novel compound of formula IIb, wherein $R^1$ is $C_{1-6}$ alkyl substituted with $R^{1a}$; and wherein $R^{1a}$ is aryl substituted with 0-1 $R^{1b}$; and wherein $R^{1b}$ is selected from OH, SH, Cl, F, $NH_2$, —CN, $NO_2$, $C_{1-4}$ alkyl.

In another embodiment, the present invention provides a novel compound of formula IIb, wherein: $R^1$ is $C_{1-6}$ alkyl substituted with $R^{1a}$, wherein $R^{1a}$ is heteroaryl substituted with 0-1 $R^{1b}$; and wherein $R^{1b}$ is selected from OH, SH, Cl, F, $NH_2$, —CN, $NO_2$, $C_{1-4}$ alkyl.

In another embodiment, the present invention provides a novel compound of formula IIb, wherein: $R^1$ is $C_{1-6}$ alkyl substituted with $R^{1a}$, wherein $R^{1a}$ is heterocyclyl substituted with 0-1 $R^{1b}$; and wherein $R^{1b}$ is selected from OH, SH, Cl, F, $NH_2$, —CN, $NO_2$, $C_{1-4}$ alkyl.

In another embodiment, the present invention provides a novel compound of formula IIb, wherein: $R^1$ is $C_{1-6}$ alkyl substituted with $R^{1a}$, wherein $R^{1a}$ is $C_{5-6}$ cycloalkyl substituted with 0-2 $R^{1b}$; and wherein $R^{1b}$ is selected from OH, SH, Cl, F, $NH_2$, —CN, $NO_2$, $C_{1-4}$ alkyl.

In another embodiment, the present invention provides a novel compound of formula IIb, wherein: $R^{2a}$ is aryl substituted with $R^{2b}$; wherein $R^{2b}$ is selected from OH, SH, Cl, F, $NH_2$, —CN, $NO_2$, $C_{1-4}$ alkyl.

In another embodiment, the present invention provides a novel compound of formula IIb, wherein: $R^{2a}$ is $C_{1-6}$ alkyl substituted with $R^{2b}$; wherein $R^{2b}$ is selected from aryl substituted with $R^{2c}$; and wherein $R^{2c}$ is selected from OH, SH, Cl, F, $NH_2$, —CN, $NO_2$, $C_{1-4}$ alkyl.

In another embodiment, the present invention provides a novel compound of formula IIb, wherein: $R^{2a}$ is $C_{1-6}$ alkyl substituted with $R^{2b}$; wherein $R^{2b}$ is selected from heteroaryl substituted with $R^{2c}$; and wherein $R^{2c}$ is selected from OH, SH, Cl, F, $NH_2$, —CN, $NO_2$, $C_{1-4}$ alkyl.

In another embodiment, the present invention provides a novel compound selected from:

{2-Chloro-4-[3-(4-chloro-phenylethynyl)-5-(3-piperidin-1-yl-propoxy)-phenylsulfanyl]-phenoxy}-acetic acid;

{2-Methyl-4-[3-(3-morpholin-4-yl-propoxy)-5-phenylethynyl-phenylsulfanyl]-phenoxy}-acetic acid;

{2-Chloro-4-[3-(4-chloro-phenylethynyl)-5-(3-morpholin-4-yl-propoxy)-phenylsulfanyl]-phenoxy}-acetic acid;

{2-Chloro-4-[3-(4-chloro-phenylethynyl)-5-(4-morpholin-4-ylmethyl-benzyloxy)-phenylsulfanyl]-phenoxy}-acetic acid;

{2-Chloro-4-[3-(4-chloro-phenylethynyl)-5-(1-methyl-piperidin-4-ylmethoxy)-phenylsulfanyl]-phenoxy}-acetic acid;

{2-Methyl-4-[3-(3-morpholin-4-yl-propoxy)-5-(3-phenyl-prop-1-ynyl)-phenylsulfanyl]-phenoxy}-acetic acid;

{4-[3-(4-Fluoro-benzyloxy)-5-(3-morpholin-4-yl-prop-1-ynyl)-phenylsulfanyl]-2-methyl-phenoxy}-acetic acid;

{4-[3-Cyclohexylmethoxy-5-(3-morpholin-4-yl-prop-1-ynyl)-phenylsulfanyl]-2-methyl-phenoxy}-acetic acid;

{4-[3-Isobutoxy-5-(3-morpholin-4-yl-prop-1-ynyl)-phenylsulfanyl]-2-methyl-phenoxy}-acetic acid;

{4-[3-(4-Chloro-benzyloxy)-5-(3-morpholin-4-yl-prop-1-ynyl)-phenylsulfanyl]-2-methyl-phenoxy}-acetic acid;

{2-Chloro-4-[3-(4-chloro-phenylethynyl)-5-hydroxy-phenylsulfanyl]-phenoxy}-acetic acid;

{4-[3-But-2-ynyloxy-5-(3-morpholin-4-yl-prop-1-ynyl)-phenylsulfanyl]-2-methyl-phenoxy}-acetic acid;
{2-Methyl-4-[3-(2-morpholin-4-yl-ethoxy)-5-phenylethynyl-phenylsulfanyl]-phenoxy}-acetic acid;
{2-Chloro-4-[3-(3-methoxy-prop-1-ynyl)-5-(3-morpholin-4-yl-propoxy)-phenyl-sulfanyl]-phenoxy}-acetic acid;
{2-Chloro-4-[3-(3-morpholin-4-yl-propoxy)-5-pent-1-ynyl-phenylsulfanyl]-phenoxy}-acetic acid;
{2-Methyl-4-[3-(3-morpholin-4-yl-propoxy)-5-(3-phenyl-prop-1-ynyl)-benzylsulfanyl]-phenoxy}-acetic acid;
{4-[3-(4-Fluoro-benzyloxy)-5-(3-morpholin-4-yl-prop-1-ynyl)-benzylsulfanyl]-2-methyl-phenoxy}-acetic acid; and,
{2-Methyl-4-[3-(3-morpholin-4-yl-ethoxy)-5-(3-phenyl-prop-1-ynyl)-benzylsulfanyl]-phenoxy}-acetic acid;
or a pharmaceutically acceptable salt thereof.

In another embodiment, the present invention provides a novel compound selected from:
{4-[3-Cyclohexylmethoxy-5-(4-methanesulfonyl-phenylethynyl)-phenylsulfanyl]-2-methyl-phenoxy}-acetic acid;
{4-[3-Cyclopentylmethoxy-5-(4-methanesulfonyl-phenylethynyl)-phenylsulfanyl]-2-methyl-phenoxy}-acetic acid;
{4-[3-Isobutoxy-5-(4-methanesulfonyl-phenylethynyl)-phenylsulfanyl]-2-methyl-phenoxy}-acetic acid;
{4-[3-[2-(4-Chloro-phenyl)-ethoxy]-5-(4-methanesulfonyl-phenylethynyl)-phenyl-sulfanyl]-2-methyl-phenoxy}-acetic acid;
{4-[3-[2-(4-Chloro-phenyl)-ethoxy]-5-(3-morpholin-4-yl-prop-1-ynyl)-phenylsulfanyl]-2-methyl-phenoxy}-acetic acid;
{4-[3-[2-(4-Chloro-phenyl)-ethoxy]-5-(4-hydroxymethyl-phenylethynyl)-phenyl-sulfanyl]-2-methyl-phenoxy}-acetic acid;
{4-[3-(2-Ethyl-butoxy)-5-phenylethynyl-phenylsulfanyl]-2-methyl-phenoxy}-acetic acid;
[4-(3-Cyclopentyloxy-5-phenylethynyl-phenylsulfanyl)-2-methyl-phenoxy]-acetic acid;
{4-[3-(4-Fluoro-phenylethynyl)-5-(4-methanesulfonyl-benzyloxy)-phenylsulfanyl]-2-methyl-phenoxy}-acetic acid;
[4-(3-Cyclopentylmethoxy-5-phenylethynyl-phenylsulfanyl)-2-methyl-phenoxy]-acetic acid;
{4-[3-(2-Cyclohexyl-ethoxy)-5-phenylethynyl-phenylsulfanyl]-2-methyl-phenoxy}-acetic acid;
{4-[3-(2-Ethyl-butoxy)-5-(3-morpholin-4-yl-prop-1-ynyl)-phenylsulfanyl]-2-methyl-phenoxy}-acetic acid;
{4-[3-Cyclopentyloxy-5-(3-morpholin-4-yl-prop-1-ynyl)-phenylsulfanyl]-2-methyl-phenoxy}-acetic acid;
{4-[3-(2-Cyclohexyl-ethoxy)-5-(3-morpholin-4-yl-prop-1-ynyl)-phenylsulfanyl]-2-methyl-phenoxy}-acetic acid;
{4-[3-Cyclopentylmethoxy-5-(3-morpholin-4-yl-prop-1-ynyl)-phenylsulfanyl]-2-methyl-phenoxy}-acetic acid;
{4-[3-Cyclopentylmethoxy-5-(3-morpholin-4-yl-prop-1-ynyl)-phenylsulfanyl]-2-methyl-phenoxy}-acetic;
{4-[3-Isobutoxy-5-(3-morpholin-4-yl-prop-1-ynyl)-benzylsulfanyl]-2-methyl-phenoxy}-acetic acid;
[4-(3-Isobutoxy-5-phenylethynyl-benzylsulfanyl)-2-methyl-phenoxy]-acetic acid;
{4-[3-Isobutoxy-5-(4-methanesulfonyl-phenylethynyl)-benzylsulfanyl]-2-methyl-phenoxy}-acetic acid;
{4-[3-(4-Methanesulfonyl-phenylethynyl)-5-(5-trifluoromethyl-pyridin-2-yloxy)-phenylsulfanyl]-2-methyl-phenoxy}-acetic acid;
{4-[3-(4-Methanesulfonyl-phenylethynyl)-5-(3-trifluoromethyl-pyridin-2-yloxy)-phenylsulfanyl]-2-methyl-phenoxy}-acetic acid;
{2-Methyl-4-[3-(3-morpholin-4-yl-prop-1-ynyl)-5-(3-trifluoromethyl-pyridin-2-yloxy)-phenylsulfanyl]-phenoxy}-acetic acid;
{2-Methyl-4-[3-(3-morpholin-4-yl-prop-1-ynyl)-5-(5-trifluoromethyl-pyridin-2-yloxy)-phenylsulfanyl]-phenoxy}-acetic acid;
{2-Methyl-4-[3-(3-morpholin-4-yl-prop-1-ynyl)-5-(3-trifluoromethyl-phenoxy)-phenylsulfanyl]-phenoxy}-acetic acid;
{4-[3-(4-Methanesulfonyl-phenylethynyl)-5-(3-trifluoromethyl-phenoxy)-phenyl-sulfanyl]-2-methyl-phenoxy}-acetic acid; and
{2-Methyl-4-[3-phenylethynyl-5-(5-trifluoromethyl-pyridin-2-yloxy)-phenylsulfanyl]-phenoxy}-acetic acid,
or a pharmaceutically acceptable salt thereof.

In another embodiment, the present invention provides a novel compound of formula III:

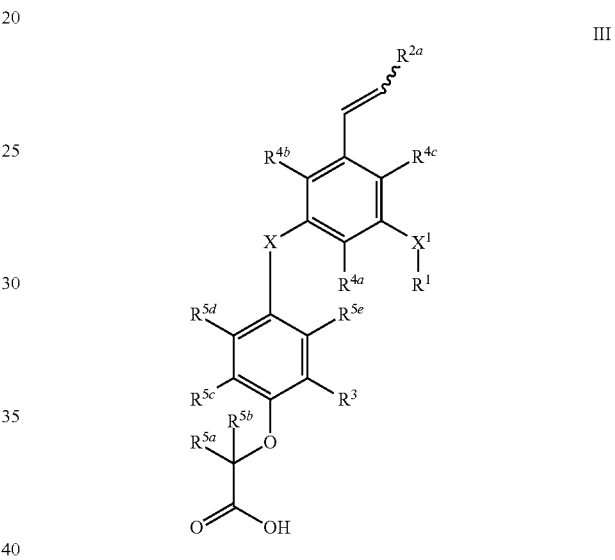

or a pharmaceutically acceptable salt thereof, wherein:
$R^1$ is $C_{1-4}$ alkyl substituted with 1-2 $R^{1a}$;
$R^{1a}$, at each occurrence, is selected from aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$
$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$;
$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{3-6}$ cycloalkyl substituted with 0-2 $R^{1d}$, and a heterocycle substituted with 0-2 $R^{1d}$;
$R^{1d}$, at each occurrence, is selected from OH, SH, Cl, F, $NH_2$, —CN, $NO_2$, $C_{1-4}$ alkyl, and $C_{2-4}$ alkenyl;
$R^{2a}$ is selected from aryl substituted with 0-2 $R^{2b}$ and heteroaryl substituted with 0-2 $R^{2b}$;
$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, heteroaryl substituted with 0-2 $R^{2c}$, $C_{3-6}$ cycloalkyl substituted with 0-2 $R^{2c}$, and a heterocycle substituted with 0-2 $R^{2c}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and heteroaryl substituted with 0-2 $R^{2d}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$; and,
$R^{5e}$, at each occurrence, is selected from H, Cl, F, and $CH_3$.

In another embodiment, the present invention provides a novel compound of formula III or a pharmaceutically acceptable salt thereof, wherein:

$R^1$ is $C_{1-4}$ alkyl substituted with 1-2 $R^{1a}$;

$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from aryl substituted with 0-2 $R^{2b}$ and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2c}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$; and,
$R^{5e}$, at each occurrence, is selected from H, Cl, F, and $CH_3$.

In another embodiment, the present invention provides a novel compound of formula IIIa

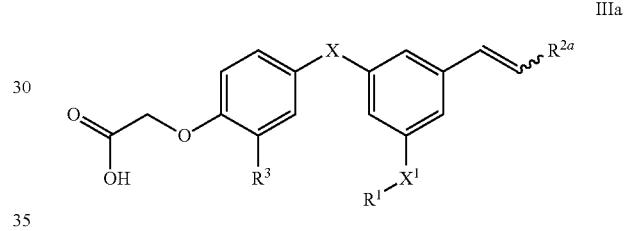

IIIa or a pharmaceutically acceptable salt thereof, wherein:

$R^{1a}$, at each occurrence, is selected from aryl substituted with 0-2 $R^{1b}$, heteroaryl substituted with 0-2 $R^{1b}$, $C_{5-6}$ cycloalkyl substituted with 0-2 $R^{1b}$, and a heterocycle substituted with 0-2 $R^{1b}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{5-6}$ cycloalkyl substituted with 0-2 $R^{1c}$, and a heterocycle substituted with 0-2 $R^{1c}$ $R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^d$, $C_{3-6}$ cycloalkyl substituted with 0-2 $R^{1d}$, and a heterocycle substituted with 0-2 $R^d$;

$R^{2a}$ is selected from aryl substituted with 0-2 $R^{2b}$ and heteroaryl substituted with 0-2 $R^{2b}$ and;

$R^{2b}$, at each occurrence, is selected from OH, SH, Cl, F, $NH_2$, —CN, $NO_2$, $C_{1-4}$ alkyl, $C_{2-4}$ alkenyl, aryl, heteroaryl, $C_{5-6}$ cycloalkyl, and a heterocycle.

In another embodiment, the present invention provides a novel compound of formula IIIa or a pharmaceutically acceptable salt thereof, wherein:

$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{2a}$ is selected from aryl substituted with 0-2 $R^{2b}$ and 5-6 membered heteroaryl substituted with 0-2 $R^{2b}$ and consisting of carbon atoms and 1-2 heteroatoms selected from O, N, and $S(O)_{0-2}$; and, $R^{2b}$, at each occurrence, is selected from OH, SH, Cl, F, $NH_2$, —CN, $NO_2$, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$.

In another embodiment, the present invention provides a novel compound of formula Ia, wherein:

$R^1$ is $C_{1-4}$ alkyl substituted with 1-2 $R^{1a}$;

$R^{1a}$, at each occurrence, is selected from aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{3-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^2$ is aryl substituted with 0-3 $R^{2a}$ or heteroaryl substituted with 0-2 $R^{2a}$;

$R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, heteroaryl substituted with 0-2 $R^{2b}$, $C_{3-6}$ cycloalkyl substituted with 0-2 $R^{2b}$, and a heterocycle substituted with 0-2 $R^{2b}$;

$R^{2b}$, at each occurrence, is selected from OH, SH, Cl, F, $NH_2$, —CN, $NO_2$, $C_{1-4}$ alkyl, and, $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

In another embodiment, the present invention provides a novel compound of formula Ia, wherein:

$R^1$ is $C_{1-4}$ alkyl substituted with 1-2 $R^{1a}$;

$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^2$ is aryl substituted with 0-3 $R^{2a}$ or 5-10 membered heteroaryl substituted with 0-2 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-6}$ cycloalkyl substituted with 0-2 $R^{2b}$, and a 3-6 membered heterocycle substituted with 0-2 $R^{2b}$ and consisting of carbon atoms and 1-2 heteroatoms selected from O, N, and $S(O)_{0-2}$;

$R^{2b}$, at each occurrence, is selected from OH, SH, Cl, F, $NH_2$, —CN, $NO_2$, $C_{1-4}$ alkyl, and, $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

In another embodiment, the present invention provides a novel compound of formula Ib:

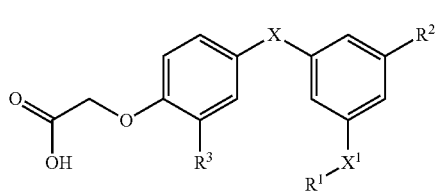

or a pharmaceutically acceptable salt thereof, wherein:

$R^1$ is $C_{1-4}$ alkyl substituted with 1 $R^{1a}$;

$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^2$ is aryl substituted with 0-2 $R^{2a}$ or 5-6 membered heteroaryl substituted with 0-2 $R^{2a}$ and consisting of carbon atoms and 1-2 heteroatoms selected from O, N, and $S(O)_{0-2}$; and, $R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, 5-6 membered heteroaryl substituted with 0-2 $R^{2b}$ and consisting of carbon atoms and 1-2 heteroatoms selected from O, N, and $S(O)_{0-2}$, $C_{5-6}$ cycloalkyl substituted with 0-2 $R^{2b}$, and a 5-6 membered heterocycle substituted with 0-2 $R^{2b}$ and consisting of carbon atoms and 1-2 heteroatoms selected from O, N, and $S(O)_{0-2}$.

In another embodiment, the present invention provides a novel compound pharmaceutical composition, comprising: a pharmaceutically acceptable carrier and a compound of the present invention or a pharmaceutically acceptable salt thereof.

In another embodiment, the present invention provides a novel method of treating type 2 diabetes, comprising: administering a therapeutically effective amount of a compound of the present invention or a pharmaceutically acceptable salt thereof.

In another embodiment, the present invention provides a method of treating a disease comprising administering to a patient in need thereof a therapeutically effective amount of a compound of the present invention or a pharmaceutically acceptable salt thereof, wherein the disease is selected from dyslipidemia, syndrome X (including the metabolic syndrome, e.g., hypertension, impaired glucose tolerance (IGT), insulin resistance, hypertrigyceridaemia, and obesity), cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke), hyperglycemia, hyperlipidemia, hypercholesterolemia, and hyperinsulinemia.

In another embodiment, the present invention provides a method of treating a disease comprising administering to a patient in need thereof a therapeutically effective amount of at least one compound of the present invention or a pharmaceutically acceptable salt thereof, wherein the disease is selected from non-insulin requiring Type 2 diabetes to insulin requiring Type 2 diabetes, decreasing apoptosis in mammalian cells (e.g., beta cells of Islets of Langerhans), renal diseases (e.g., glomerulonephritis, glomerulosclerosis, nephrotic syndrome, and hypertensive nephrosclerosis), improving cognitive functions in dementia, treating diabetic complications, psoriasis, polycystic ovarian syndrome (PCOS), prevention and treatment of bone loss (e.g. osteoporosis), and lowering the bio-markers of atherosclerosis (e.g., c-reactive protein (CRP), TNF-α, and IL-6).

In another embodiment, the present invention provides a novel process for the preparation of the compounds of the present invention or stereoisomers or pharmaceutically acceptable salts thereof.

In another embodiment, the present compounds are administered in combination with one or more further pharmacologically active substances selected from antiobesity agents, appetite regulating agents, antidiabetics, antihypertensive agents, agents for the treatment of complications resulting from or associated with diabetes, and agents for the treatment of complications and disorders resulting from or associated with obesity.

Suitable additional substances may be selected from CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

Suitable antiobesity agents include leptin, dexamphetamine, amphetamine, fenfluramine, dexfenfluramine, sibutramine, orlistat, mazindol, and phentermine.

Suitable antidiabetics include insulin, orally active hypoglycaemic agents, and GLP-1 (glucagon like peptide-1) derivatives (see WO 98/08871).

Orally active hypoglycaemic agents preferably include sulphonylureas, biguanides, meglitinides, glucosidase inhibitors, glucagon antagonists (see WO99/01423), GLP-1 agonists, potassium channel openers (see WO 97/26265 and WO 99/03861), DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism (e.g., antihyperlipidemic agents and antilipidemic agents), compounds lowering food intake, RXR agonists, agents acting on the ATP-dependent potassium channel of the β-cells, and thiazolidinediones (e.g., troglitazone, ciglitazone, pioglitazone and rosiglitazone).

Agents to be administered in combination with compounds of the present invention also include sulphonylureas (e.g., tolbutamide, glibenclamide, glipizide, and glicazide), biguanides (e.g., metformin), meglitinides (e.g., repaglinide and senaglinide), α-glucosidase inhibitors (e.g., miglitol and acarbose), an agent acting on the ATP-dependent potassium channel of the β-cells (e.g., the above sulphonylureas and repaglinide), and nateglinide.

Antihyperlipidemic or antilipidemic agents include apolipoprotein A-I Milano, cholestyramine, colestipol, clofibrate, gemfibrozil, fenofibrate, bezafibrate, tesaglitazar, muraglitazar, EML-4156, LY-518674, LY-519818, MK-767, torcetrapib, atorvastatin, fluvastatin, lovastatin, pravastatin, simvastatin, cerivastin, rosuvastatin, pitavastatin, acipimox, ezetimibe, probucol, dextrothyroxine and nicotinic acid.

In another embodiment the present compounds are administered in combination with more than one of the above-mentioned compounds (e.g, in combination with a sulphonylurea and metformin, a sulphonylurea and acarbose, repaglinide and metformin, insulin and a sulphonylurea, insulin and metformin, or insulin and lovastatin).

Examples of antihypertensive agents include β-blockers (e.g, alprenolol, atenolol, timolol, pindolol, propranolol, and metoprolol), ACE (angiotensin converting enzyme) inhibitors (e.g., benazepril, captopril, enalapril, fosinopril, lisinopril, quinapril and ramipril), calcium channel blockers (e.g., nifedipine, felodipine, nicardipine, isradipine, nimodipine, diltiazem and verapamil), and α-blockers (e.g., doxazosin, urapidil, prazosin and terazosin).

It should be understood that any suitable combination of the compounds according to the invention with one or more of the above-mentioned compounds and optionally one or more further pharmacologically active substances are considered to be within the scope of the present invention.

It is preferred that the compounds of the present invention have a solubility in water of at least 0.1 mg/L as determined at 25° C. and pH 7.0. More preferably the solubility is at least 0.5 mg/L. Even more preferably the solubility is at least 1 mg/L. Still more preferably, the solubility is at least 2 mg/L. Further preferably the solubility is at least 10 mg/L. Even further preferably the solubility is at least 50 mg/L. Still further preferably the solubility is at least 200 mg/L.

It is preferred that compounds of the present invention have an $IC_{50}$ value of less than 5 μm as determined by the PPAR transient transactivation assay. More preferably the $IC_{50}$ value is less than 1 μm. Even more preferably the $IC_{50}$ value is less than 500 nM. Still more preferably the $IC_{50}$ value is less than 100 nM. Further preferably the $IC_{50}$ value is less than 50 nM. Even further preferably the $IC_{50}$ value is less than 25 nM. Still further preferably the $IC_{50}$ value is less than 10 nM. Even still further preferably the $IC_{50}$ value is less than 5 nM.

It is preferred that the compounds of the present invention have a molecular weight of less than 1000 g/mol. More preferably the molecular weight is less than 750 g/mol. Even more preferably the molecular weight is less than 600 g/mol. Still more preferably, the molecular weight is less than 550 g/mol. Further preferably the molecular weight is less than 500 g/mol. Even further preferably the molecular weight is less than 400 g/mol.

It is preferred that compounds of the present invention are ionized at pH 7.4.

It is preferred that the compounds of the present invention have only one ionized carboxylic acid group at a pH of from 5.5-9. More preferably the compounds have only one ionized carboxylic acid group at a pH of from 6-8. Even more preferably the compounds have only one ionized carboxylic acid group at a pH of from 6.5-7.5. Still more preferably, the compounds have only one ionized carboxylic acid group at pH 7.4.

It is preferred that the compounds of the present invention are zwitter-ionic with one ionized amine group and one ionized carboxylic acid group at a pH of from 5.5-9. More preferably the compounds are zwitter-ionic with one ionized amine group and one ionized carboxylic acid group at a pH of from 6-8. Even more preferably the compounds are zwitter-ionic with one ionized amine group and one ionized carboxylic acid group at a pH of from 6.5-7.5. Still more preferably, the compounds are zwitter-ionic with one ionized amine group and one ionized carboxylic acid group at pH 7.4.

Pharmaceutical Compositions

The compounds of the invention may be administered alone or in combination with pharmaceutically acceptable carriers or excipients, in either single or multiple doses. The pharmaceutical compositions of the present invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995. The compositions may appear in conventional forms, which include capsules, tablets, aerosols, solutions, suspensions, and topical applications.

Typical compositions include a compound of the present invention a pharmaceutically acceptable acid addition salt thereof, associated with a pharmaceutically acceptable excipient, which may be a carrier or a diluent or be diluted by a carrier, or enclosed within a carrier, which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

If desired, the pharmaceutical composition of the invention may comprise a compound of the present invention in combination with further pharmacologically active substances such as those described in the foregoing.

The compounds of the invention may be administered to a mammal, especially a human in need of such treatment, prevention, elimination, alleviation or amelioration of diseases related to the regulation of blood sugar. Mammals also include animals, both domestic animals, e.g. household pets, and non-domestic animals such as wildlife.

The compounds of the present invention are expected to be effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

DEFINITIONS

All references described herein are incorporated in there entirety by reference.

"Substituted" signifies that one or more hydrogen atoms are replaced by the designated substituent. Only pharmaceutically stable compounds are intended to be covered.

When examples of definitions are provided, the definition is not meant to be limited to the specific examples.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When O or S is listed as a substituent, oxo and sulfo, respectively, it is intended that a carbon atom be replaced by either the O or S. For example if alkyl were substituted by O, then an ether would be formed. Preferably heteroatom-heteroatom bonds such as O—O, O—S, O—N, S—S, and S—N are not formed.

"Alkyl" includes both straight chain and branched alkyl groups having the designated number of carbon atoms (e.g., 1, 2, 3, 4, 5, 6, 7, or 8). Examples of alkyl groups include methyl, ethyl, n-propyl, i-propyl, n-butyl, i-butyl, s-butyl, t-butyl, 2-methyl-butyl, and 2-ethyl-butyl.

"Alkenyl" includes both straight chain and branched alkenyl groups having the designated number of carbon atoms (e.g., 2, 3, 4, 5, 6, 7, or 8). Examples of alkenyl groups include ethenyl, 1-propenyl, 2-propenyl, 1-butenyl, 2-butenyl, and 2-methyl-butenyl.

"Alkynyl" includes both straight chain and branched alkynyl groups having the designated number of carbon atoms (e.g., 2, 3, 4, 5, 6, 7, or 8). Examples of alkynyl groups include ethynyl, 1-propynyl, 2-propynyl, 1-butynyl, 2-butynyl, and 2-methyl-butynyl.

"Aryl" includes phenyl, naphthyl, fluorene, anthracene, phenanthrenyl, azulenyl, and a partially saturated bicyclic carbocyclic ring. The partially saturated bicyclic carbocyclic ring consists of 8, 9, 10, 11, or 12 carbon atoms, preferably 8, 9, or 10 carbon atoms. Examples of partially saturated bicyclic carbocyclic rings include 1,2,3,4-tetrahydronaphthyl, indanyl, indenyl, 1,2,4α,5,8,8α-hexahydronaphtyl, and 1,3α-dihydropentalene. A preferred aryl group is phenyl.

"Cycloalkyl" means a ring having the number of designated carbon atoms and having only single bonds between the carbon atoms. Examples of cycloalkyl include, but are not limited to cyclopropyl, cyclobutyl, cyclopentyl, cyclohexyl, and cycloheptyl. Preferred cycloalkyl groups are cyclopentyl and cyclohexyl.

"Heteroaryl" signifies a mono-, bi-, or tricyclic ring consisting of carbon atoms and from one heteroatom to 5, wherein the heteroatom is selected from oxygen, nitrogen, and sulphur. If sulphur is present, then it can be mono- or di-oxidized. If a nitrogen is present, then it can be N, NH, or substituted N. The heterocycle can be attached via a carbon or nitrogen atom, unless linking the nitrogen atom would lead to a quaternary nitrogen. If the heteroaryl is bicyclic, then one or both of the rings may have a heteroatom(s) present. If the heteroaryl is tricyclic, then one, two, or all three of the rings may have a heteroatom(s) present. If the heterocycle is monocyclic, then this ring is aromatic (e.g., fully unsaturated). If the heteroaryl is bicyclic or tricyclic, then at least one ring is aromatic.

Examples of "heteroaryl" are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4- triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imdazothiazolyl (e.g. imidazo[2,1-b]thiazolyl), triazolopyridinyl (e.g. triazolo[4,5-b]pyridinyl), triazolopyrimidinyl (e.g. 8-azapurinyl), carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo[b]furan]-1-yl, spiro[piperidine-4,3'-coumarin]-1-yl. A preferred heteroaryl is pyridinyl.

Other examples of "heteroaryl" are furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinyl, indolyl, benzimidazolyl, benzofuranyl, benzothienyl, pteridinyl and purinyl.

"Heterocyclyl" or "heterocycle" (heterocycle) signifies a mono-, bi-, or tricyclic ring consisting of carbon atoms and from one heteroatom to 4, wherein the heteroatom is selected from oxygen, nitrogen, and sulphur. If sulphur is present, then it can be S, S(O), or S(O)$_2$. If nitrogen is present, then it can be N, NH, substituted N, or N-oxide. The heterocycle is a saturated or partially saturated ring. From 0-2 CH$_2$ groups of the heterocycle can be replaced by C(O). The heterocycle can be attached via a carbon or nitrogen atom, unless linking the nitrogen atom would lead to a quaternary nitrogen. If the heterocycle is bicyclic, then one or both of the rings may have a heteroatom(s) present. If the heterocycle is tricyclic, then one, two, or all three of the rings may have a heteroatom(s) present.

Examples of "heterocycle" are aziridinyl (e.g. aziridin-1-yl), azetidinyl (e.g. azetidin-1-yl, azetidin-3-yl), oxetanyl, pyrrolidinyl (e.g. pyrrolidin-1-yl, pyrrolidin-2-yl, pyrrolidin-3-yl), imidazolidinyl (e.g. imidazolidin-1-yl, imidazolidin-2-yl, imidazolidin-4-yl), oxazolidinyl (e.g. oxazolidin-2-yl, oxazolidin-3-yl, oxazolidin-4-yl), thiazolidinyl (e.g. thiazolidin-2-yl, thiazolidin-3-yl, thiazolidin-4-yl), isothiazolidinyl, piperidinyl (e.g. piperidin-1-yl, piperidin-2-yl, piperidin-3-yl, piperidin-4-yl), homopiperidinyl (e.g. homopiperidin-1-yl, homopiperidin-2-yl, homopiperidin-3-yl, homopiperidin-4-yl), piperazinyl (e.g. piperazin-1-yl, piperazin-2-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxothiomorpholinyl, 1,1-dioxothiomorpholinyl, tetrahydrofuranyl (e.g. tetrahydrofuran-2-yl, tetrahydrofuran-3-yl), tetrahydrothienyl, tetrahydro-1,1-dioxothienyl, tetrahydropyranyl (e.g. 2-tetrahydropyranyl), tetrahydrothiopyranyl (e.g. 2-tetrahydrothiopyranyl), 1,4-dioxanyl, 1,3-dioxanyl, octahydroindolyl (e.g. octahydroindol-1-yl, octahydroindol-2-yl, octahydroindol-3-yl, octahydroindol-5-yl), decahydroquinolinyl (e.g. decahydroquinolin-1-yl, decahydroquinolin-2-yl, decahydroquinolin-3-yl, decahydroquinolin-4-yl, decahydroquinolin-6-yl), decahydroquinoxalinyl (e.g. decahydroquinoxalin-1-yl, decahydroquinoxalin-2-yl, decahydroquinoxalin-6-yl), 3-azabicyclo[3.2.2]nonyl, 2-azabicyclo[2.2.1]heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, 1,4-dioxaspiro[4.5]decanyl (e.g. 1,4-dioxaspiro[4.5]decan-2-yl, 1,4-dioxaspiro[4.5]decan-7-yl), 1,4-dioxa-8-azaspiro[4.5]decanyl (e.g. 1,4-dioxa-8-azaspiro[4.5]decan-2-yl, 1,4-dioxa-8-azaspiro[4.5]decan-8-yl), 8-azaspiro[4.5]decanyl (e.g. 8-azaspiro[4.5]decan-1-yl, 8-azaspiro[4.5]decan-8-yl), 2-azaspiro[5.5]undecanyl (e.g. 2-azaspiro[5.5]undecan-2-yl), 2,8-diazaspiro[4.5]decanyl (e.g. 2,8-diazaspiro[4.5]decan-2-yl, 2,8-diazaspiro[4.5]decan-8-yl), 2,8-diazaspiro[5.5]undecanyl (e.g. 2,8-diazaspiro[5.5]undecan-2-yl), 1,3,8-triazaspiro[4.5]decanyl (e.g. 1,3,8-triazaspiro[4.5]decan-1-yl, 1,3,8-triazaspiro[4.5]decan-3-yl, and 1,3,8-triazaspiro[4.5]decan-8-yl).

Preferred examples of "heterocycle" are pyrrolidinyl, pyrrolinyl, tetrahydrofuranyl, dihydrofuranyl, tetrahydrothiophenyl, dihydrothiophenyl, imidzolidinyl, imidazolinyl, pyrazolidinyl, pyrazolinyl, oxazolidinyl, oxazoline, isoxazolidinyl, isoxazoline, thioxazolidinyl, thioxazoline, isothioxazolidinyl, isothioxazoline, triazolidinyl, triazolinyl, tetrazolidinyl, tetrazolinyl, tetrahydropyranyl, dihydropyranyl, pyran, piperidinyl, piperazinyl, homopiperazinyl, morpholinyl. Preferred heterocycle groups are piperidinyl and morpholinyl.

"Therapeutically effective amount" is intended to include an amount of a compound of the present invention that is effective when administered alone or in combination to activate glucokinase.

"Treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, e.g., arresting or slowing its development; and/or (c) relieving the disease-state, e.g., causing regression of the disease state itself or some symptom of the disease state.

Pharmaceutically acceptable include pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, and lactic acid wherever applicable or chiral bases such as brucine, (R)- or (S)-phenylethylamine, cinchona alkaloids and their derivatives. Commonly used methods are compiled by Jaques et al in "Enantiomers, Racemates and Resolution" (Wiley Interscience, 1981). More specifically a compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into a compound of the present invention. Conventional procedures for the selection and preparation of suitable prodrug derivatives are described, for example, in "Design of Prodrugs", ed. H. Bundgaard, Elsevier, 1985.

This invention will be better understood from the following examples, which are for purposes of illustration and are not intended to limit the invention defined in the claims which follow thereafter.

EXAMPLES

All reactions involving air-sensitive reagents were performed under nitrogen using syringe-septum cap techniques. The glassware was dried by heating with a heat-gun. $MgSO_4$ was used to dry solutions. Solvents were removed in vacuo by rotary evaporation. Melting points were recorded on a Büchi 535. Bruker AMX 400 and Bruker DRX 300 instruments were used to record $^1H$ NMR spectra at 400 and 300 MHz, respectively, with tetramethylsilane (TMS) as internal standard. Coupling constants (J) are given in Hz.

Materials

Test compounds were synthesized or when commercially available they were purchased from Aldrich, Specs, Maybridge, or Bionet. For the synthesized compounds, the procedure for synthesis and measured characteristics of the compound are stated in the example. All compounds for which no synthesis procedure is stated in the examples are commercially available and have been purchased or were prepared by standard methods described in the literature.

A general procedure may be as follows:

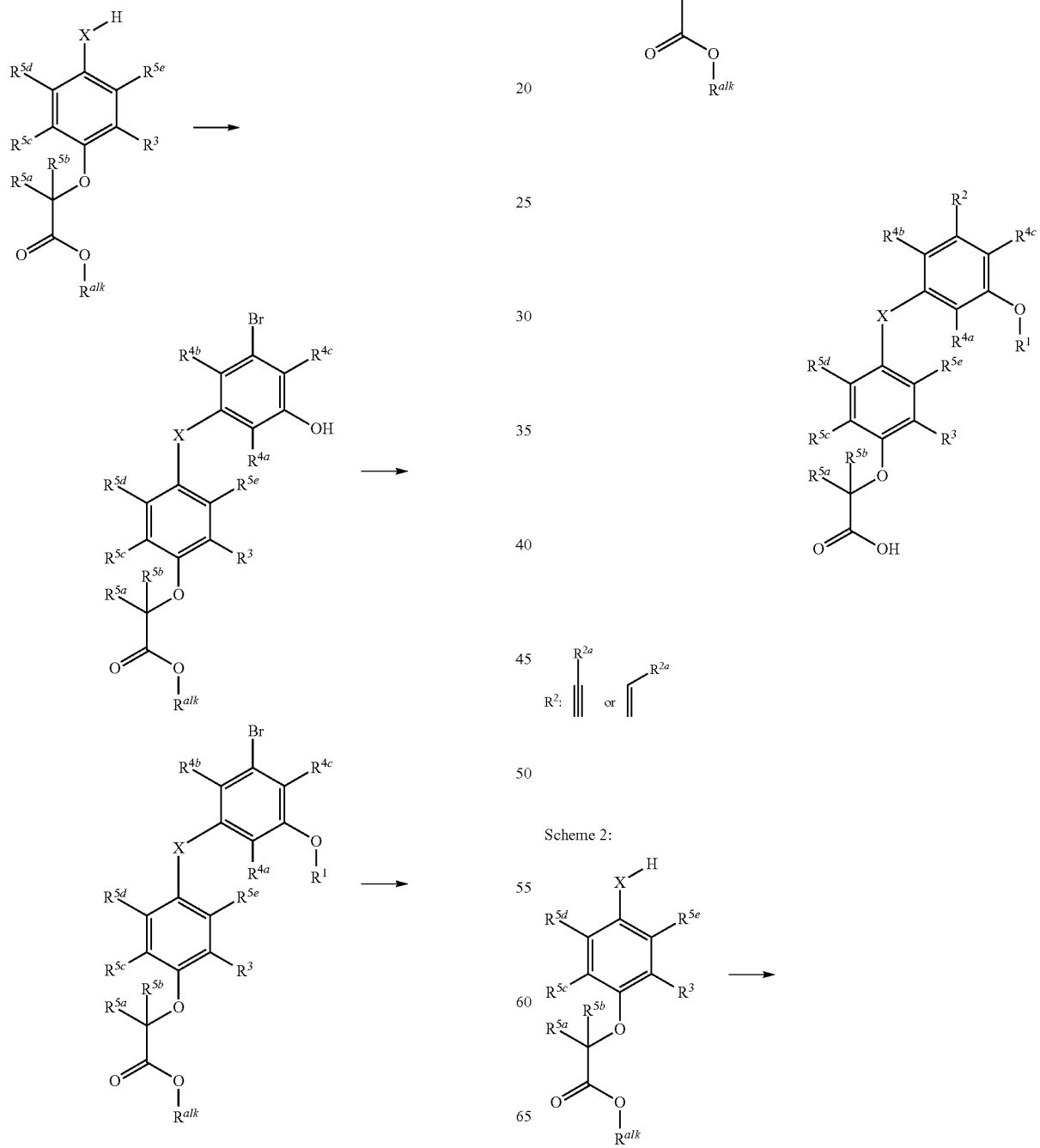

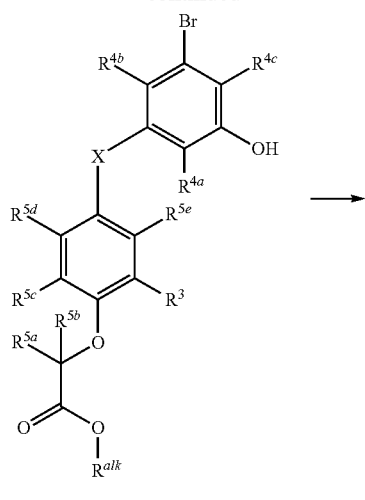
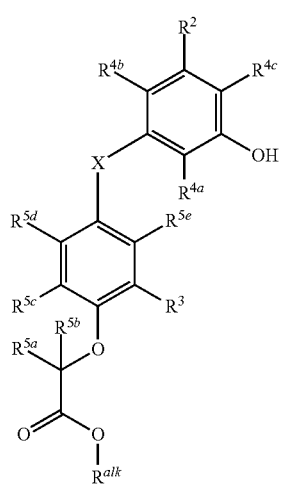
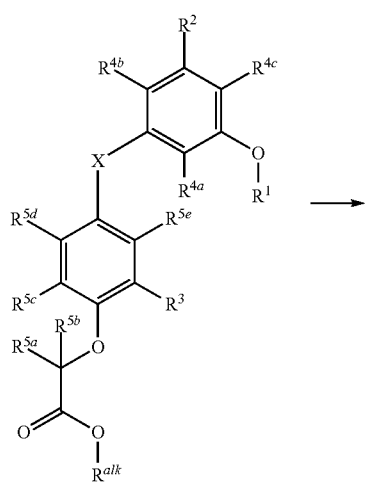
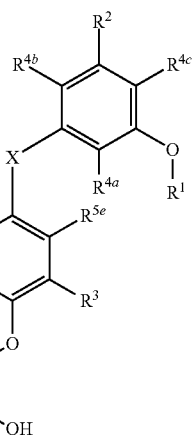
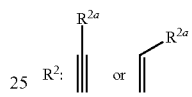
Scheme 3:
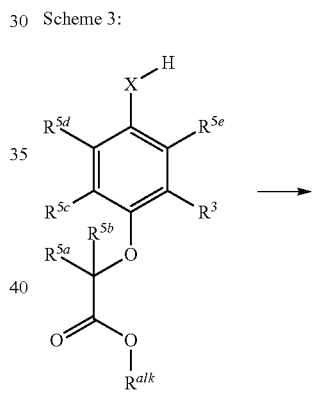
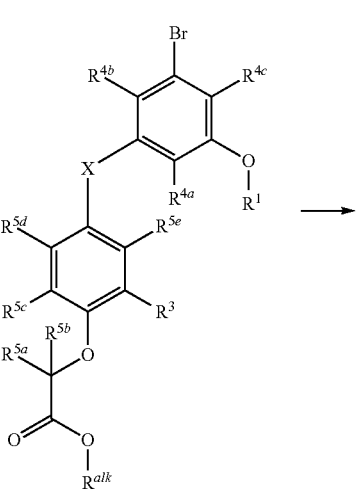

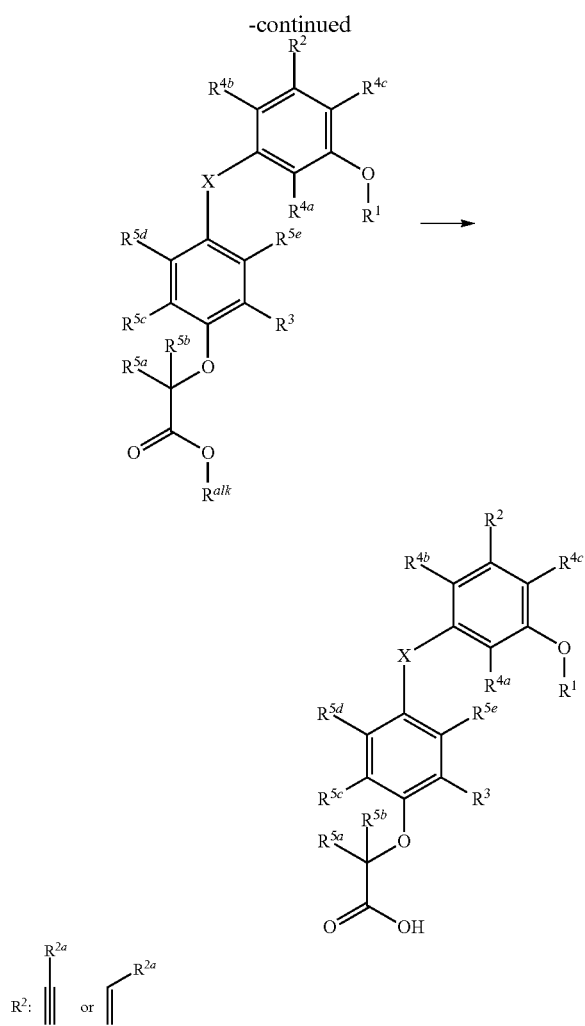

The synthetic intermediate of formula I with R1=H, R2=Br and a carboxylic ester group e.g. [4-(3-Bromo-5-hydroxy-phenylsulfanyl)-2-methyl-phenoxy]-acetic acid ethyl acetate can be converted via a classical Mitsunobu reaction or a reaction can be performed between the phenol and an alkyl halides (or an alkyle mesylate, triflate, tosylate or alike) to a new intermediate of formula I where X1-R1 forms a ether or thioether group and R=Br. The new intermediate can be converted via a classical Sonogashira, Heck or Suzuki coupling protocol to a new intermediate where R2 is —C≡C—$R^{2a}$, —CH=CH—$R^{2a}$ or a substituted or non substituted aryl or heteroaryl. It is also possible to perform the reaction in the opposite way by first performing the Sonogashira, Heck or Suzuki coupling followed by the ether forming reaction as described above. The claimed compounds can also be performed as described for [4-(3-Bromo-5-cyclopropyl-methoxy-phenylsulfanyl)-2-methyl-phenoxy]-acetic acid ethyl ester by condensing e.g. 1,3-dibromo-5-cyclopropyl-methoxy-benzene or another substituted dibromophenyle ether with (4-Mercapto-2-methyl-phenoxy)-acetic acid ethyl ester or another substituted mercaptobenzene. The intermediates formed can be converted to the claimed compounds by a classical ester hydrolyses reaction from the respective esters of I (scheme 1-3).

General Procedure (A)
HPLC Systems
HPLC Method A

The RP-purification was performed on a Gilson system (4 Gilson 306 pumps, Gilson 155 detector, Gilson reodyne manual injection, Gilson 811C mixer and a Gilson 202 fraction collector) using a Phenomenex RP synergi-MAX column (3 µm, 30 mm×250 mm) with gradient elution, 5% to 100% solvent B (acetonitrile) in solvent A (water) within 40 min, 60 mL/min, detection at 210 nm, room temperature. The pooled fractions were either evaporated to dryness in vacuo, or evaporated in vacuo until the MeCN is removed, and then frozen and freeze dried.

HPLC Method B

The RP-purification was performed on a Gilson system (3 Gilson 306 pumps, Gilson 170 DAD detector and a Gilson 215 liquid-handler) using a Waters X-terra RP (10 µm, 30 mm×150 mm) with gradient elution, 5% to 95% solvent B (0.05% TFA in acetonitrile) in solvent A (0.05% TFA in water) within 15 min, 40 mL/min, detection at 210 nm, room temperature. The pooled fractions were either evaporated to dryness in vacuo or evaporated in vacuo until the MeCN is removed and then frozen and freeze dried.

HPLC-MS (System 1)

The RP-analysis was performed on an Agilent HPLC system (1100 degasser, 1100 pump, 1100 injector and a 1100 DAD) fitted with an Agilent MS detector system Model VL (MW 0-1000) and a S.E.D.E.R.E Model Sedex 55 ELS detector system using a Waters X-terra MS C18 column (5 µm, 3.0 mm×50 mm) with gradient elution, 5% to 95% solvent B (0.05% TFA in acetonitrile) in solvent A (0.05% TFA in water) within 3 min, 2.7 mL/min.

Thin layer chromatography was performed on Merck DC-Alufolien, silica gel 60 $F_{254}$ and components were visualized by $UV_{254}$. Flash chromatography was performed using silica gel Merck 60 size 0.04-0-063 mm and a Quad 12/25 flash system.

3,5-dibromophenol was prepared as described by Yang, et al., *Synth Commun;* 2003, 33, 19, 3317-3326.

Intermediates

[4-(3-Bromo-5-hydroxy-benzylsulfanyl)-2-methyl-phenoxy]-acetic acid ethyl ester

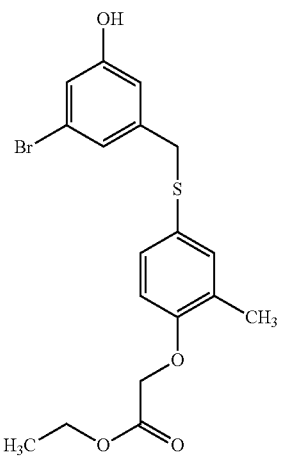 [SMILES: CCOC(=O)COc1ccc(SCc2cc(O)cc(Br)c2)cc1C]

Step A: tert-Butyl-(3,5-dibromo-phenoxy)-dimethyl-silane

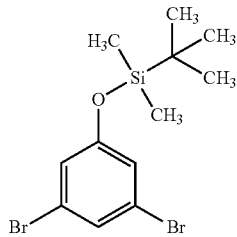 [SMILES: CC(C)(C)[Si](C)(C)Oc1cc(Br)cc(Br)c1]

3,5-Dibromophenol (59.6 mmol; 15 g) and imidazole (65.5 mmol; 4.5 g) were dissolved in dichloromethane (150 mL) and tert-butyl-dimethylsilylchloride (65.5 mmol; 9.9 g) was added. The reaction mixture was stirred at room temperature for 16 hours, diluted with diethyl ether, and filtered. The organic solution was washed with saturated ammonium chloride, saturated sodium hydrogen carbonate, and water and dried and evaporated to dryness. Yield: 22 g. HPLC-MS: m/z: 366.9 (M+); Rt: 3.09 min.

Step B: 3-Bromo-5-(tert-butyl-dimethyl-silanyloxy)-benzaldehyde

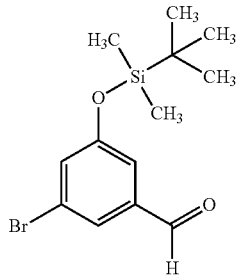 [SMILES: CC(C)(C)[Si](C)(C)Oc1cc(Br)cc(C=O)c1]

tert-Butyl-(3,5-dibromo-phenoxy)-dimethyl-silane (22 g; 60.08 mmol) was dissolved in THF (200 mL) in a dried reaction flask under an atmosphere of nitrogen. The mixture was cooled to −78° C. and n-BuLi (1.6 N in hexane; 41.25 mL; 66.09 mmol) was added while the temperature was kept between −60 and −78° C. The mixture was stirred for 15 min. and DMF (4.83 g; 66.08 mmol) was added. The reaction mixture was stirred for 1 h and methanol (5 mL) followed by saturated ammonium chloride was added. Ethyl acetate (200 mL) was added and the organic phase was separated from the aqueous phase. The organic phase was washed with water, dried, and evaporated to dryness. The crude product was purified by flash chromatography (heptane:dichloromethane (1:1). Yield 7 g. HPLC-MS: m/z: 317.0 (M+1); Rt: 2.7 min.

Step C: [3-Bromo-5-(tert-butyl-dimethyl-silanyloxy)-phenyl]-methanol

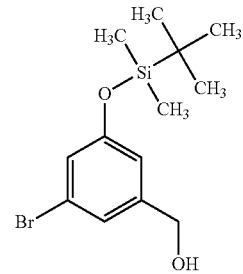 [SMILES: CC(C)(C)[Si](C)(C)Oc1cc(Br)cc(CO)c1]

3-Bromo-5-(tert-butyl-dimethyl-silanyloxy)-benzaldehyde (7 g, 22.2 mmol) was dissolved in THF and sodium borohydride (0.92 g; 24.4 mmol) was added. The reaction mixture was stirred at room temperature for 2 h and water was added, and the reaction mixture was partly evaporated to strip off THF. Ethyl acetate was added and the phases separated. The organic phase was washed with water, dried, and evaporated to dryness. Yield: 6.4 g; HPLC-MS: m/z: 317.0 (M+); Rt: 2.37 min.

Step D: {4-[3-Bromo-5-(tert-butyl-dimethyl-silanyloxy)-benzylsulfanyl]-2-methyl-phenoxy}-acetic acid ethyl ester

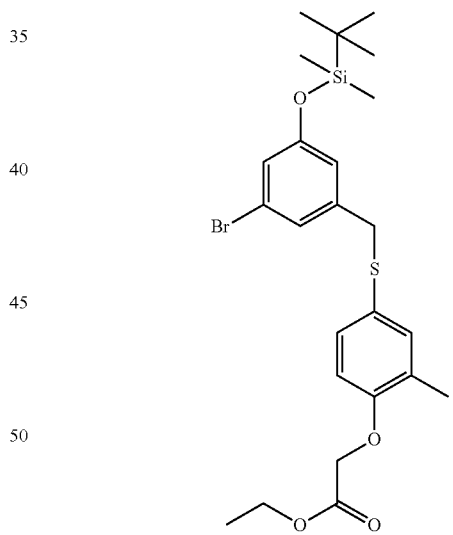

[3-Bromo-5-(tert-butyl-dimethyl-silanyloxy)-phenyl]-methanol (6.4 g; 20.17 mmol) and (4-mercapto-2-methyl-phenoxy)-acetic acid ethyl ester (5.02 g; 22.19 mmol) were dissolved in THF (200 mL). Tributylphosphine (8.15 g; 40.34 mmol) and 1,1'-(azodicarbonyl)dipiperidine (10.17 g; 40.34 mmol) were added, and the reaction mixture was stirred for 14 h at room temperature. Water and ethyl acetate were added to the reaction mixture. The phases were separated. The organic phase was washed with water, dried, and evaporated. The crude product was purified by flash chromatography (heptane:dichloromethane (1:1)). Yield: 8 g; 80%. HPLC-MS: m/z: 527.0 (M+1); Rt: 3.10 min.

Step E: [4-(3-Bromo-5-hydroxy-benzylsulfanyl)-2-methyl-phenoxy]-acetic acid ethyl ester

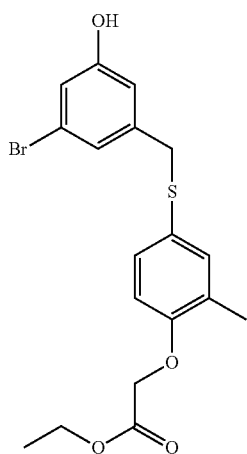 [SMILES: CCOC(=O)COc1ccc(SCc2cc(O)cc(Br)c2)cc1C]

{4-[3-Bromo-5-(tert-butyl-dimethyl-silanyloxy)-benzyl-sulfanyl]-2-methyl-phenoxy}-acetic acid ethyl ester 7 g, 13.3 mmol) was dissolved in THF under an atmosphere of nitrogen. Tetrabutylammonium fluoride 1 N in THF (15 mL) was added, and the reaction mixture was stirred at 60° C. for 2 h. Saturated sodium carbonate and water were added together with ethyl acetate, and the organic phase was separated. The organic phase was washed with water, dried, and evaporated to dryness. Yield: 3.2 g. HPLC-MS: m/z: 435.4 (M+Na); Rt: 2.22 min.

[4-(3-Bromo-5-hydroxy-phenylsulfanyl)-2-chloro-phenoxy]-acetic acid ethyl acetate

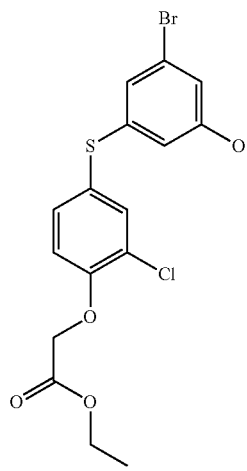 [SMILES: CCOC(=O)COc1ccc(Sc2cc(O)cc(Br)c2)cc1Cl]

(2-Chloro-4-mercapto-phenoxy)-acetic acid ethyl ester (3 g; 12.16 mmol), dibromophenol (3.67 g; 14.59 mmol), tris(dibenzylideneacetone)dipalladium (0) (0.45 g; 0.49 mmol), and 1,1'-bis-(diphenylphosphineo)ferrocenE (0.40 g; 0.73 mmol) were added to a dry reaction flask under an atmosphere of nitrogen. Triethylamine (6.74 mL, 48.64 mmol) and NMP (10 mL) were added, and the reaction mixture was stirred in a microwave oven for 1 h at 100° C. The reaction mixture was extracted with ethyl acetate, and the ethyl acetate phase was washed twice with a 5% aqueous citric acid solution. The organic phase was dried and evaporated in vacuo. The crude reaction product was purified by flash chromatography (dichloromethane→dichlormethane:ethyl acetate (1:1)). Yield 1.8 g. HPLC-MS: m/z: 441.2 (M+Na); Rt: 2.34 min.

[4-(3-Bromo-5-hydroxy-phenylsulfanyl)-2-methyl-phenoxy]-acetic acid ethyl acetate

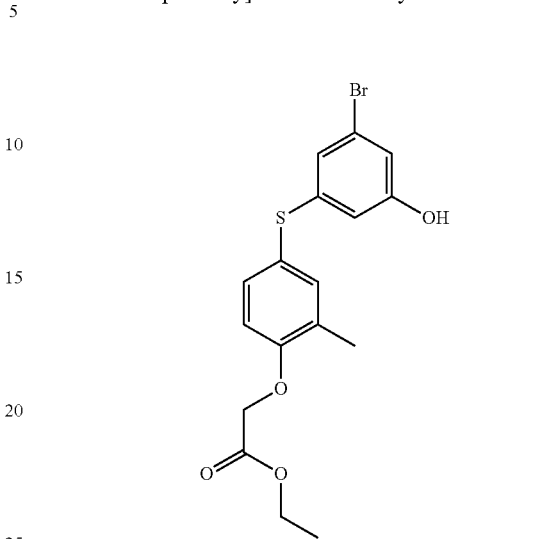

(2-Methyl-4-mercapto-phenoxy)-acetic acid ethyl ester (6 g; 26.51 mmol), dibromophenol (8.68 g; 34.47 mmol), tris(dibenzylideneacetone)dipalladium (0) (0.97 g; 1.06 mmol), and 1,1'-bis-(diphenylphosphineo)ferrocene (0.88 g; 1.59 mmol) were added to a dry reaction flask under an atmosphere of nitrogen. Triethylamine (10.73 mL, 106 mmol) and NMP (20 mL) were added, and the reaction mixture was stirred in a microwave oven for 1 h at 105° C. A 5% aqueous citric acid solution (150 mL) was added to the reaction mixture, which was extracted with ethyl acetate (4×100 mL). The pooled organic phases were washed twice with water (30 mL), dried and evaporated in vacuo. The crude reaction product was purified by flash chromatography (heptane:ethyl acetate (10:1→7:3). Yield 6.5 g. HPLC-MS: m/z: 397.3 (M+); Rt: 2.33 min.

{4-[3-Bromo-5-(3-morpholin-4-yl-propoxy)-phenyl-sulfanyl]-2-chloro-phenoxy}-acetic acid ethyl ester

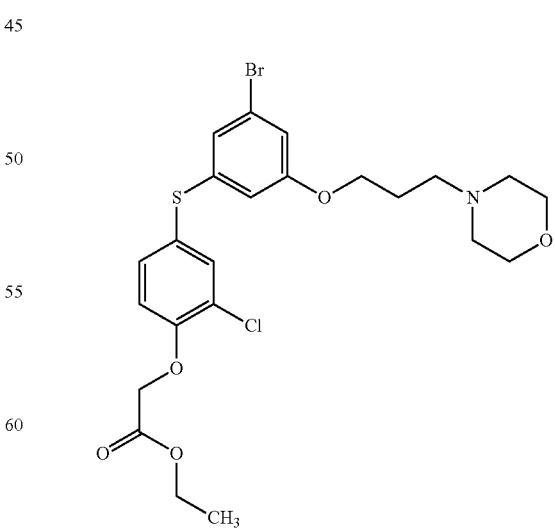

[4-(3-Bromo-5-hydroxy-phenylsulfanyl)-2-chloro-phenoxy]-acetic acid ethyl acetate (1.7 g; 4.07 mmol), N-(3- hydroxypropyl)morpholine (0.59 g; 4.07 mmol) and tributylphosphine (1.8 g; 7.33 mmol) were dissolved in THF (100 mL) in a dried reaction flask under an atmosphere of nitrogen. 1,1'-(Azodicarbonyl)dipiperidine (1.85 g; 7.33 mmol) dissolved in THF (50 mL) was added to the reaction mixture, which was stirred at room temperature for 16 h. The reaction mixture was evaporated to dryness and purified by flash chromatography (ethyl acetate:heptane). Yield: 1.1 g. HPLC-MS: m/z: 544.0 (M+); Rt: 1.78 min.

{2-Chloro-4-[3-(4-chloro-phenylethynyl)-5-hydroxy-phenylsulfanyl]-phenoxy}-acetic acid ethyl ester

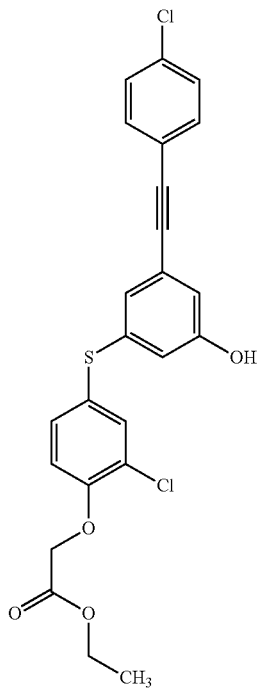 [SMILES: CCOC(=O)COc1ccc(Sc2cc(O)cc(C#Cc3ccc(Cl)cc3)c2)cc1Cl]

[4-(3-Bromo-5-hydroxy-phenylsulfanyl)-2-chloro-phenoxy]-acetic acid ethyl acetate (1.1 g; 2.63 mmol), 4-chlorophenylacetylene (1.08 g; 7.9 mmol), bis(triphenylphosphine)-palladium (II) chloride (0.15 g; 0.21 mmol) and copper iodide (0.03 g; 0.16 mmol) were dissolved in a mixture of triethylamine (5 mL) and DMF (5 mL) under an atmosphere of nitrogen. The reaction mixture was reacted in a microwave oven at 100° C. for 1 h. The reaction mixture was evaporated to dryness and portioned between 5% aqueous citric acid and ethyl acetate. The organic phase was dried and evaporated to dryness. The crude product was purified by flash chromatography (ethyl acetate:heptane 1:3). Yield: 1.1 g. HPLC-MS: m/z: 473.3 (M+); Rt: 2.76 min.

[4-(3-hydroxy-5-phenylethynyl-phenylsulfanyl)-2-methyl-phenoxy]-acetic acid ethyl ester

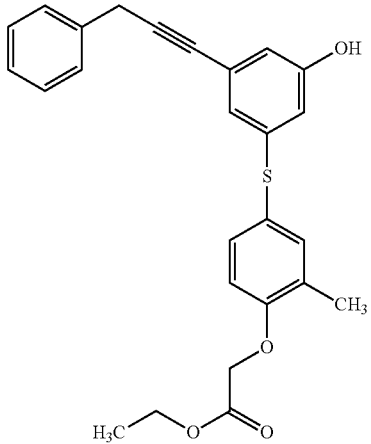 [SMILES: CCOC(=O)COc1ccc(Sc2cc(O)cc(C#CCc3ccccc3)c2)cc1C]

[4-(3-Bromo-5-hydroxy-phenylsulfanyl)-2-methyl-phenoxy]-acetic acid ethyl acetate (3 g; 7.55 mmol), 3-phenyl-1-propyn (2.63 g; 22.65 mmol), bis(triphenylphosphine)palladium (II) chloride (0.42 g; 0.60 mmol) and copper iodide (0.086 g; 0.45 mmol) were dissolved in a mixture of triethylamine (3 mL) and DMF (6 mL) under an atmosphere of nitrogen. The reaction mixture was reacted in a microwave oven at 100° C. for 11 h. The reaction mixture was evaporated to dryness, and portioned between 5% aqueous citric acid and ethyl acetate. The organic phase was dried and evaporated to dryness. The crude product was purified by preparative HPLC method A. Yield: 1.4 g. HPLC-MS: m/z: 433.3 (M+); Rt: min.

[4-(3-Hydroxy-5-phenylethynyl-phenylsulfanyl)-2-methyl-phenoxy]-acetic acid ethyl ester

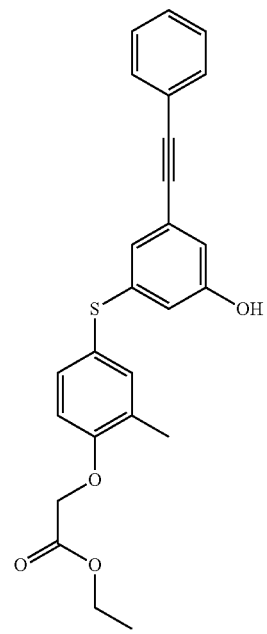 [SMILES: CCOC(=O)COc1ccc(Sc2cc(O)cc(C#Cc3ccccc3)c2)cc1C]

[4-(3-Bromo-5-hydroxy-phenylsulfanyl)-2-methyl-phenoxy]-acetic acid ethyl acetate (2.3 g; 5.79 mmol), phenylacetylene (1.9 mL; 17.4 mmol), bis(triphenylphosphine)palladium (II) chloride (0.33 g; 0.46 mmol) and copper iodide (0.07 g; 0.35 mmol) were dissolved in a mixture of triethylamine (7 mL) and DMF (8 mL) under an atmosphere of nitrogen. The reaction mixture was reacted in a microwave oven at 100° C. for 1 h. The reaction mixture was evaporated to dryness, and 5% aqueous citric acid and ethyl acetate was added. The organic phase was separated, dried and evaporated to dryness. The crude product was purified by flash chromatography (ethyl acetate:heptane 1:10→1:3). Yield: 1.2 g. HPLC-MS: m/z: 419 (M+); Rt: 2.52 min.

{4-[3-Hydroxy-5-(3-morpholin-4-yl-prop-1-ynyl)-phenylsulfanyl]-2-methyl-phenoxy}-acetic acid ethyl ester

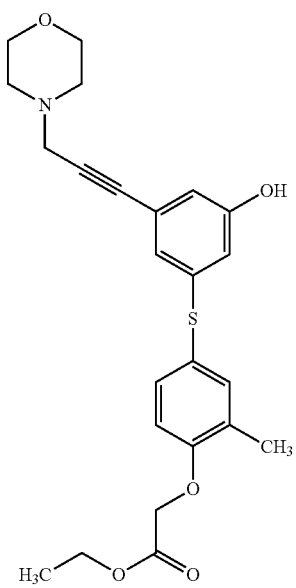 [SMILES: CCOC(=O)COc1ccc(Sc2cc(O)cc(C#CCN3CCOCC3)c2)cc1C]

[4-(3-Bromo-5-hydroxy-phenylsulfanyl)-2-methyl-phenoxy]-acetic acid ethyl acetate (3 g; 7.55 mmol), 4-prop-2-ynyl-morpholine (2.8 g; 22.65 mmol), bis(triphenylphosphine)-palladium (II) chloride (0.42 g; 0.60 mmol) and copper iodide (0.09 g; 0.45 mmol) were dissolved in a mixture of triethylamine (7 mL) and DMF (8 mL) under an atmosphere of nitrogen. The reaction mixture was reacted in a microwave oven at 100° C. for 1.5 h. The reaction mixture was purified by preparative HPLC (method A). Yield: 1.4 g. HPLC-MS: m/z: 442.4 (M+); Rt: 1.54 min.

{4-[3-Hydroxy-5-(3-morpholin-4-yl-prop-1-ynyl)-benzylsulfanyl]-2-methyl-phenoxy}-acetic acid ethyl ester

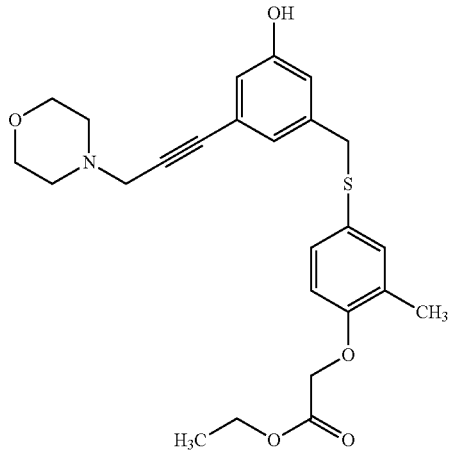 [SMILES: CCOC(=O)COc1ccc(SCc2cc(O)cc(C#CCN3CCOCC3)c2)cc1C]

[4-(3-Bromo-5-hydroxy-benzylsulfanyl)-2-methyl-phenoxy]-acetic acid ethyl ester (2.3 g; 5.6 mmol), 4-prop-2-ynyl-morpholine (2.1 g; 16.8 mmol), bis(triphenylphosphine)palladium (II) chloride (0.31 g; 0.45 mmol) and copper iodide (0.06 g; 0.34 mmol) were dissolved in a mixture of triethylamine (5 mL) and DMF (10 mL) under an atmosphere of nitrogen. The reaction mixture was reacted in a microwave oven at 100° C. for 1 h. The reaction mixture was purified by preparative HPLC (method A). Yield: 0.9 g. HPLC-MS: m/z: 456.1 (M+); Rt: 1.53 min.

{4-[3-Hydroxy-5-(3-phenyl-prop-1-ynyl)-benzylsulfanyl]-2-methyl-phenoxy}-acetic acid ethyl ester

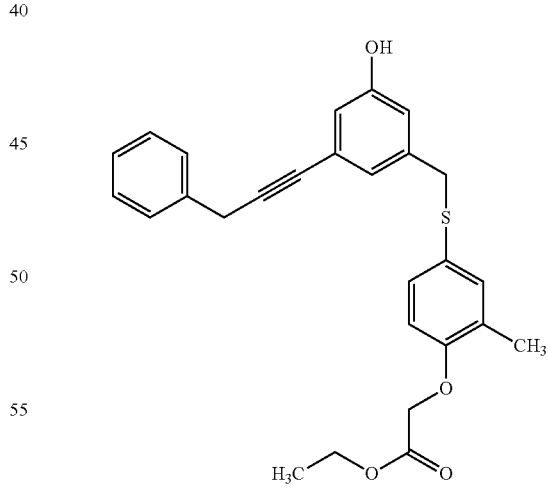

[4-(3-Bromo-5-hydroxy-benzylsulfanyl)-2-methyl-phenoxy]-acetic acid ethyl ester (2 g; 4.9 mmol), 3-phenyl-1-propyn (1.7 g; 14.6 mmol), bis(triphenylphosphine)palladium (II) chloride (0.27 g; 0.39 mmol) and copper iodide (0.056 g; 0.29 mmol) were dissolved in a mixture of triethylamine (5 mL) and DMF (10 mL) under an atmosphere of nitrogen. The reaction mixture was reacted in a microwave oven at 100° C. for 1 h. Further 3-phenyl-1-propyn (1.7 g;

14.6 mmol) was added and the reaction mixture was reacted in a microwave oven at 100° C. for further 1 h. The reaction mixture was purified by preparative HPLC (method A). Yield: 0.8 g. HPLC-MS: m/z: 434.6 (M+1); Rt: 2.43 min.

{4-[3-Bromo-5-cyclohexylmethoxy-phenylsulfanyl)-2-methyl-phenoxy]-acetic acid ethyl ester

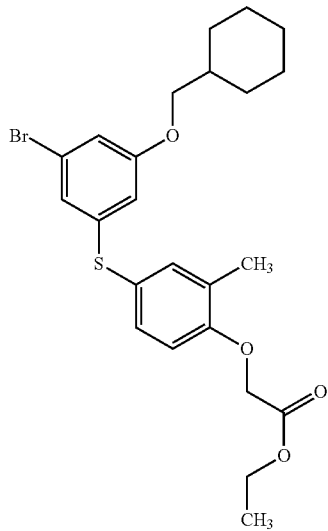 [SMILES: CCOC(=O)COc1ccc(Sc2cc(Br)cc(OCC3CCCCC3)c2)cc1C]

[4-(3-Bromo-5-hydroxy-phenylsulfanyl)-2-methyl-phenoxy]-acetic acid ethyl acetate ester (0.23 g; 0.58 mmol), cyclohexyl-methanol (80 μl; 0.64 mmol) and tributylphosphine (0.21 mL; 0.87 mmol) were dissolved in THF (10 mL) in a dried reaction flask under an atmosphere of nitrogen. 1,1'-(Azodicarbonyl)dipiperidine (0.22 g; 0.87 mmol) dissolved in THF (10 mL) was added to the reaction mixture, which was stirred at room temperature for 2 days. The reaction mixture was filtered, evaporated to dryness and purified by flash chromatography (ethyl acetate:heptane 1:1). Yield: 100 mg. HPLC-MS: m/z: 493.4 (M)+; Rt: 3.17 min.

{4-[3-Bromo-5-cyclopentylmethoxy-phenylsulfanyl)-2-methyl-phenoxy]-acetic acid ethyl ester

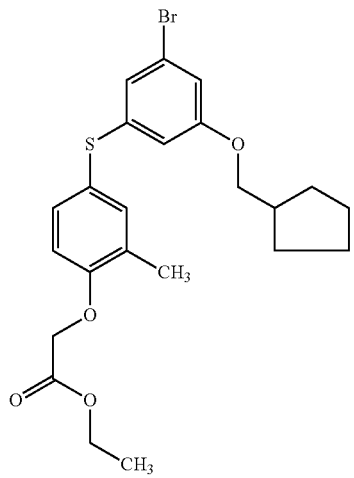 [SMILES: CCOC(=O)COc1ccc(Sc2cc(Br)cc(OCC3CCCC3)c2)cc1C]

1,3-Dibromo-5-cyclopentylmethoxy-benzene 3,5-Dibromophenol (5.0 g; 19.8 mmol), cyclopentane-methanol (2.0 g; 19.9 mmol) and tributylphosphine (8.8 mL; 35.7 mmol) were dissolved in dry THF (250 mL) in a dried reaction flask under an atmosphere of nitrogen. 1,1'-(Azodicarbonyl)dipiperidine (9.01 g; 35.7 mmol) dissolved in dry THF (150 mL) was added to the reaction mixture, which was stirred at room temperature for 16 hours. The reaction mixture was filtered, evaporated to dryness and purified by flash chromatography (heptane→ethyl acetate:heptane 2:3). Yield: 5.68 g; 86%.

[4-(3-Bromo-5-cyclopentylmethoxy-phenylsulfanyl)-2-methyl-phenoxy]-acetic acid ethyl ester 1,3-Dibromo-5-cyclopentylmethoxy-benzene (2.9 g; 8.6 mmol), (4-Mercapto-2-methyl-phenoxy)-acetic acid ethyl ester (1.5 g; 6.6 mmol), tris(dibenzylideneacetone)dipalladium(0) (0.18 g, 0.20 mmol) and 1,1'-bis(diphenylphosphino)-ferrocen (0.22 g; 0.40 mmol) was added to a dried microwave flask under an atmosphere of nitrogene. The reaction flask was sealed and dry NMP (10 mL) and TEA (3.7 mL; 26.5 mmol) was added through the septum. The reaction flask was reacted in a microwave oven at 140° C. for 1 h. Ethyl acetate (30 mL) and aqueous 5% citric acid (30 mL) was added to the reaction mixture and the phases were separated. The aqueous phase was extracted with ethyl acetate (30 mL×2) and the pooled organic phases were dried (MgSO$_4$) and evaporated to dryness. The reaction mixture was purified by flash chromatography (heptane→heptane: ethyl acetate (9:1½). Yield: 1.45 g (46%). HPLC-MS: m/z: 479.8 (M)+; Rt: 3.18 min.

{4-[3-Bromo-5-isobutoxy-phenylsulfanyl)-2-methyl-phenoxy]-acetic acid ethyl ester

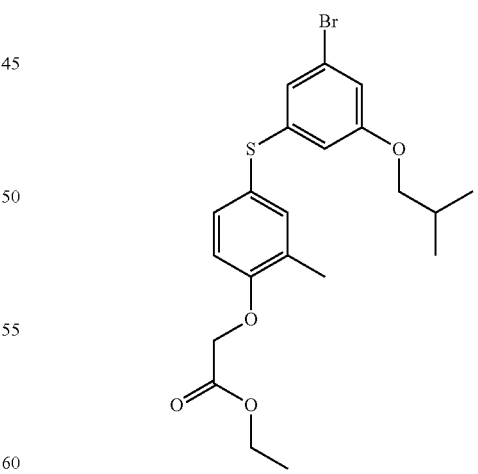

{4-[3-Bromo-5-isobutoxy-phenylsulfanyl)-2-methyl-phenoxy]-acetic acid ethyl ester was prepared as described for {4-[3-Bromo-5-cyclopentylmethoxy-phenylsulfanyl)-2-methyl-phenoxy]-acetic acid ethyl ester. Yield: 45%. HPLC-MS: m/z: 454.8 (M+H)+; Rt: 3.07 min.

49

(4-{3-Bromo-5-[2-(4-chloro-phenyl)-ethoxy]-phenylsulfanyl}-2-methyl-phenoxy)-acetic acid ethyl ester

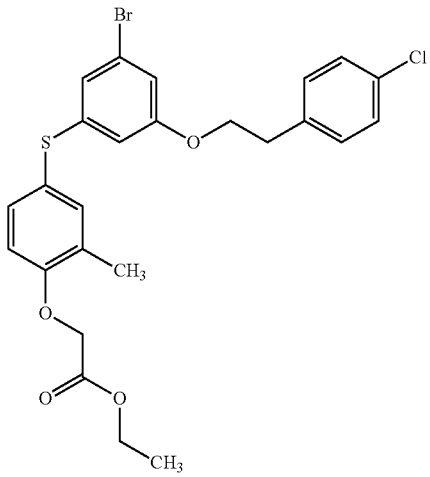 [SMILES: CCOC(=O)COc1ccc(Sc2cc(Br)cc(OCCc3ccc(Cl)cc3)c2)cc1C]

(4-{3-Bromo-5-[2-(4-chloro-phenyl)-ethoxy]-phenylsulfanyl}-2-methyl-phenoxy)-acetic acid ethyl ester was prepared as described for {4-[3-Bromo-5-cyclopentylmethoxy-phenylsulfanyl)-2-methyl-phenoxy]-acetic acid ethyl ester. Yield: 25%. HPLC-MS: m/z: 537.1 (M+2); Rt: 3.11 min.

{4-[3-Bromo-5-(2-ethyl-butoxy)-phenylsulfanyl]-2-methyl-phenoxy}-acetic acid ethyl ester

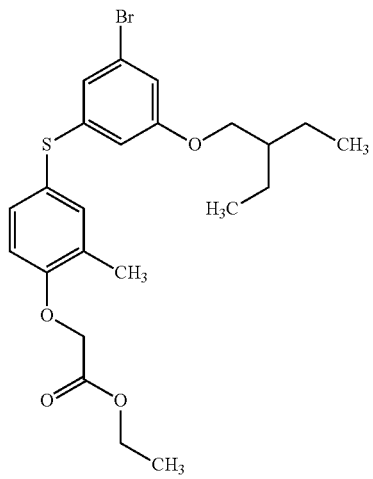 [SMILES: CCOC(=O)COc1ccc(Sc2cc(Br)cc(OCC(CC)CC)c2)cc1C]

{4-[3-Bromo-5-(2-ethyl-butoxy)-phenylsulfanyl]-2-methyl-phenoxy}-acetic acid ethyl ester was prepared as described for {4-[3-Bromo-5-cyclopentylmethoxy-phenylsulfanyl)-2-methyl-phenoxy]-acetic acid ethyl ester. Yield: 63%. HPLC-MS: m/z: 481.0 (M)$^+$; Rt: 3.20 min.

50

[4-(3-Bromo-5-cyclopentyloxy-phenylsulfanyl)-2-methyl-phenoxy]-acetic acid ethyl ester

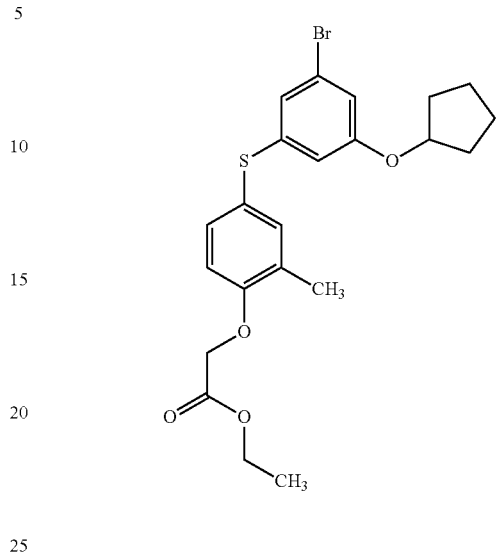

[4-(3-Bromo-5-cyclopentyloxy-phenylsulfanyl)-2-methyl-phenoxy]-acetic acid ethyl ester was prepared as described for {4-[3-Bromo-5-cyclopentylmethoxy-phenylsulfanyl)-2-methyl-phenoxy]-acetic acid ethyl ester. Yield: 51%. HPLC-MS: m/z: 565.0 (M)$^+$; Rt: 3.04 min.

{4-[3-Bromo-5-(4-methanesulfonyl-benzyloxy)-phenylsulfanyl]-2-methyl-phenoxy}-acetic acid ethyl ester

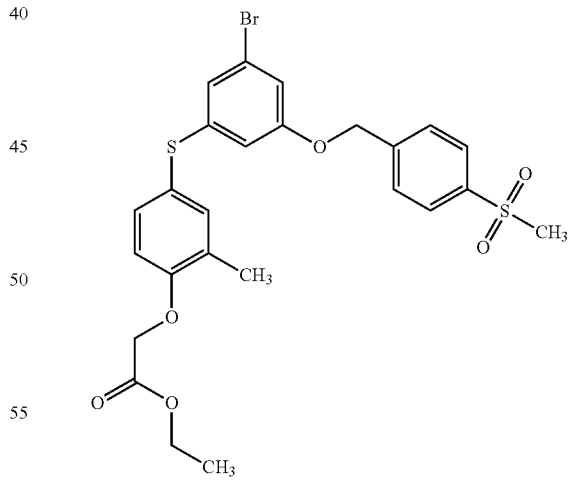

{4-[3-Bromo-5-(4-methanesulfonyl-benzyloxy)-phenylsulfanyl]-2-methyl-phenoxy}-acetic acid ethyl ester was prepared as described for {4-[3-Bromo-5-cyclopentylmethoxy-phenylsulfanyl)-2-methyl-phenoxy]-acetic acid ethyl ester. Yield: 9%. HPLC-MS: m/z: 565.2 (M)$^+$; Rt: 2.58 min.

{4-[3-Bromo-5-(2-cyclohexyl-ethoxy)-phenylsulfanyl]-2-methyl-phenoxy}-acetic acid ethyl ester

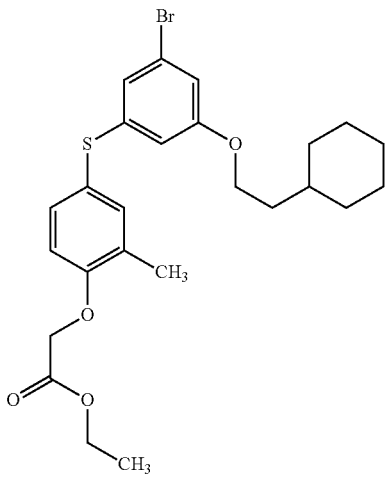 [SMILES: CCOC(=O)COc1ccc(Sc2cc(Br)cc(OCCC3CCCCC3)c2)cc1C]

{4-[3-Bromo-5-(2-cyclohexyl-ethoxy)-phenylsulfanyl]-2-methyl-phenoxy}-acetic acid ethyl ester was prepared as described for {4-[3-Bromo-5-cyclopentylmethoxy-phenylsulfanyl)-2-methyl-phenoxy]-acetic acid ethyl ester. Yield: 51%. HPLC-MS: m/z: 508.8 (M+H)+; Rt: 3.33 min.

{4-[3-Bromo-5-(3-trifluoromethyl-pyridin-2-yloxy)-phenylsulfanyl]-2-methyl-phenoxy}-acetic acid ethyl ester

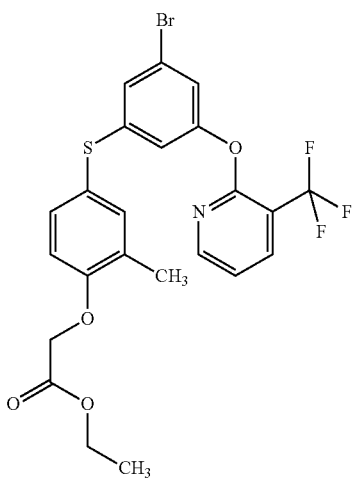 [SMILES: CCOC(=O)COc1ccc(Sc2cc(Br)cc(Oc3ncccc3C(F)(F)F)c2)cc1C]

2-(3,5-Dibromo-phenoxy)-3-trifluoromethyl-pyridine 3,5-Dibromophenol (2.0 g; 7.9 mmol), 2-chloro-3-trifluoropyridine (1.4 g; 7.9 mmol), potassium hydroxide (0.45 g; 7.9 mmol) and DMSO (40 mL) was added to a reaction flask under an atmosphere of nitrogen. The reaction mixture was reacted at 110° C. for 6 h. The reaction mixture was cooled to room temperature and ethyl acetate (30 ml) and water (120 mL) was added. The organic phase was separated form the aqueous phase and the aqueous phase was extracted with ethyl acetate (30 mL×4). The combined organic phases were dried, evaporated to dryness and purified by flash chromatography (heptane→ethyl acetate:heptane 1:8). Yield: 2.23 g; 71%. HPLC-MS: m/z: 397.9 (M)+; Rt: 2.58 min.

{4-[3-Bromo-5-(3-trifluoromethyl-pyridin-2-yloxy)-phenylsulfanyl]-2-methyl-phenoxy}-acetic acid ethyl ester 2-(3,5-Dibromo-phenoxy)-3-trifluoromethyl-pyridine (2.05 g; 5.17 mmol) and (4-Mercapto-2-methyl-phenoxy)-acetic acid ethyl ester (0.9 g; 4.0 mmol) was condensed to give the title product applying the procedure described for {4-[3-Bromo-5-cyclopentylmethoxy-phenylsulfanyl)-2-methyl-phenoxy]-acetic acid ethyl ester. The crude product was purified by flash chromatography (heptane→ethyl acetate:heptane 2:9). Yield 1.26 g (58%). HPLC-MS: m/z: 544.3 (M+2); Rt: 2.77 min.

{4-[3-Bromo-5-(5-trifluoromethyl-pyridin-2-yloxy)-phenylsulfanyl]-2-methyl-phenoxy}-acetic acid ethyl ester

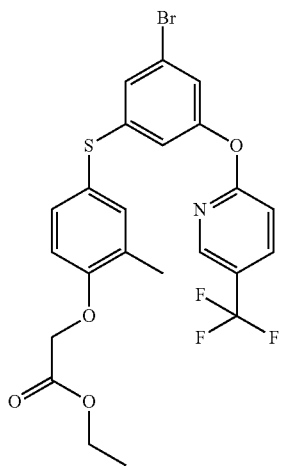 [SMILES: CCOC(=O)COc1ccc(Sc2cc(Br)cc(Oc3ccc(C(F)(F)F)cn3)c2)cc1C]

2-(3,5-Dibromo-phenoxy)-5-trifluoromethyl-pyridine

The title product was prepared as described for 2-(3,5-Dibromo-phenoxy)-3-trifluoro-methyl-pyridine Yield: 70%; HPLC-MS: m/z: 397.7 (M)+; Rt 2.60 min.

{4-[3-Bromo-5-(5-trifluoromethyl-pyridin-2-yloxy)-phenylsulfanyl]-2-methyl-phenoxy}-acetic acid ethyl ester 2-(3,5-Dibromo-phenoxy)-5-trifluoromethyl-pyridine (2.5 g; 6.3 mmol) and (4-Mercapto-2-methyl-phenoxy)-acetic acid ethyl ester (1.1 g; 4.9 mmol) was condensed to give the title product applying the procedure described for {4-[3-Bromo-5-cyclopentylmethoxy-phenylsulfanyl)-2-methyl-phenoxy]-acetic acid ethyl ester. The crude product was purified by flash chromatography (heptane→ethyl acetate: heptane 2:9). Yield 1.4 g (53%). HPLC-MS: m/z: 544.3 (M+2); Rt: 2.80 min.

{4-[3-Bromo-5-(3-trifluoromethyl-phenoxy)-phenyl-sulfanyl]-2-methyl-phenoxy}-acetic acid ethyl ester

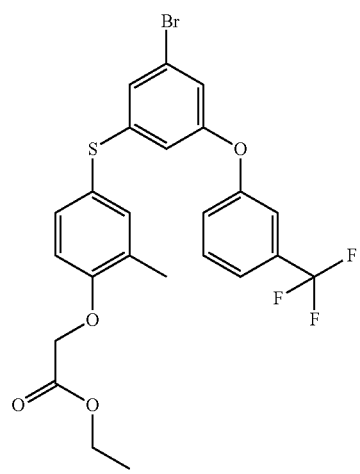 [SMILES: CCOC(=O)COc1ccc(Sc2cc(Br)cc(Oc3cccc(C(F)(F)F)c3)c2)cc1C]

1,3-Dibromo-5-(3-trifluoromethyl-phenoxy)-benzene 3,5-Dibromophenol (4.1 g; 16.2 mmol), 3-(trifluoromethyl)-phenylboronic acid (6.2 g; 32.4 mmol), Cu(II) acetate (2.9 g; 16.2 mmol), TEA (5.6 mL; 40.5 mmol) and dichloromethane (150 mL) and molecular sieves (2 ml) was added to a reaction flask the reaction mixture was stirred for 7 days. Further 3-(trifluoromethyl)-phenylboronic acid (6.2 g; 32.4 mmol) was added and the reaction mixture stirred for 1 day. Further 3-(trifluoromethyl)-phenylboronic acid (6.2 g; 32.4 mmol) and TEA (5.6 mL; 40.5 mmol) was added and the reaction mixture stirred for 1 day. 5% Aqueous citric acid (150 mL) was added and the two phases were separated. The aqueous phase was extracted with dichloromethane (50 mL×2) and the organic phases were pooled, dried and evaporated to dryness. The crude product purified by flash chromatography (heptane→ethyl acetate:heptane 1:9). Yield: 1.86 g; HPLC-MS: m/z: 397. (M+H)+; Rt: 2.78 min.

{4-[3-Bromo-5-(3-trifluoromethyl-phenoxy)-phenyl-sulfanyl]-2-methyl-phenoxy}-acetic acid ethyl ester 1,3-Dibromo-5-(3-trifluoromethyl-phenoxy)-benzene (1.35 g; 3.4 mmol) and (4-Mercapto-2-methyl-phenoxy)-acetic acid ethyl ester (0.7 g; 3.1 mmol) was condensed to give the title product applying the procedure described for {4-[3-Bromo-5-cyclopentylmethoxy-phenylsulfanyl)-2-methyl-phenoxy]-acetic acid ethyl ester. The crude product was purified by preparative HPLC (Method A) followed by flash chromatography (dichloromethane:heptane 3:7). Yield 0.5 g. HPLC-MS: m/z: 541.3 (M)+; Rt: 3.03 min.

[4-(3-Bromo-5-cyclopropylmethoxy-benzylsulfanyl)-2-methyl-phenoxy]-acetic acid ethyl ester

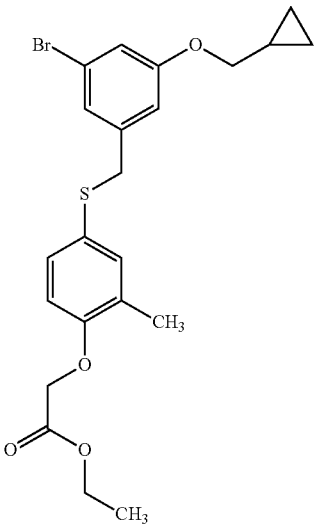 [SMILES: CCOC(=O)COc1ccc(SCc2cc(Br)cc(OCC3CC3)c2)cc1C]

[4-(3-Bromo-5-hydroxy-benzylsulfanyl)-2-methyl-phenoxy]-acetic acid ethyl ester (1.0 g; 2.43 mmol), cyclopropylcarbinol (175 mg; 2.43 mmol) and tributylphosphine (1.07 mL; 4.38 mmol) was dissolved in THF (100 mL) in a dried reaction flask under an atmosphere of nitrogen. 1,1'-(Azodicarbonyl)dipiperidine (1.1 g; 4.38 mmol) dissolved in THF (20 mL) was added to the reaction mixture, which was stirred at room temperature for 16 hours. The reaction mixture was filtered, evaporated to dryness and purified by flash chromatography (ethyl acetate:heptane 1:9→2:3). Yield: 980 mg; 86%; HPLC-MS: m/z: 465.0 (M)+; Rt: 2.74 min.

[4-(3-Bromo-5-cyclopropylmethoxy-phenylsulfanyl)-2-methyl-phenoxy]-acetic acid ethyl ester

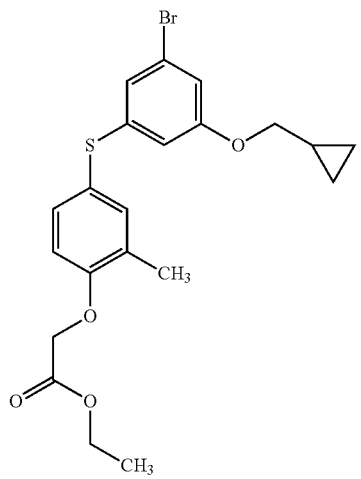 [SMILES: CCOC(=O)COc1ccc(Sc2cc(Br)cc(OCC3CC3)c2)cc1C]

Step A:
1,3-Dibromo-5-cyclopropylmethoxy-benzene 3,5-Dibromo-phenol (5 g; 19.9 mmol), cyclopropylcarbinol (1.4 g; 19.9 mmol) and tributylphosphine (8.8 mL;

35.7 mmol) were dissolved in THF (500 mL) in a dried reaction flask under an atmosphere of nitrogen. 1,1'-(Azodicarbonyl)dipiperidine (9.0 g; 35.7 mmol) dissolved in THF (100 mL) was added to the reaction mixture, which was stirred at room temperature for 16 hours. The reaction mixture was partly evaporated, filtered, evaporated to dryness and purified by flash chromatography (ethyl acetate:heptane 0:1→1:10). Yield: 5.45 g; 90%.

Step B: [4-(3-Bromo-5-cyclopropylmethoxy-phenylsulfanyl)-2-methyl-phenoxy]-acetic acid ethyl ester 1,3-Dibromo-5-cyclopropylmethoxy-benzene (5.27 g; 17.23 mmol), (4-Mercapto-2-methyl-phenoxy)-acetic acid ethyl ester (3 g; 13.26 mmol), tris(dibenzylideneacetone)dipalladium (0) (0.36 g; 0.40 mmol), and 1,1'-bis-(diphenylphosphineo)ferrocene (0.44 g; 0.80 mmol) was added to a dry reaction flask under an atmosphere of nitrogen. Triethylamine (7.45 mL) and NMP (8 mL) was added, and the reaction mixture was stirred in a microwave oven for 1 h at 140° C. A 5% aqueous citric acid solution (150 mL) was added to the reaction mixture, which was extracted with ethyl acetate (4×100 mL). The pooled organic phases were dried and evaporated in vacuo. The crude reaction product was purified by flash chromatography (heptane: ethyl acetate (20:1→7:3). Yield 2.8 g; 47%). HPLC-MS: m/z: 451.0 (M+); Rt: 2.85 min

[4-(3-Bromo-5-isobutoxy-phenylsulfanyl)-2,5-dimethyl-phenoxy]-acetic acid ethyl ester

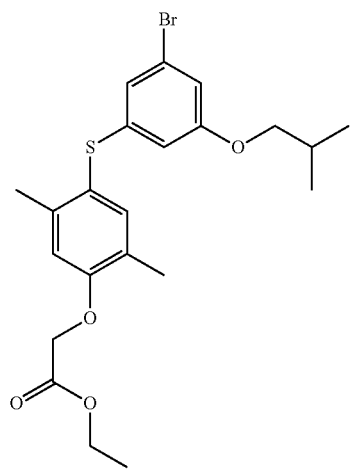 [SMILES: CCOC(=O)COc1cc(C)c(Sc2cc(Br)cc(OCC(C)C)c2)cc1C]

Step A1: 1,3-Dibromo-5-isobutoxy-benzene

Potassium hydroxide (15.9 g; 284 mmol) was dissolved in water (300 ml) and 3,5-dibromo-phenol (47 g; 188.5 mmol) was added. Benzyl tributylammoniumchloride (17.7 g; 56.8 mmol) and toluene (200 ml) was added and the reaction mixture was heated to 85° C. Bromoethylpropan (32.3 g; 325.7 mmol) was added over 5 hours and the reaction mixture was stirred at 85° C. for additional 16 h. The reaction mixture was cooled to room temperature and the phases were separated. Toluene (100 ml) was added to the organic phase which was washed with 0.2 N aqueous HCl (200 ml×2) and water (200 ml×2). The organic phase was evaporated to give the crude product which was purified by distillation (0.7.mm Hg; Bp: 98° C.); Yield: 43 g (colourless oil).

Step A2: (4-Mercapto-2,5-dimethyl-phenoxy)-acetic acid ethyl ester (4-Mercapto-2,5-dimethyl-phenoxy)-acetic acid ethyl ester was prepared as described for 2,6-difluoro-4-mercapto-phenoxy)acetic acid methyl ester (compound 21) in Eur. J. Med. Chem., 1995, 30, 403 (Kawashima, M. S.) except that (4-chlorosulfonyl-2,5-dimethyl-phenoxy)acetic acid ethyl ester was reduced with 4 eq. of zn (dust) in a mixture of konc. sulfuric acid and ethanol at 80° C.

Step B: [4-(3-Bromo-5-isobutoxy-phenylsulfanyl)-2,5-dimethyl-phenoxy]-acetic acid ethyl ester 1,3-Dibromo-5-isobutoxy-benzene (1.66 g; 5.4 mmol), (4-Mercapto-2,5-dimethyl-phenoxy)-acetic acid ethyl ester (1.0 g; 4.1 mmol), tris(dibenzylideneacetone)dipalladium (0) (0.11 g; 0.12 mmol), and 1,1'-bis-(diphenylphosphineo)ferrocene (0.14 g; 0.25 mmol) were added to a dry reaction flask under an atmosphere of nitrogen. Triethylamine (2.3 mL) and NMP (10 mL) was added, and the reaction mixture was stirred in a microwave oven for 1 h at 140° C. A 5% aqueous citric acid solution (150 mL) was added to the reaction mixture, which was extracted with ethyl acetate (4×100 mL). The pooled organic phases were dried and evaporated in vacuo. The crude reaction product was purified by flash chromatography (heptane: ethyl acetate (10:1→1:1). Yield: 1.3 g; 67%. HPLC-MS: m/z: 467.0 (M+); Rt: 3.10 min

[4-(3-Bromo-5-isobutoxy-phenoxy)-2-methyl-phenoxy]-acetic acid methyl ester

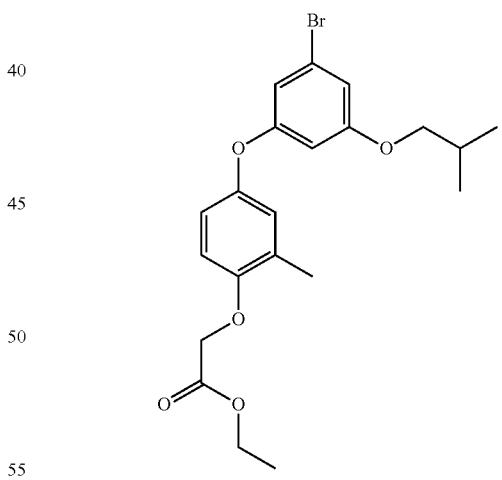

Step A: 3-Bromo-5-isobutoxy-phenylboronic acid 1,3-Dibromo-5-isobutoxy-benzene (1. g; 3.3 mmol) was dissolved in dry THF (30 ml) in a dry reaction under stirring. The reaction mixture was cooled to −70° C. and n-BuLi (2M; 2.44 ml) was added. The reaction mixture was stirred for 15 min. and triisobutylborate (1.50 ml; 6.5 mmol) was added at −70° C. The temperature was raised to −30° C. and stirred for 1½ hour followed by a temperature increase to room temperature. The reaction mixture was quenched with saturated aqueous sodium hydrogen carbonate (about 3 ml) and evaporated to dryness. The crude product was purified by prep HPLC (method B). Yield: 430 mg; 49%. HPLC-MS: m/z: 272.9 (M+); Rt: 2.08 min Step B: [4-(3-Bromo-5-isobutoxy-phenoxy)-2-methyl-phenoxy]-acetic acid methyl ester (4-Hydroxy-2-methyl-phenoxy)-acetic acid methyl ester (215 mg; 1.1 mmol), 3-Bromo-5-isobutoxy-phenylboronic acid (523.4; 1.9 mmol), copper(II) acetate (199 mg; 1.1 mmol), crushed molsieves (about 1 g) and triethylamine (0.46 ml; 3.3 mmol) was dissolved in dichloromethane (40 ml) and stirred over night. The reaction mixture was filtered through celite and evaporated to dryness. The crude product was purified by preparative HPLC (method B). Yield: 300 mg; 65%. HPLC-MS: m/z: 423.5 (M+); Rt: 2.71 min Example 1

{2-Chloro-4-[3-(4-chloro-phenylethynyl)-5-(3-piperidin-1-yl-propoxy)-phenylsulfanyl]-phenoxy}-acetic acid

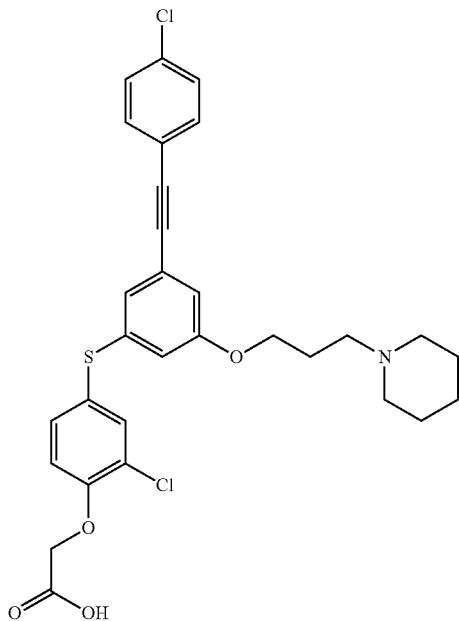

Step A: {2-Chloro-4-[3-(4-chloro-phenylethynyl)-5-(3-piperidin-1-yl-propoxy)-phenylsulfanyl]-phenoxy}-acetic acid ethyl ester

[{2-Chloro-4-[3-(4-chloro-phenylethynyl)-5-hydroxy-phenylsulfanyl]-phenoxy}-acetic acid ethyl ester (0.4 g; 0.85 mmol), 3-piperidin-1-yl-propan-1-ol (0.12 g; 0.85 mmol) and tributylphosphine (0.37 mL; 1.5 mmol) were dissolved in THF (50 mL) in a dried reaction flask under an atmosphere of nitrogen. 1,1'-(Azodicarbonyl)dipiperidine (0.38 g; 1.5 mmol) dissolved in THF (25 mL) was added to the reaction mixture, which was stirred at room temperature for 16 h. The reaction mixture was evaporated to dryness and 5% aqueous citric acid and ethyl acetate was added. The organic phase was separated, dried, evaporated to dryness, and purified by prep HPLC (method A). Yield: 275 mg. HPLC-MS: m/z: 598.0 (M+); Rt: 2.3 min.

Step B: {2-Chloro-4-[3-(4-chloro-phenylethynyl)-5-(3-piperidin-1-yl-propoxy)-phenylsulfanyl]-phenoxy}-acetic acid {2-Chloro-4-[3-(4-chloro-phenylethynyl)-5-(3-piperidin-1-yl-propoxy)-phenylsulfanyl]-phenoxy}-acetic acid ethyl ester (275 mg; 0.46 mmol) was dissolved in ethanol (15 mL) and aqueous 1N sodium hydroxide (3 mL) was added. The reaction mixture was stirred for 16 h, acidified with 5% aqueous citric acid, and extracted with ethyl acetate. The organic phase was dried and evaporated to dryness. Yield: 200 mg. HPLC-MS: m/z: 570.0 (M+); Rt: 2.07 min.

Example 2

{2-Methyl-4-[3-(3-morpholin-4-yl-propoxy)-5-phenylethynyl-phenylsulfanyl]-phenoxy}-acetic acid

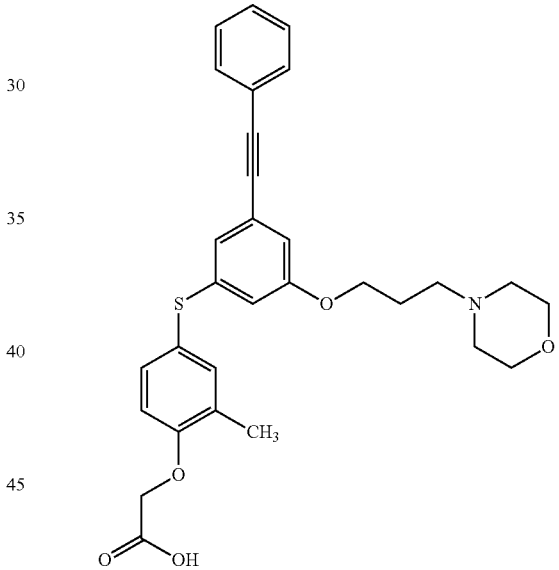

Step A: {2-Methyl-4-[3-(3-morpholin-4-yl-propoxy)-5-phenylethynyl-phenylsulfanyl]-phenoxy}-acetic acid ethyl ester

[4-(3-Hydroxy-5-phenylethynyl-phenylsulfanyl)-2-methyl-phenoxy]-acetic acid ethyl ester (0.25 g; 0.60 mmol), 3-morpholin-4-yl-propan-1-ol (0.12 g; 0.84 mmol) and tributylphosphine (0.27 mL; 1.08 mmol) were dissolved in THF (20 mL) in a dried reaction flask under an atmosphere of nitrogen. 1,1'-(Azodicarbonyl)dipiperidine (0.27 g; 1.08 mmol) dissolved in THF (10 mL) was added to the reaction mixture, which was stirred at room temperature for 16 h. The reaction mixture was evaporated to dryness, acetonitrile added, and the mixture filtered. The solution was purified by prep HPLC (method A). Yield: 150 mg. HPLC-MS: m/z: 546.6 (M+H); Rt: 2.08 min.

Step B: {2-Methyl-4-[3-(3-morpholin-4-yl-propoxy)-5-phenylethynyl-phenylsulfanyl]-phenoxy}-acetic acid {2-Methyl-4-[3-(3-morpholin-4-yl-propoxy)-5-phenylethynyl-phenylsulfanyl]-phenoxy}-acetic acid ethyl ester (150 mg; 0.28 mmol) was dissolved in ethanol (15 mL), and aqueous 1N sodium hydroxide (3 mL) was added. The reaction mixture was stirred for 16 h, acidified with 1N aqueous hydrochloric acid, and extracted with ethyl acetate. The organic phase was dried and evaporated to dryness. Yield: 110 mg. HPLC-MS: m/z: 518.1 (M+H); Rt: 1.86 min.

Example 3

{2-Chloro-4-[3-(4-chloro-phenylethynyl)-5-(3-morpholin-4-yl-propoxy)-phenyl-sulfanyl]-phenoxy}-acetic acid

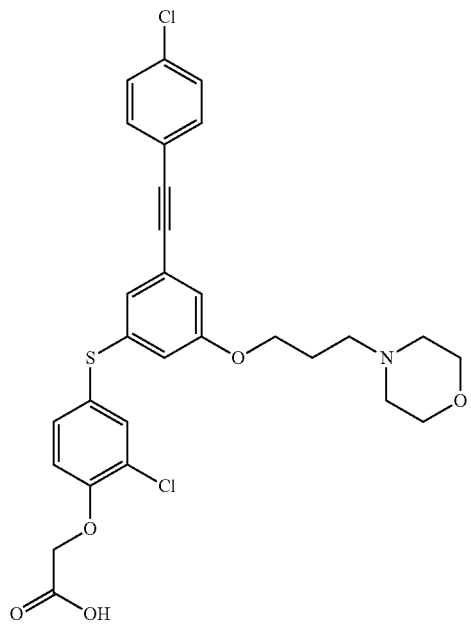 [SMILES: O=C(O)COc1ccc(Sc2cc(C#Cc3ccc(Cl)cc3)cc(OCCCN3CCOCC3)c2)cc1Cl]

Step A: {2-Chloro-4-[3-(4-chloro-phenylethynyl)-5-(3-morpholin-4-yl-propoxy)-phenylsulfanyl]-phenoxy}-acetic acid ethyl ester

[{2-Chloro-4-[3-(4-chloro-phenylethynyl)-5-hydroxy-phenylsulfanyl]-phenoxy}-acetic acid ethyl ester (293 mg; 0.62 mmol) was dissolved in THF (15 mL) in a dried reaction flask under an atmosphere of nitrogen. 3-morpholin-4-yl-propan-1-ol (75 mg; 0.52 mmol) and tributyl-phosphine (0.23 mL; 0.93 mmol) was added followed by 1,1'-(Azodicarbonyl)dipiperidine (0.38 g; 1.5 mmol) dissolved in THF (10 mL). The reaction mixture was stirred at room temperature for 16 h, filtered and evaporated in vacuo. The crude product was purified by prep. HPLC (method B). Yield: 200 mg. HPLC-MS: m/z: 600.4 (M+); Rt: 2.2 min.

Step B: {2-Chloro-4-[3-(4-chloro-phenylethynyl)-5-(3-morpholin-4-yl-propoxy)-phenylsulfanyl]-phenoxy}-acetic acid {2-Chloro-4-[3-(4-chloro-phenylethynyl)-5-(3-morpholin-4-yl-propyl-sulfanyl]-phenoxy}-acetic acid ethyl ester (200 mg; 0.33 mmol) was dissolved in ethanol (10 mL), and aqueous 1N sodium hydroxide (3 mL) was added. The reaction mixture was stirred for 16 h, acidified with 1N aqueous hydrochloric acid, and extracted with ethyl acetate. The organic phase was dried, evaporated to dryness, and purified by prep. HPLC (method A). Yield: 46 mg. HPLC-MS: m/z: 572.3 (M+); Rt: 2.03 min.

Example 4

{2-Chloro-4-[3-(4-chloro-phenylethynyl)-5-(4-morpholin-4-ylmethyl-benzyloxy)-phenylsulfanyl]-phenoxy}-acetic acid

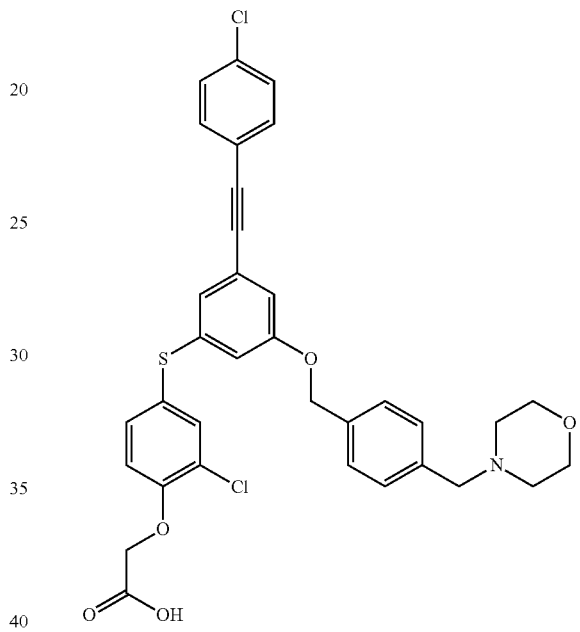

Step A: {2-Chloro-4-[3-(4-chloro-phenylethynyl)-5-(4-morpholin-4-ylmethyl-benzyloxy)-phenylsulfanyl]-phenoxy}-acetic acid ethyl ester {2-Chloro-4-[3-(4-chloro-phenylethynyl)-5-hydroxy-phenylsulfanyl]-phenoxy}-acetic acid ethyl ester (274 mg; 0.58 mmol) was dissolved in THF (15 mL) in a dried reaction flask under an atmosphere of nitrogen. (4-Morpholin-4-ylmethyl-phenyl)-methanol (100 mg; 0.48 mmol) and tributylphosphine (0.21 mL; 0.87 mmol) was added followed by 1,1'-(Azodicarbonyl)dipiperidine (0.22 g; 0.87 mmol) dissolved in THF (10 mL). The reaction mixture was stirred at room temperature for 5 h, filtered and evaporated in vacuo. The crude product was purified by prep. HPLC (method A). Yield: 250 mg. HPLC-MS: m/z: 663.0 (M+H); Rt: 2.47 min.

Step B: {2-Chloro-4-[3-(4-chloro-phenylethynyl)-5-(4-morpholin-4-ylmethyl-benzyloxy)-phenylsulfanyl]-phenoxy}-acetic acid {2-Chloro-4-[3-(4-chloro-phenylethynyl)-5-(4-morpholin-4-ylmethyl-benzyloxy)-phenylsulfanyl]-phenoxy}-acetic acid ethyl ester (250 mg; 0.38 mmol) was dissolved in ethanol (10 mL), and aqueous 1N sodium hydroxide (5 mL) was added. The reaction mixture was stirred for 16 h, acidified with 1N aqueous hydrochloric acid, and extracted with ethyl acetate. The organic phase was dried, evaporated to dryness and purified by prep. HPLC (method A). Yield: 32 mg. HPLC-MS: m/z: 634.5 (M+); Rt: 2.21 min.

Example 5

{2-Chloro-4-[3-(4-chloro-phenylethynyl)-5-(1-methyl-piperidin-4-ylmethoxy)-phenylsulfanyl]-phenoxy}-acetic acid

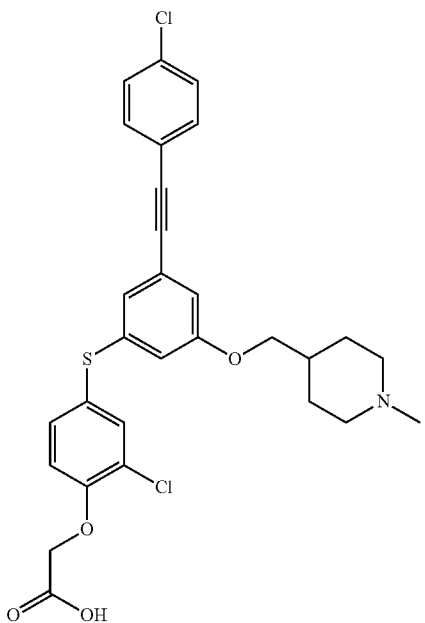 [SMILES: CN1CCC(COc2cc(C#Cc3ccc(Cl)cc3)cc(Sc3ccc(OCC(=O)O)c(Cl)c3)c2)CC1]

Step A: {2-Chloro-4-[3-(4-chloro-phenylethynyl)-5-(1-methyl-piperidin-4-ylmethoxy)-phenylsulfanyl]-phenoxy}-acetic acid ethyl ester {2-Chloro-4-[3-(4-chloro-phenylethynyl)-5-hydroxyl-phenylsulfanyl]-phenoxy}-acetic acid ethyl ester (274 mg; 0.58 mmol) was dissolved in THF (15 mL) in a dried reaction flask under an atmosphere of nitrogen. 1-(Methyl-piperidin-4-yl)-methanol (100 mg; 0.48 mmol) and tributylphosphine (0.21 mL; 0.87 mmol) were added followed by 1,1'-(Azodicarbonyl)dipiperidine (0.22 g; 0.87 mmol) dissolved in THF (10 mL). The reaction mixture was stirred at room temperature for 5 h, filtered, and evaporated in vacuo. The crude product was purified by prep. HPLC (method B). Yield: 250 mg. HPLC-MS: m/z: 663.0 (M+H); Rt: 2.47 min.

Step B: {2-Chloro-4-[3-(4-chloro-phenylethynyl)-5-(1-methyl-piperidin-4-ylmethoxy)phenylsulfanyl]-phenoxy}-acetic acid {2-Chloro-4-[3-(4-chloro-phenylethynyl)-5-(1-methyl-piperidin-4-ylmethoxy)phenylsulfanyl]-phenoxy}-acetic acid ethyl ester (60 mg; 0.10 mmol) was dissolved in ethanol (7 mL), and aqueous 1N sodium hydroxide (3 mL) was added. The reaction mixture was stirred for 16 h, acidified with 1N aqueous hydrochloric acid, and extracted with ethyl acetate. The organic phase was dried, evaporated to dryness and purified by prep. HPLC (method B). Yield: 20 mg. HPLC-MS: m/z: 556.5 (M+); Rt: 2.10 min.

Example 6

{2-Methyl-4-[3-(3-morpholin-4-yl-propoxy)-5-(3-phenyl-prop-1-ynyl)-phenylsulfanyl]-phenoxy}-acetic acid

Step A: {2-Methyl-4-[3-(3-morpholin-4-yl-propoxy)-5-(3-phenyl-prop-1-ynyl)-phenylsulfanyl]-phenoxy}-acetic acid ethyl ester {4-[3-Hydroxy-5-(3-phenyl-prop-1-ynyl)-phenylsulfanyl]-2-methyl-phenoxy}-acetic acid ethyl ester (200 mg; 0.46 mmol), 3-morpholin-4-yl-propan-1-ol (101 mg; 0.69 mmol), tributylphosphine (0.28 mL; 1.39 mmol) and 1,1'-(azodicarbonyl)dipiperidine (0.35 g; 1.39 mmol) were dissolved in THF (15 mL) in a dried reaction flask under an atmosphere of nitrogen. After stirring for 1 h the reaction mixture was purified by prep. HPLC (method A). Yield: 200 mg. HPLC-MS: m/z: 560.5 (M+H); Rt: 2.07 min.

Step B: {2-Methyl-4-[3-(3-morpholin-4-yl-propoxy)-5-(3-phenyl-prop-1-ynyl)-phenylsulfanyl]-phenoxy}-acetic acid {2-Methyl-4-[3-(3-morpholin-4-yl-propoxy)-5-(3-phenyl-prop-1-ynyl)-phenylsulfanyl]-phenoxy}-acetic acid ethyl ester (200 mg; 0.36 mmol) was dissolved in ethanol (20 mL), and aqueous 1 N sodium hydroxide (3 mL) was added. The reaction mixture was stirred for 1 h, acidified with 1 N aqueous hydrochloric acid, and extracted with ethyl acetate.

The organic phase was dried and evaporated to dryness. Yield: 150 mg. HPLC-MS: m/z: 532.1 (M+); Rt: 1.87 min.

Example 7

{4-[3-(4-Fluoro-benzyloxy)-5-(3-morpholin-4-yl-prop-1-ynyl)-phenylsulfanyl]-2-methyl-phenoxy}-acetic acid

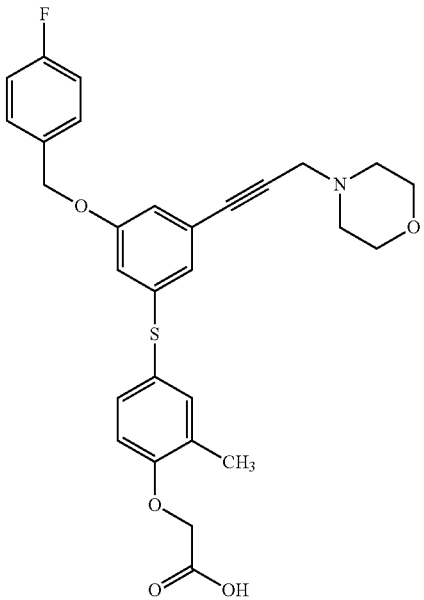 [SMILES: Cc1cc(Sc2cc(C#CCN3CCOCC3)cc(OCc3ccc(F)cc3)c2)ccc1OCC(=O)O]

Step A: {4-[3-(4-Fluoro-benzyloxy)-5-(3-morpholin-4-yl-prop-1-ynyl)-phenylsulfanyl]-2-methyl-phenoxy}-acetic acid ethyl ester {4-[3-Hydroxy-5-(3-morpholin-4-yl-prop-1-ynyl)-phenylsulfanyl]-2-methyl-phenoxy}-acetic acid ethyl ester (200 mg; 0.45 mmol), 4-fluorobenzylalcohol (85.7 mg; 0.68 mmol), tributylphosphine (0.27 mL; 1.36 mmol) and 1,1'-(azodicarbonyl)dipiperidine (0.34 g; 1.36 mmol) were dissolved in THF (15 mL) in a dried reaction flask under an atmosphere of nitrogen. After stirring for 1 h the reaction mixture was purified by prep. HPLC (method A). Yield: 200 mg. HPLC-MS: m/z: 550.3 (M+H); Rt: 2.00 min.

Step B: {4-[3-(4-Fluoro-benzyloxy)-5-(3-morpholin-4-yl-prop-1-ynyl)-phenylsulfanyl]-2-methyl-phenoxy}-acetic acid {4-[3-(4-Fluoro-benzyloxy)-5-(3-morpholin-4-yl-prop-1-ynyl)-phenylsulfanyl]-2-methyl-phenoxy}-acetic acid ethyl ester (200 mg; 0.36 mmol) was dissolved in ethanol (20 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 170 mg. HPLC-MS: m/z: 522.1 (M+); Rt: 1.77 min.

Example 8

{4-[3-Cyclohexylmethoxy-5-(3-morpholin-4-yl-prop-1-ynyl)-phenylsulfanyl]-2-methyl-phenoxy}-acetic acid

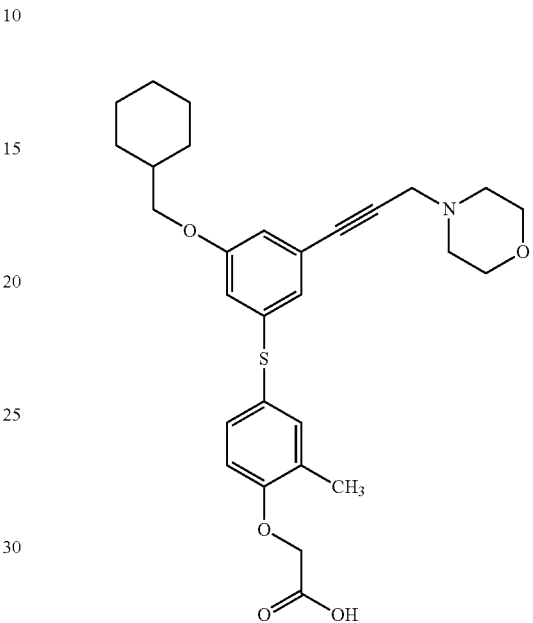

Step A: {4-[3-Cyclohexylmethoxy-5-(3-morpholin-4-yl-prop-1-ynyl)-phenylsulfanyl]-2-methyl-phenoxy}-acetic acid ethyl ester {4-[3-Hydroxy-5-(3-morpholin-4-yl-prop-1-ynyl)-phenylsulfanyl]-2-methyl-phenoxy}-acetic acid ethyl ester (200 mg; 0.45 mmol), cyclohexylmethanol (77.6 mg; 0.68 mmol), tributylphosphine (0.27 mL; 1.36 mmol) and 1,1'-(azodicarbonyl)dipiperidine (0.34 g; 1.36 mmol) were dissolved in THF (15 mL) in a dried reaction flask under an atmosphere of nitrogen. After stirring for 1 h the reaction mixture was purified by prep. HPLC (method A). Yield: 200 mg. HPLC-MS: m/z: 538.1 (M+H); Rt: 2.24 min.

Step B: {4-[3-Cyclohexylmethoxy-5-(3-morpholin-4-yl-prop-1-ynyl)-phenylsulfanyl]-2-methyl-phenoxy}-acetic acid {4-[3-Cyclohexylmethoxy-5-(3-morpholin-4-yl-prop-1-ynyl)-phenylsulfanyl]-2-methyl-phenoxy}-acetic acid ethyl ester (200 mg; 0.37 mmol) was dissolved in ethanol (20 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 180 mg. HPLC-MS: m/z: 510.1 (M+); Rt: 1.98 min.

Example 9

{4-[3-Isobutoxy-5-(3-morpholin-4-yl-prop-1-ynyl)-phenylsulfanyl]-2-methyl-phenoxy}-acetic acid

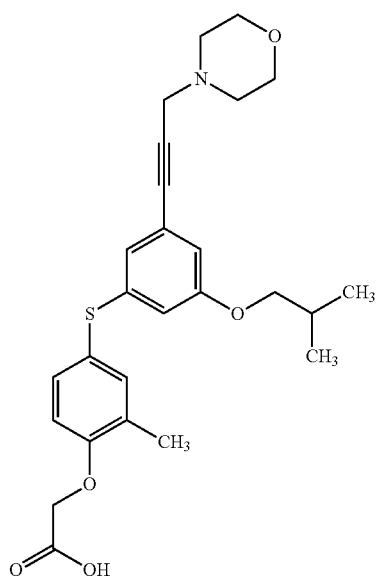 [SMILES: Cc1cc(Sc2cc(C#CCN3CCOCC3)cc(OCC(C)C)c2)ccc1OCC(=O)O]

Step A: {4-[3-Isobutoxy-5-(3-morpholin-4-yl-prop-1-ynyl)-phenylsulfanyl]-2-methyl-phenoxy}-acetic acid ethyl ester {4-[3-Hydroxy-5-(3-morpholin-4-yl-prop-1-ynyl)-phenylsulfanyl]-2-methyl-phenoxy}-acetic acid ethyl ester (250 mg; 0.57 mmol), 2-methyl-propan-1-ol (0.078 mL; 0.85 mmol) and tributylphosphine (0.31 mL; 1.25 mmol) were dissolved in THF (15 mL) in a dried reaction flask under an atmosphere of nitrogen. 1,1'-(Azodicarbonyl)dipiperidine (0.31 g; 1.25 mmol) was dissolved in THF (10 mL) and added to the reaction mixture. After stirring for 16 h the reaction mixture was evaporated to dryness and purified by prep. HPLC (method B). Yield: 200 mg. HPLC-MS: m/z: 498.1 (M+); Rt: 2.03 min

Step B: {4-[3-Isobutoxy-5-(3-morpholin-4-yl-prop-1-ynyl)-phenylsulfanyl]-2-methyl-phenoxy}-acetic acid {4-[3-Isobutoxy-5-(3-morpholin-4-yl-prop-1-ynyl)-phenylsulfanyl]-2-methyl-phenoxy}-acetic acid ethyl ester (140 mg; 0.28 mmol) was dissolved in ethanol (15 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 130 mg. HPLC-MS: m/z: 470.0 (M+); Rt: 1.76 min. $\delta_H$ (400 MHz; CDCl$_3$) 1.00 (d, 6H), 1.98-2.09 (m, 1H), 2.27 (s, 3H), 3.13-3.29 (m, 2H), 3.43-3.57 (m, 2H), 3.66 (d, 2H), 3.92-4.09 (m, 4H), 4.12 (s, 2H), 4.71 (s, 2H), 6.55 (m, 1H), 6.71-6.75 (m, 2H), 6.79 (m, 1H), 7.25-7.29 (m, 1H), 7.30 (m, 1H).

Example 10

{4-[3-(4-Chloro-benzyloxy)-5-(3-morpholin-4-yl-prop-1-ynyl)-phenylsulfanyl]-2-methyl-phenoxy}-acetic acid

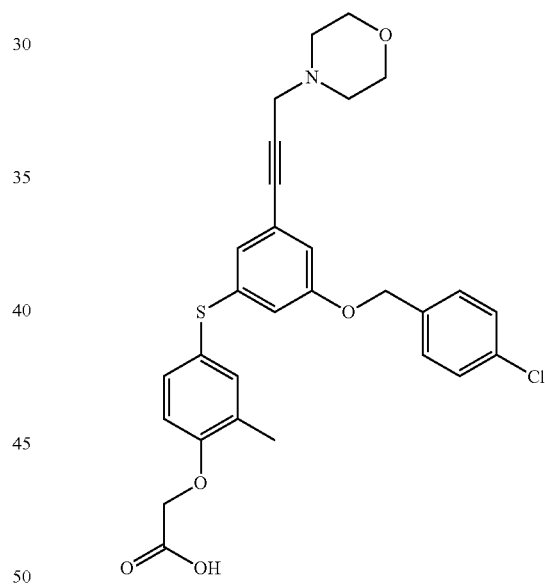

Step A: {4-[3-(4-Chloro-benzyloxy)-5-(3-morpholin-4-yl-prop-1-ynyl)-phenylsulfanyl]-2-methyl-phenoxy}-acetic acid ethyl ester 4-[3-Hydroxy-5-(3-morpholin-4-yl-prop-1-ynyl)-phenylsulfanyl]-2-methyl-phenoxy}-acetic acid ethyl ester (250 mg; 0.57 mmol), 4-(chloro-phenyl)-methanol (0.12 mg; 0.85 mmol) and tributylphosphine (0.31 mL; 1.25 mmol) were dissolved in THF (15 mL) in a dried reaction flask under an atmosphere of nitrogen. 1,1'-(Azodicarbonyl)dipiperidine (0.31 g; 1.25 mmol) was dissolved in THF (10 mL) and added to the reaction mixture. After stirring for 16 h the reaction mixture was evaporated to dryness and purified by prep. HPLC (method B). Yield: 200 mg. HPLC-MS: m/z: 566.1 (M+); Rt: 2.13 min.

Step B: {4-[3-(4-Chloro-benzyloxy)-5-(3-morpholin-4-yl-prop-1-ynyl)-phenylsulfanyl]-2-methyl-phenoxy}-acetic acid {4-[3-(4-Chloro-benzyloxy)-5-(3-morpholin-4-yl-prop-1-ynyl)-phenylsulfanyl]-2-methyl-phenoxy}-acetic acid ethyl ester (140 mg; 0.28 mmol) was dissolved in ethanol (15 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 180 mg. HPLC-MS: m/z: 538.0 (M+); Rt: 1.84 min. $\delta_H$ (400 MHz; CDCl$_3$) 2.27 (s, 3H), 3.15-3.30 (m, 2H), 3.45 (d, 2H), 3.99-4.06 (m, 2H), 4.13-4.22 (m, 4H), 4.73 (s, 2H), 4.96 (s, 2H), 6.57-6.60 (m, 1H), 6.74 (d, 1H), 6.76-6.81 (m, 2H), 7.25-7.31 (m, 4H), 7.32-7.36 (m, 2H).

Example 11

{2-Chloro-4-[3-(4-chloro-phenylethynyl)-5-hydroxy-phenylsulfanyl]-phenoxy}-acetic acid

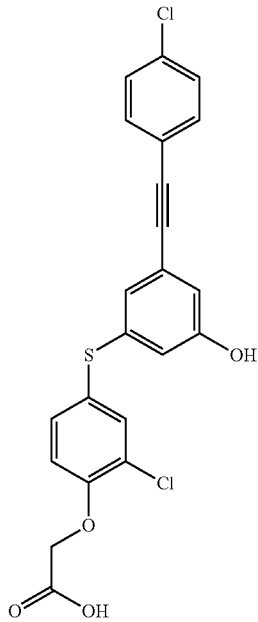 [SMILES: O=C(O)COc1ccc(Sc2cc(O)cc(C#Cc3ccc(Cl)cc3)c2)cc1Cl]

{2-Chloro-4-[3-(4-chloro-phenylethynyl)-5-hydroxy-phenylsulfanyl]-phenoxy}-acetic acid ethyl ester (50 mg; 0.11 mmol) was dissolved in ethanol (6 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness and purified by prep. HPLC (method B). Yield: 36 mg. HPLC-MS: m/z: 445.1 (M+); Rt: 2.44 min.

Example 12

{4-[3-But-2-ynyloxy-5-(3-morpholin-4-yl-prop-1-ynyl)-phenylsulfanyl]-2-methyl-phenoxy}-acetic acid

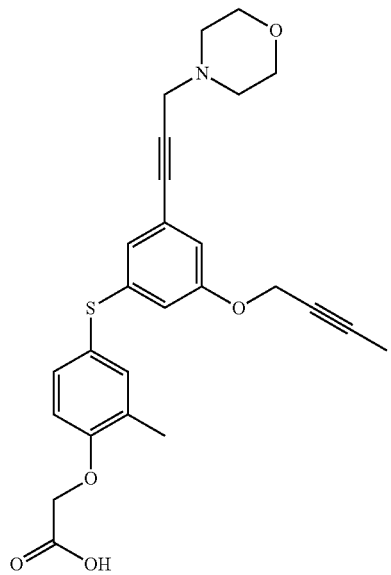 [SMILES: CC#CCOc1cc(C#CCN2CCOCC2)cc(Sc2ccc(OCC(=O)O)c(C)c2)c1]

Step A: {4-[3-But-2-ynyloxy-5-(3-morpholin-4-yl-prop-1-ynyl)-phenylsulfanyl]-2-methyl-phenoxy}-acetic acid ethyl ester 4-[3-Hydroxy-5-(3-morpholin-4-yl-prop-1-ynyl)-phenylsulfanyl]-2-methyl-phenoxy}-acetic acid ethyl ester (250 mg; 0.57 mmol), 2-butyn-1-ol (0.064 mL; 0.85 mmol) and tributyl-phosphine (0.31 mL; 1.25 mmol) were dissolved in THF (15 mL) in a dried reaction flask under an atmosphere of nitrogen. 1,1'-(Azodicarbonyl)dipiperidine (0.31 g; 1.25 mmol) was dissolved in THF (10 mL) and added to the reaction mixture. After stirring for 16 h the reaction mixture was evaporated to dryness and purified by prep. HPLC (method B). Yield: 150 mg. HPLC-MS: m/z: 494.0 (M+); Rt: 1.87 min.

Step B: {4-[3-But-2-ynyloxy-5-(3-morpholin-4-yl-prop-1-ynyl)-phenylsulfanyl]-2-methyl-phenoxy}-acetic acid {4-[3-But-2-ynyloxy-5-(3-morpholin-4-yl-prop-1-ynyl)-phenylsulfanyl]-2-methyl-phenoxy}-acetic acid ethyl ester (150 mg; 0.30 mmol) was dissolved in ethanol (15 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 140 mg. HPLC-MS: m/z: 466.0 (M+); Rt: 1.60 min.

Example 13

{2-Methyl-4-[3-(2-morpholin-4-yl-ethoxy)-5-phenylethynyl-phenylsulfanyl]-phenoxy}-acetic acid

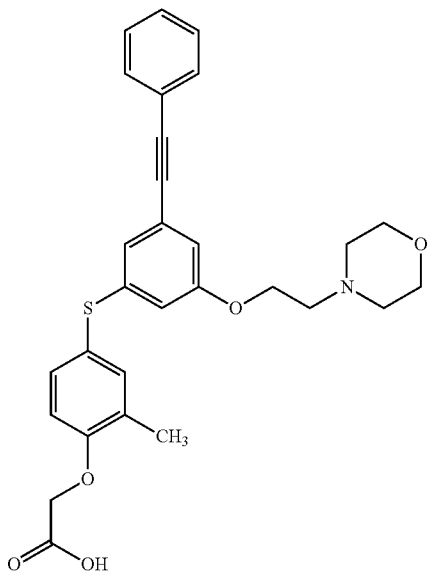 [SMILES: Cc1cc(Sc2cc(C#Cc3ccccc3)cc(OCCN3CCOCC3)c2)ccc1OCC(=O)O]

Step A: {2-Methyl-4-[3-(2-morpholin-4-yl-ethoxy)-5-phenylethynyl-phenylsulfanyl]-phenoxy}-acetic acid ethyl ester

[4-(3-Hydroxy-5-phenylethynyl-phenylsulfanyl)-2-methyl-phenoxy]-acetic acid ethyl ester (200 mg; 0.48 mmol), 2-morpholin-4-yl-ethanol (0.22 g; 0.67 mmol) and tributylphosphine (0.24 mL; 0.96 mmol) were dissolved in THF (15 mL) in a dried reaction flask under an atmosphere of nitrogen. 1,1'-(Azodicarbonyl)dipiperidine (0.24 g; 0.96 mmol) was dissolved in THF (10 mL) and added to the reaction mixture. After stirring for 16 h the reaction mixture was evaporated to dryness and purified by flash chromatography (ethyl acetate:heptane (1:3→1:9). Yield: 150 mg. HPLC-MS: m/z: 532.6 (M+H); Rt: 2.07 min.

Step B: {2-Methyl-4-[3-(2-morpholin-4-yl-ethoxy)-5-phenylethynyl-phenylsulfanyl]-phenoxy}-acetic acid {2-Methyl-4-[3-(2-morpholin-4-yl-ethoxy)-5-phenylethynyl-phenylsulfanyl]-phenoxy}-acetic acid ethyl ester (150 mg; 0.30 mmol) was dissolved in ethanol (15 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 140 mg. HPLC-MS: m/z: 504.1 (M+); Rt: 1.80 min.

Example 14

{2-Chloro-4-[3-(3-methoxy-prop-1-ynyl)-5-(3-morpholin-4-yl-propoxy)-phenyl-sulfanyl]-phenoxy}-acetic acid

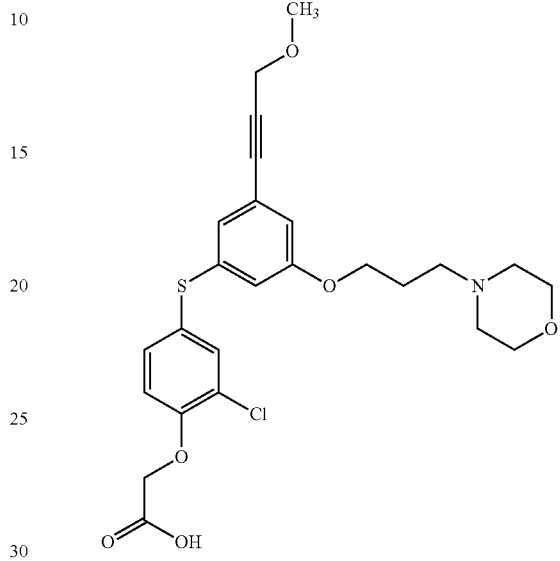

Step A: {2-Chloro-4-[3-(3-methoxy-prop-1-ynyl)-5-(3-morpholin-4-yl-propoxy)-phenylsulfanyl]-phenoxy}-acetic acid ethyl ester {4-[3-Bromo-5-(3-morpholin-4-yl-propoxy)-phenylsulfanyl]-2-chloro-phenoxy}-acetic acid ethyl ester (0.2 g; 0.37 mmol), 3-methoxy-propyne (0.10 g; 1.47 mmol), bis(triphenylphosphine) palladium (II) chloride (21 mg; 0.029 mmol) and copper iodide (4.2 mg; 0.022 mmol) were dissolved in a mixture of triethylamine (2 mL) and DMF (2 mL) under an atmosphere of nitrogen. The reaction mixture was reacted in a microwave oven at 150° C. for 1 h. The reaction mixture was evaporated to dryness and extracted with ethyl acetate from a aqueous 5% citric acid solution. The crude product was dried, evaporated to dryness and purified by preparative HPLC (method B). Yield: 160 mg. HPLC-MS: m/z: 534.1 (M+); Rt: 1.79 min.

Step B: {2-Chloro-4-[3-(3-methoxy-prop-1-ynyl)-5-(3-morpholin-4-yl-propoxy)-phenylsulfanyl]-phenoxy}-acetic acid {2-Chloro-4-[3-(3-methoxy-prop-1-ynyl)-5-(3-morpholin-4-yl-propoxy)-phenyl-sulfanyl]-phenoxy}-acetic acid ethyl ester (150 mg; 0.30 mmol) was dissolved in ethanol (10 mL), and aqueous 1 N sodium hydroxide (3 mL) was added. The reaction mixture was stirred for 1 h, acidified with 1 N aqueous hydrochloric acid, and extracted with ethyl acetate. The organic phase was dried, and evaporated to dryness and purified by preparative HPLC (method B). Yield: 50 mg. HPLC-MS: m/z: 506.0 (M+); Rt: 1.56 min. $\delta_H$ (400 MHz;

CDCl$_3$) 2.06-2.15 (m, 2H), 2.82-2.92 (m, 2H), 3.15-3.23 (m, 2H), 3.45 (s, 3H), 3.56 (d, 2H), 3.78 (t, 2H), 3.95-4.03 (m, 4H), 4.30 (s, 2H), 4.89 (s, 2H), 5.91-5.94 (m, 1H), 6.63-6.66 (m, 1H), 6.93 (d, 1H), 7.01-7.03 (m, 1H), 7.40 (dd, 1H), 7.58 (d, 1H).

Example 15

{2-Chloro-4-[3-(3-morpholin-4-yl-propoxy)-5-pent-1-ynyl-phenylsulfanyl]-phenoxy}-acetic acid

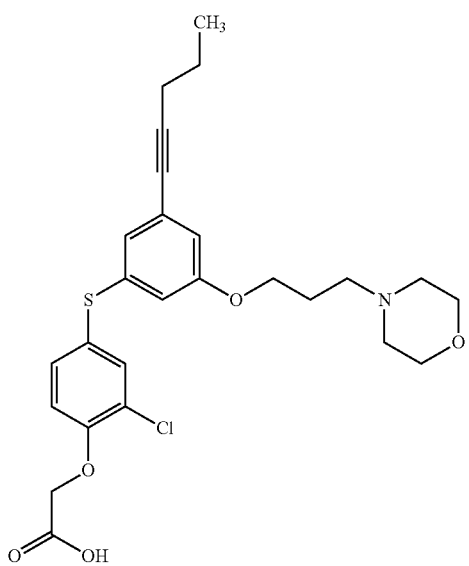 [SMILES: CCCC#Cc1cc(OCCCN2CCOCC2)cc(Sc2ccc(OCC(=O)O)c(Cl)c2)c1]

Step A: {2-Chloro-4-[3-(3-morpholin-4-yl-propoxy)-5-pent-1-ynyl-phenylsulfanyl]-phenoxy}-acetic acid ethyl ester {4-[3-Bromo-5-(3-morpholin-4-yl-propoxy)-phenylsulfanyl]-2-chloro-phenoxy}-acetic acid ethyl ester (0.2 g; 0.37 mmol), 1-pentyne (0.10 g; 1.47 mmol), bis(triphenyl-phosphine)palladium (II) chloride (21 mg; 0.029 mmol) and copper iodide (4.2 mg; 0.022 mmol) were dissolved in a mixture of triethylamine (2 mL) and DMF (2 mL) under an atmosphere of nitrogen. The reaction mixture was reacted in a microwave oven at 150° C. for 1 h. The reaction mixture was evaporated to dryness and extracted with ethyl acetate from a aqueous 5% citric acid solution. The crude product was dried, evaporated to dryness and purified by preparative HPLC (method B). Yield: 120 mg. HPLC-MS: m/z: 532.0 (M+); Rt: 2.02 min.

Step B: {2-Chloro-4-[3-(3-morpholin-4-yl-propoxy)-5-pent-1-ynyl-phenylsulfanyl]-phenoxy}-acetic acid {2-Chloro-4-[3-(3-morpholin-4-yl-propoxy)-5-pent-1-ynyl-phenylsulfanyl]-phenoxy}-acetic acid ethyl ester (150 mg; 0.30 mmol) was dissolved in ethanol (10 mL), and aqueous 1 N sodium hydroxide (3 mL) was added. The reaction mixture was stirred for 1 h, acidified with 1 N aqueous hydrochloric acid, and extracted with ethyl acetate. The organic phase was dried, and evaporated to dryness and purified by preparative HPLC (method B). Yield: 70 mg. HPLC-MS: m/z: 504.1 (M+); Rt: 1.81 min.

Example 16

{2-Methyl-4-[3-(3-morpholin-4-yl-propoxy)-5-(3-phenyl-prop-1-ynyl)-benzylsulfanyl]-phenoxy}-acetic acid

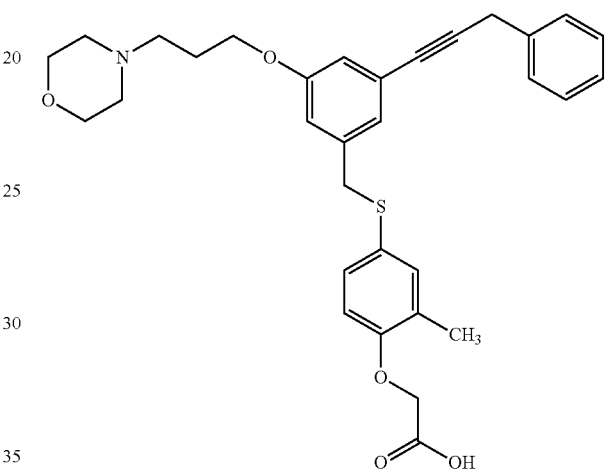

Step A: {2-Methyl-4-[3-(3-morpholin-4-yl-propoxy)-5-(3-phenyl-prop-1-ynyl)-benzylsulfanyl]-phenoxy}-acetic acid ethyl ester {4-[3-Hydroxy-5-(3-phenyl-prop-1-ynyl)-benzylsulfanyl]-2-methyl-phenoxy}-acetic acid ethyl ester (200 mg; 0.45 mmol), 3-morpholin-4-yl-propan-1-ol (97.6 mg; 0.67 mmol), tributylphosphine (0.27 mg; 1.34 mmol) and 1,1'-(Azodicarbonyl)dipiperidine (0.34 g; 1.34 mmol) were dissolved in THF (20 mL) in a dried reaction flask under an atmosphere of nitrogen. The reaction mixture was stirred for 1 h and purified by prep. HPLC (method A). Yield: 200 mg. HPLC-MS: m/z: 574.3 (M+H); Rt: 2.07 min.

Step B: {2-Methyl-4-[3-(3-morpholin-4-yl-propoxy)-5-(3-phenyl-prop-1-ynyl)-benzylsulfanyl]-phenoxy}-acetic acid {2-Methyl-4-[3-(3-morpholin-4-yl-propoxy)-5-(3-phenyl-prop-1-ynyl)-benzylsulfanyl]-phenoxy}-acetic acid ethyl ester (150 mg; 0.30 mmol) was dissolved in ethanol (20 mL), and aqueous 1 N sodium hydroxide (3 mL) was added.

The reaction mixture was stirred for 1 h, acidified with 1 N aqueous hydrochloric acid, and extracted with ethyl acetate. The organic phase was dried and evaporated to dryness. Yield: 190 mg. HPLC-MS: m/z: 546.1 (M+); Rt: 1.85 min.

Example 17

{4-[3-(4-Fluoro-benzyloxy)-5-(3-morpholin-4-yl-prop-1 ynyl)-benzylsulfanyl]-2-methyl-phenoxy}-acetic acid

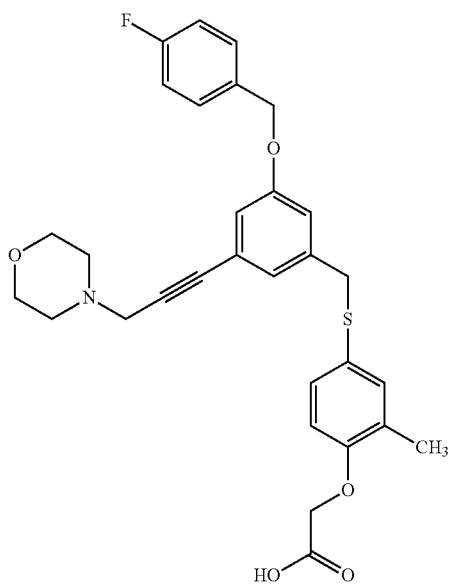 [SMILES: Cc1cc(SCc2cc(C#CCN3CCOCC3)cc(OCc3ccc(F)cc3)c2)ccc1OCC(=O)O]

Step A: {4-[3-(4-Fluoro-benzyloxy)-5-(3-morpholin-4-yl-prop-1 ynyl)-benzylsulfanyl]-2-methyl-phenoxy}-acetic acid ethyl ester {4-[3-Hydroxy-5-(3-morpholin-4-yl-prop-1-ynyl)-benzylsulfanyl]-2-methyl-phenoxy}-acetic acid ethyl ester (250 mg; 0.55 mmol), 1-fluoro-4-methoxymethyl-benzene (103.8 mg; 0.82 mmol), tributylphosphine (0.33 mg; 1.65 mmol) and 1,1'-(azodicarbonyl)dipiperidine (0.414 g; 1.65 mmol) were dissolved in THF (15 mL) in a dried reaction flask under an atmosphere of nitrogen. The reaction mixture was stirred for 16 h and purified by prep. HPLC (method A). Yield: 160 mg. HPLC-MS: m/z: 564.1 (M+H); Rt: 1.99 min.

Step B: {4-[3-(4-Fluoro-benzyloxy)-5-(3-morpholin-4-yl-prop-1 ynyl)-benzylsulfanyl]-2-methyl-phenoxy}-acetic acid {4-[3-(4-Fluoro-benzyloxy)-5-(3-morpholin-4-yl-prop-1 ynyl)-benzylsulfanyl]-2-methyl-phenoxy}-acetic acid ethyl ester (150 mg; 0.30 mmol) was dissolved in ethanol (20 mL), and aqueous 1 N sodium hydroxide (3 mL) was added. The reaction mixture was stirred for 1 h, acidified with 1 N aqueous hydrochloric acid, and extracted with ethyl acetate. The organic phase was dried and evaporated to dryness. Yield: 190 mg. HPLC-MS: m/z: 536.1 (M+); Rt: 1.76 min.

Example 18

{2-Methyl-4-[3-(3-morpholin-4-yl-ethoxy)-5-(3-phenyl-prop-1-ynyl)-benzylsulfanyl]-phenoxy}-acetic acid

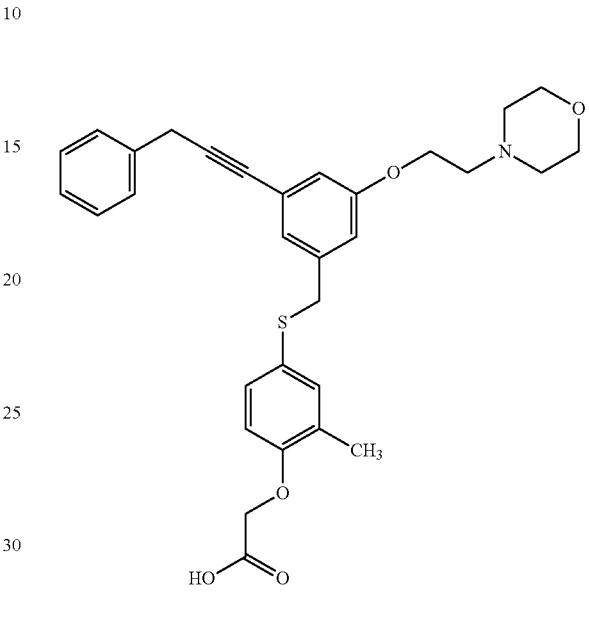

Step A: {2-Methyl-4-[3-(3-morpholin-4-yl-ethoxy)-5-(3-phenyl-prop-1-ynyl)-benzyl-sulfanyl]-phenoxy}-acetic acid ethyl ester {4-[3-Hydroxy-5-(3-phenyl-prop-1-ynyl)-benzylsulfanyl]-2-methyl-phenoxy}-acetic acid ethyl ester (250 mg; 0.56 mmol), 3-morpholin-4-yl-propan-1-ol (110.1 mg; 0.84 mmol), tributylphosphine (0.34 mL; 1.68 mmol) and 1,1'-(azodicarbonyl)dipiperidine (0.42 g; 1.68 mmol) were dissolved in THF (15 mL) in a dried reaction flask under an atmosphere of nitrogen. After stirring for 2 h the reaction mixture was purified by prep. HPLC (method A). Yield: 50 mg. HPLC-MS: m/z: 560.2 (M+H); Rt: 2.03 min.

Step B: {2-Methyl-4-[3-(3-morpholin-4-yl-ethoxy)-5-(3-phenyl-prop-1-ynyl)-benzyl-sulfanyl]-phenoxy}-acetic acid {2-Methyl-4-[3-(3-morpholin-4-yl-ethoxy)-5-(3-phenyl-prop-1-ynyl)-benzylsulfanyl]-phenoxy}-acetic acid ethyl ester (50 mg; 0.09 mmol) was dissolved in ethanol (10 mL), and aqueous 1 N sodium hydroxide (2 mL) was added. The reaction mixture was stirred for 16 h, acidified with 1 N aqueous hydrochloric acid and extracted with dichloromethane. The organic phase was dried and evaporated to dryness. Yield: 45 mg. HPLC-MS: m/z: 532.1 (M+); Rt: 1.79 min.

Example 19

{4-[3-Cyclohexylmethoxy-5-(4-methanesulfonyl-phenylethynyl)-phenylsulfanyl]-2-methyl-phenoxy}-acetic acid

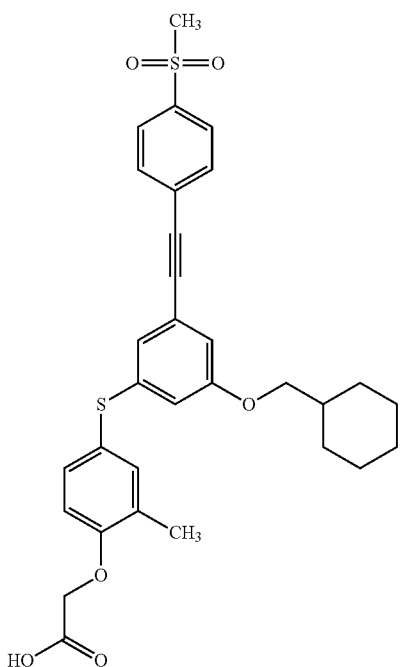 [SMILES: Cc1cc(Sc2cc(C#Cc3ccc(S(C)(=O)=O)cc3)cc(OCC3CCCCC3)c2)ccc1OCC(=O)O]

Step A: {4-[3-Cyclohexylmethoxy-5-(4-methane-sulfonyl-phenylethynyl)-phenyl-sulfanyl]-2-methyl-phenoxy}-acetic acid ethyl ester

[4-(3-Bromo-5-cyclohexylmethoxy-phenylsulfanyl)-2-methyl-phenoxy]-acetic acid ethyl acetate (0.1 g; 0.203 mmol), 1-Ethynyl-4-methanesulfonyl-benzene (0.109 g; 0.61 mmol), bis(triphenylphosphine)palladium (II) chloride (11.4 mg; 0.016 mmol) and copper iodide (2.3 mg; 0.06 mmol) were dissolved in a mixture of triethylamine (2 mL) and DMF (2 mL) under an atmosphere of nitrogen. The reaction mixture was reacted in a microwave oven at 120° C. for 1 h. Water and dichloromethane was added to the reaction mixture and the phases were separated and washed with water. The organic phase was dried and evaporated to dryness. The crude product was purified by prep. HPLC (Metode A). Yield: 90 mg. HPLC-MS: m/z: 593.5 (M+H)+; Rt: 3.04 min.

Step B: {4-[3-Cyclohexylmethoxy-5-(4-methane-sulfonyl-phenylethynyl)-phenyl-sulfanyl]-2-methyl-phenoxy}-acetic acid {4-[3-Cyclohexylmethoxy-5-(4-methanesulfonyl-phenylethynyl)-phenylsulfanyl]-2-methyl-phenoxy}-acetic acid ethyl ester (120 mg; 0.202 mmol) was dissolved in ethanol (50 mL), and aqueous 1 N sodium hydroxide (2 mL) was added. The reaction mixture was stirred for 30 min, acidified with 1 N aqueous hydrochloric acid and extracted with dichloromethane. The organic phase was dried and evaporated to dryness. Yield: 90 mg. HPLC-MS: m/z: 565.3 (M+H)+; Rt: 2.81 min.

Example 20

{4-[3-Cyclopentylmethoxy-5-(4-methanesulfonyl-phenylethynyl)-phenylsulfanyl]-2-methyl-phenoxy}-acetic acid

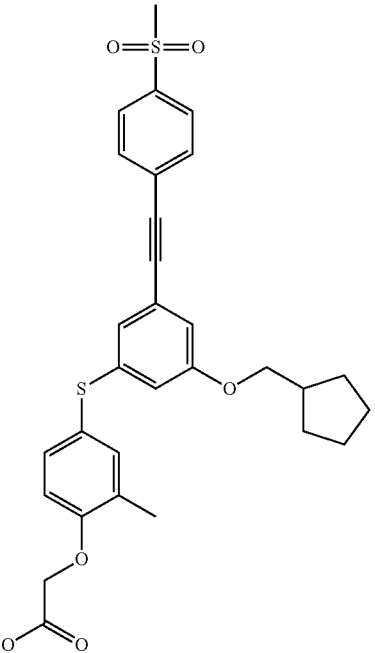 [SMILES: Cc1cc(Sc2cc(C#Cc3ccc(S(C)(=O)=O)cc3)cc(OCC3CCCC3)c2)ccc1OCC(=O)O]

Step A: {4-[3-Cyclopentylmethoxy-5-(4-methane-sulfonyl-phenylethynyl)-phenyl-sulfanyl]-2-methyl-phenoxy}-acetic acid ethyl ester

[4-(3-Bromo-5-cyclopentylmethoxy-phenylsulfanyl)-2-methyl-phenoxy]-acetic acid ethyl acetate (0.24 g; 0.50 mmol), 1-Ethynyl-4-methanesulfonyl-benzene (0.271 g; 1.5 mmol), bis(triphenylphosphine)palladium (II) chloride (28.11 mg; 0.04 mmol) and copper iodide (5.7 mg; 0.03 mmol) were dissolved in a mixture of triethylamine (5 mL) and DMF (5 mL) under an atmosphere of nitrogen. The reaction mixture was reacted in a microwave oven at 120° C. for 1 h. Water and dichloromethane was added to the reaction mixture and the phases were separated and washed with water. The organic phase was dried and evaporated to dryness. The crude product was purified by prep. HPLC (Metode A). Yield: 180 mg. HPLC-MS: m/z: 579.4 (M+H)+; Rt: 3.00 min.

Step B: {4-[3-Cyclopentylmethoxy-5-(4-methane-sulfonyl-phenylethynyl)-phenyl-sulfanyl]-2-methyl-phenoxy}-acetic acid {4-[3-Cyclopentylmethoxy-5-(4-methanesulfonyl-phenylethynyl)-phenylsulfanyl]-2-methyl-phenoxy}-acetic acid ethyl ester (120 mg; 0.202 mmol) was dissolved in ethanol (50 mL), and aqueous 1 N sodium hydroxide (2 mL) was added. The reaction mixture was stirred for 30 min, acidified with 1 N aqueous hydrochloric acid and extracted with dichloromethane. The organic phase was dried and evaporated to dryness. Yield: 100 mg. HPLC-MS: m/z: 551.5 (M+H)+; Rt: 2.69 min.

Example 21

{4-[3-Isobutoxy-5-(4-methanesulfonyl-phenylethynyl)-phenylsulfanyl]-2-methyl-phenoxy}-acetic acid

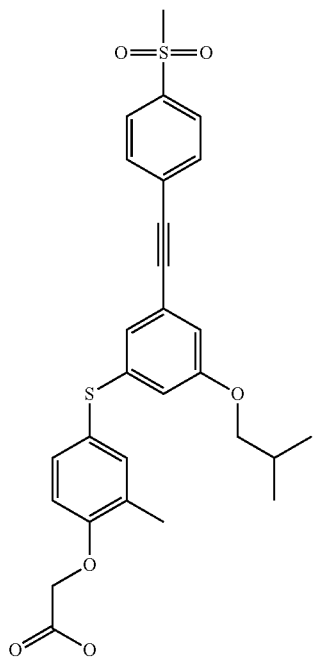 [SMILES: Cc1cc(Sc2cc(C#Cc3ccc(S(C)(=O)=O)cc3)cc(OCC(C)C)c2)ccc1OCC(=O)O]

Step A: {4-[3-Isobutoxy-5-(4-methanesulfonyl-phenylethynyl)-phenylsulfanyl]-2-methyl-phenoxy}-acetic acid ethyl ester The title product was prepared as described for {4-[3-Cyclopentylmethoxy-5-(4-methanesulfonyl-phenylethynyl)-phenylsulfanyl]-2-methyl-phenoxy}-acetic acid ethyl ester. The crude product was purified by prep. HPLC (method B). Yield: 52%. HPLC-MS: m/z: 552.7 (M)+; Rt: 2.88 min.

Step B: {4-[3-Isobutoxy-5-(4-methanesulfonyl-phenylethynyl)-phenylsulfanyl]-2-methyl-phenoxy}-acetic acid {4-[3-Isobutoxy-5-(4-methanesulfonyl-phenylethynyl)-phenylsulfanyl]-2-methyl-phenoxy}-acetic acid ethyl ester (190 mg; 0.34 mmol) was dissolved in ethanol (10 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 110 mg (61%). HPLC-MS: m/z: 525.1 (M+H)+; Rt: 2.55 min.

Example 22

{4-[3-[2-(4-Chloro-phenyl)-ethoxy]-5-(4-methanesulfonyl-phenylethynyl)-phenylsulfanyl]-2-methyl-phenoxy}-acetic acid

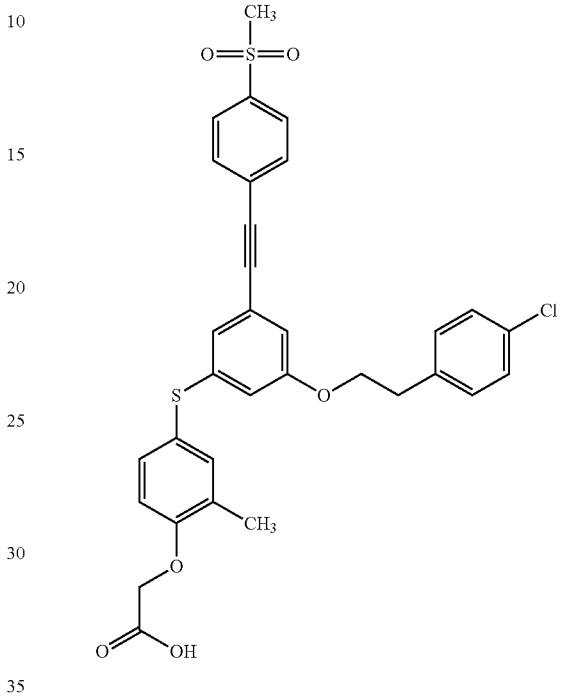

Step A: {4-[3-[2-(4-Chloro-phenyl)-ethoxy]-5-(4-methanesulfonyl-phenylethynyl)-phenylsulfanyl]-2-methyl-phenoxy}-acetic acid ethyl ester The title product was prepared as described for {4-[3-Cyclopentylmethoxy-5-(4-methanesulfonyl-phenylethynyl)-phenylsulfanyl]-2-methyl-phenoxy}-acetic acid ethyl ester. The crude product was purified by prep. HPLC (method B). Yield: 64%. HPLC-MS: m/z: 635.4 (M+H)+; Rt: 2.92 min.

Step B: {4-[3-[2-(4-Chloro-phenyl)-ethoxy]-5-(4-methanesulfonyl-phenylethynyl)-phenylsulfanyl]-2-methyl-phenoxy}-acetic acid {4-[3-[2-(4-Chloro-phenyl)-ethoxy]-5-(4-methanesulfonyl-phenylethynyl)-phenyl-sulfanyl]-2-methyl-phenoxy}-acetic acid ethyl ester (190 mg; 0.30 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 160 mg (89%). HPLC-MS: m/z: 607.1 (M+H)+; Rt: 2.82 min.

Example 23

{4-[3-[2-(4-Chloro-phenyl)-ethoxy]-5-(3-morpholin-4-yl-prop-1-ynyl)-phenylsulfanyl]-2-methyl-phenoxy}-acetic acid

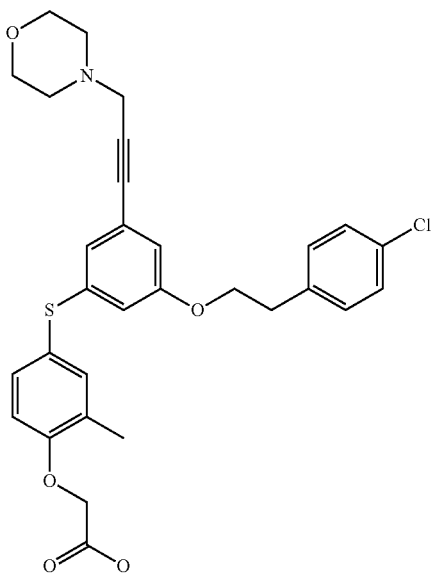 [SMILES: Cc1cc(Sc2cc(C#CCN3CCOCC3)cc(OCCc3ccc(Cl)cc3)c2)ccc1OCC(=O)O]

Step A: {4-[3-[2-(4-Chloro-phenyl)-ethoxy]-5-(3-morpholin-4-yl-prop-1-ynyl)-phenylsulfanyl]-2-methyl-phenoxy}-acetic acid ethyl ester (4-{3-Bromo-5-[2-(4-chloro-phenyl)-ethoxy]-phenylsulfanyl}-2-methyl-phenoxy)-acetic acid ethyl ester (300 mg; 0.56 mmol), 4-prop-2-ynyl-morpholine (280.4 mg; 2.2 mmol), bis(triphenylphosphine) palladium (II) chloride (31.4 mg; 0.045 mmol) and copper iodide (6.4 mg; 0.034 mmol) were dissolved in a mixture of triethylamine (2 mL) and DMF (2 mL) under an atmosphere of nitrogen. The reaction mixture was reacted in a microwave oven at 110° C. for 1.5 h. The reaction mixture was evaporated to dryness, and 5% aqueous citric acid (30 mL) and ethyl acetate (30 mL) was added. The two phases were separated and the aqueous phase was extracted with ethyl acetate (30 mL). The combined organic phases were dried and evaporated to dryness and purified by preparative HPLC (method B). Yield: 300 mg; 92%. HPLC-MS: m/z: 580.7 (M+H)+; Rt: 2.16 min.

Step B: {4-[3-[2-(4-Chloro-phenyl)-ethoxy]-5-(3-morpholin-4-yl-prop-1-ynyl)-phenyl-sulfanyl]-2-methyl-phenoxy}-acetic acid {4-[3-[2-(4-Chloro-phenyl)-ethoxy]-5-(3-morpholin-4-yl-prop-1-ynyl)-phenylsulfanyl]-2-methyl-phenoxy}-acetic acid ethyl ester (190 mg; 0.30 mmol) was dissolved in ethanol (25 mL), and aqueous 1 N sodium hydroxide (5 mL) was added. The reaction mixture was stirred for 16 h. acidified with 1 N aqueous hydrochloric acid and extracted with ethyl acetate. The organic phase was dried and evaporated to dryness, redissolved in dichloromethane and evaporated to dryness. Yield: 250 mg (87%). HPLC-MS: m/z: 552.8 (M+H)+; Rt: 1.90 min.

Example 24

{4-[3-[2-(4-Chloro-phenyl)-ethoxy]-5-(4-hydroxymethyl-phenylethynyl)-phenyl-sulfanyl]-2-methyl-phenoxy}-acetic acid

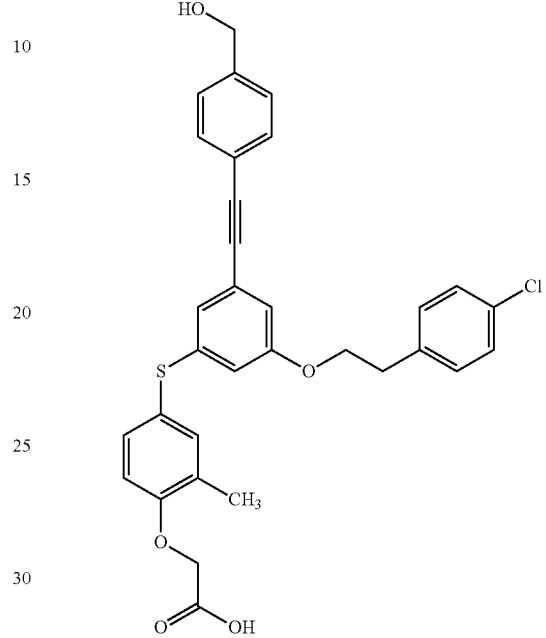

Step A: {4-[3-[2-(4-Chloro-phenyl)-ethoxy]-5-(4-hydroxymethyl-phenylethynyl)-phenylsulfanyl]-2-methyl-phenoxy}-acetic acid ethyl ester (4-{3-Bromo-5-[2-(4-chloro-phenyl)-ethoxy]-phenylsulfanyl}-2-methyl-phenoxy)-acetic acid ethyl ester (270 mg; 0.46 mmol), (4-ethynyl-phenyl)-methanol (296 mg; 2.2 mmol), bis(triphenylphosphine) palladium (II) chloride (31.4 mg; 0.045 mmol) and copper iodide (6.4 mg; 0.034 mmol) were dissolved in a mixture of triethylamine (2 mL) and DMF (2 mL) under an atmosphere of nitrogen. The reaction mixture was reacted in a microwave oven at 110° C. for 1.5 h. The reaction mixture was evaporated to dryness, and 5% aqueous citric acid (30 mL) and ethyl acetate (30 mL) was added. The two phases were separated and the aqueous phase was extracted with ethyl acetate (30 mL). The combined organic phases were dried and evaporated to dryness and purified by preparative HPLC (method B). Yield: 270 mg (83%). HPLC-MS: m/z: 587.1 (M+H)+; Rt: 2.96 min.

Step B: {4-[3-[2-(4-Chloro-phenyl)-ethoxy]-5-(4-hydroxymethyl-phenylethynyl)-phenylsulfanyl]-2-methyl-phenoxy}-acetic acid {4-[3-[2-(4-Chloro-phenyl)-ethoxy]-5-(4-hydroxymethyl-phenylethynyl)-phenyl-sulfanyl]-2-methyl-phenoxy}-acetic acid ethyl ester (270 mg; 0.46 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried, evaporated to dryness and purified by prep HPLC (method B). Yield: 218 mg (85%). HPLC-MS: m/z: 559.1 (M+H)+; Rt: 2.61 min.

Example 25

{4-[3-(2-Ethyl-butoxy)-5-phenylethynyl-phenylsulfanyl]-2-methyl-phenoxy}-acetic acid

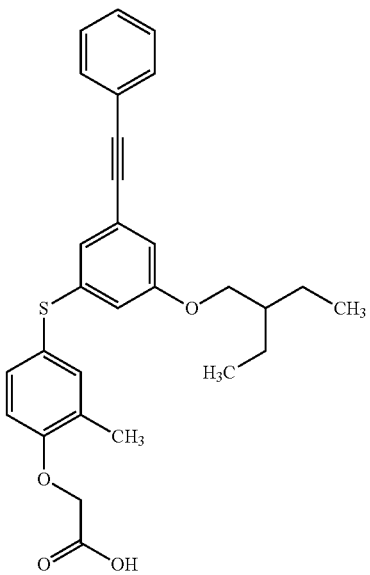 [SMILES: CCC(CC)COc1cc(C#Cc2ccccc2)cc(Sc2ccc(OCC(=O)O)c(C)c2)c1]

Step A: {4-[3-(2-Ethyl-butoxy)-5-phenylethynyl-phenylsulfanyl]-2-methyl-phenoxy}-acetic acid ethyl ester The title product was prepared from {4-[3-Bromo-5-(2-ethyl-butoxy)-phenylsulfanyl]-2-methyl-phenoxy}-acetic acid ethyl ester (200 mg; 0.42 mmol), (phenyl acetylene (170 mg; 1.66 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 170 mg (82%). HPLC-MS: m/z: 502.9 (M)+; Rt: 3.32 min.

Step B: {4-[3-(2-Ethyl-butoxy)-5-phenylethynyl-phenylsulfanyl]-2-methyl-phenoxy}-acetic acid {4-[3-(2-Ethyl-butoxy)-5-phenylethynyl-phenylsulfanyl]-2-methyl-phenoxy}-acetic acid ethyl ester (270 mg; 0.46 mmol) was dissolved in ethanol (10 mL), and aqueous 1 N sodium hydroxide (3 mL) was added. The reaction mixture was stirred for 16 h. acidified with 1 N aqueous hydrochloric acid and extracted with ethyl acetate. The organic phase was dried, evaporated to dryness and purified by prep HPLC (method B). Yield: 128 mg (80%). HPLC-MS: m/z: 475.1 (M+H)+; Rt: 3.06 min.

Example 26

[4-(3-Cyclopentyloxy-5-phenylethynyl-phenylsulfanyl)-2-methyl-phenoxy]-acetic acid

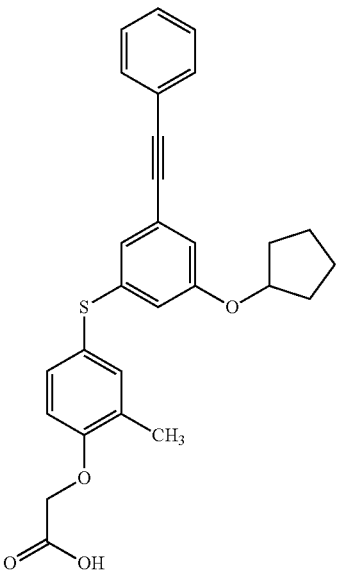 [SMILES: Cc1cc(Sc2cc(C#Cc3ccccc3)cc(OC3CCCC3)c2)ccc1OCC(=O)O]

Step A: [4-(3-Cyclopentyloxy-5-phenylethynyl-phenylsulfanyl)-2-methyl-phenoxy]-acetic acid ethyl ester The title product was prepared from [4-(3-Bromo-5-cyclopentyloxy-phenylsulfanyl)-2-methyl-phenoxy]-acetic acid ethyl ester (250 mg; 0.54 mmol), (phenyl acetylene (110 mg; 1.07 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 186 mg (70%). HPLC-MS: m/z: 487.1 (M+H)+; Rt: 3.17 min.

Step B: [4-(3-Cyclopentyloxy-5-phenylethynyl-phenylsulfanyl)-2-methyl-phenoxy]-acetic acid {[4-(3-Cyclopentyloxy-5-phenylethynyl-phenylsulfanyl)-2-methyl-phenoxy]-acetic acid ethyl ester (270 mg; 0.46 mmol) was dissolved in ethanol (10 mL), and aqueous 1 N sodium hydroxide (3 mL) was added. The reaction mixture was stirred for 16 h. acidified with 1 N aqueous hydrochloric acid and extracted with ethyl acetate. The organic phase was dried, evaporated to dryness and purified by prep HPLC (method B). Yield: 120 mg (69%). HPLC-MS: m/z: 459.1 (M+H)+; Rt: 2.86 min.

Example 27

{4-[3-(4-Fluoro-phenylethynyl)-5-(4-methanesulfonyl-benzyloxy)-phenylsulfanyl]-2-methyl-phenoxy}-acetic acid

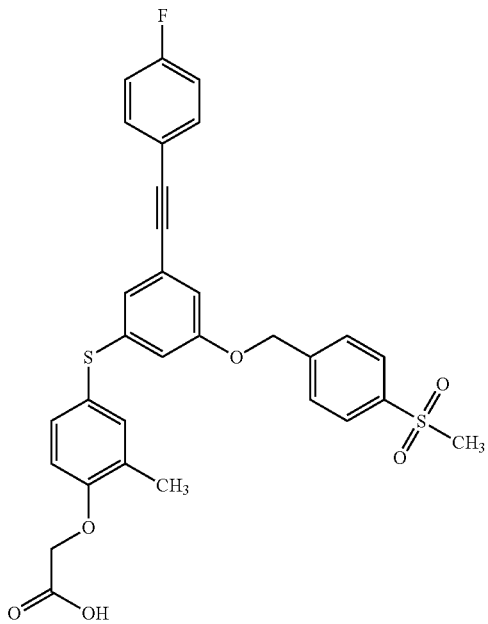 [SMILES: Cc1cc(Sc2cc(C#Cc3ccc(F)cc3)cc(OCc3ccc(S(C)(=O)=O)cc3)c2)ccc1OCC(=O)O]

Step A: {4-[3-(4-Fluoro-phenylethynyl)-5-(4-methanesulfonyl-benzyloxy)-phenyl-sulfanyl]-2-methyl-phenoxy}-acetic acid ethyl ester The title product was prepared from {4-[3-Bromo-5-(4-methanesulfonyl-benzyloxy)-phenylsulfanyl]-2-methyl-phenoxy}-acetic acid ethyl ester (335 mg; 0.59 mmol), 1-ethynyl-4-fluorobenzene (142.3 mg; 1.19 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 140 mg (39%). HPLC-MS: m/z: 605.5 (M+H)+; Rt: 2.80 min.

Step B: {4-[3-(4-Fluoro-phenylethynyl)-5-(4-methanesulfonyl-benzyloxy)-phenyl-sulfanyl]-2-methyl-phenoxy}-acetic acid {4-[3-(4-Fluoro-phenylethynyl)-5-(4-methanesulfonyl-benzyloxy)-phenylsulfanyl]-2-methyl-phenoxy}-acetic acid ethyl ester (270 mg; 0.46 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried, evaporated to dryness and purified by prep HPLC (method B). Yield: 113 mg (85%). HPLC-MS: m/z: 599.4 (M+Na); Rt: 2.50 min.

Example 28

[4-(3-Cyclopentylmethoxy-5-phenylethynyl-phenylsulfanyl)-2-methyl-phenoxy]-acetic acid

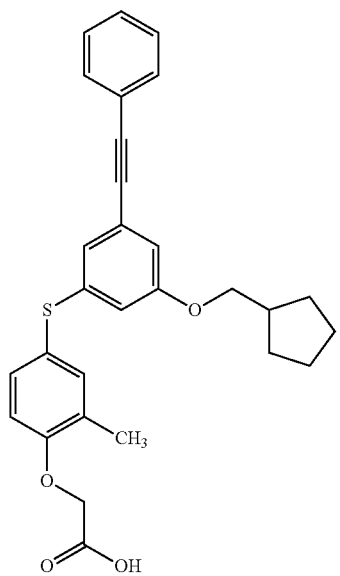 [SMILES: Cc1cc(Sc2cc(C#Cc3ccccc3)cc(OCC3CCCC3)c2)ccc1OCC(=O)O]

Step A: [4-(3-Cyclopentylmethoxy-5-phenylethynyl-phenylsulfanyl)-2-methyl-phenoxy]-acetic acid ethyl ester The title product was prepared from [4-(3-Bromo-5-cyclopentyloxy-phenylsulfanyl)-2-methyl-phenoxy]-acetic acid ethyl ester (300 mg; 0.63 mmol), phenylacetylen (191.7 mg; 1.88 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 200 mg (64%). HPLC-MS: m/z: 500.8 (M)+; Rt: 3.30 min.

Step B: [4-(3-Cyclopentylmethoxy-5-phenylethynyl-phenylsulfanyl)-2-methyl-phenoxy]-acetic acid {[4-(3-Cyclopentylmethoxy-5-phenylethynyl-phenylsulfanyl)-2-methyl-phenoxy]-acetic acid ethyl ester (200 mg; 0.40 mmol) was dissolved in THF (2 mL), ethanol (4 mL), and aqueous 1 N sodium hydroxide (3 mL) was added. The reaction mixture was stirred for 30 min. acidified with 1 N aqueous hydrochloric acid and extracted with ethyl acetate. The organic phase was dried and evaporated to dryness. Yield: 146 mg (78%). HPLC-MS: m/z: 472.9 (M)+; Rt: 3.03 min.

Example 29

{4-[3-(2-Cyclohexyl-ethoxy)-5-phenylethynyl-phenylsulfanyl]-2-methyl-phenoxy}-acetic acid

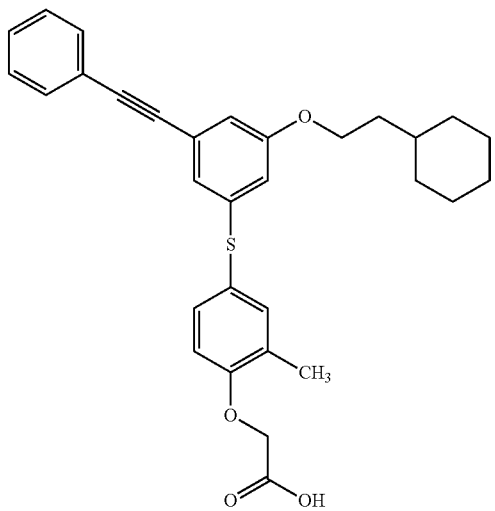 [SMILES: Cc1cc(Sc2cc(C#Cc3ccccc3)cc(OCCC3CCCCC3)c2)ccc1OCC(=O)O]

Step A: {4-[3-(2-Cyclohexyl-ethoxy)-5-phenylethynyl-phenylsulfanyl]-2-methyl-phenoxy}-acetic acid ethyl ester The title product was prepared from {4-[3-Bromo-5-(2-cyclohexyl-ethoxy)-phenylsulfanyl]-2-methyl-phenoxy}-acetic acid ethyl ester (300 mg; 0.58 mmol), phenylacetylen (181.1 mg; 1.8 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 110 mg (33%). HPLC-MS: m/z: 529.6 (M+H)+; Rt: 3.38 min.

Step B: {4-[3-(2-Cyclohexyl-ethoxy)-5-phenylethynyl-phenylsulfanyl]-2-methyl-phenoxy}-acetic acid {4-[3-(2-Cyclohexyl-ethoxy)-5-phenylethynyl-phenylsulfanyl]-2-methyl-phenoxy}-acetic acid ethyl ester (110 mg; 0.208 mmol) was dissolved in THF (2 mL), ethanol (4 mL), and aqueous 1 N sodium hydroxide (3 mL) was added. The reaction mixture was stirred for 30 min. acidified with 1 N aqueous hydrochloric acid and extracted with ethyl acetate. The organic phase was dried and evaporated to dryness. Yield: 105 mg. HPLC-MS: m/z: 500.1 (M)+; Rt: 3.20 min.

Example 30

{4-[3-(2-Ethyl-butoxy)-5-(3-morpholin-4-yl-prop-1-ynyl)-phenylsulfanyl]-2-methyl-phenoxy}-acetic acid

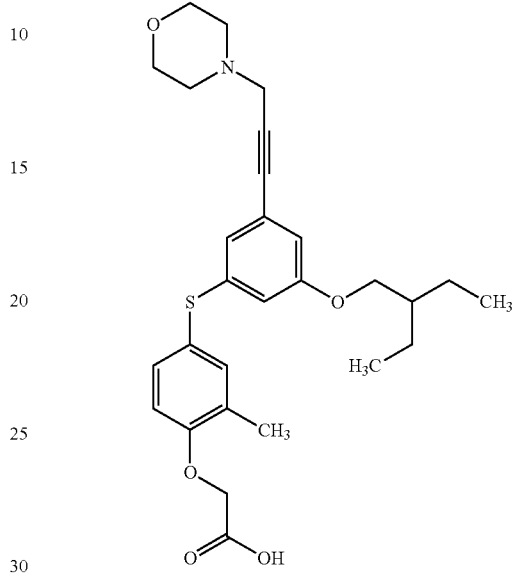

Step A: {4-[3-(2-Ethyl-butoxy)-5-(3-morpholin-4-yl-prop-1-ynyl)-phenylsulfanyl]-2-methyl-phenoxy}-acetic acid ethyl ester The title product was prepared from 4-(3-Bromo-5-cyclopentyloxy-phenylsulfanyl)-2-methyl-phenoxy]-acetic acid ethyl ester (200 mg; 0.42 mmol) and 4-prop-2-ynyl-morpholine (156.0 mg; 1.26 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 210 mg (95%). HPLC-MS: m/z: 526.2 (M+H)+; Rt: 2.23 min

Step B: {4-[3-(2-Ethyl-butoxy)-5-(3-morpholin-4-yl-prop-1-ynyl)-phenylsulfanyl]-2-methyl-phenoxy}-acetic acid {4-[3-(2-Ethyl-butoxy)-5-(3-morpholin-4-yl-prop-1-ynyl)-phenylsulfanyl]-2-methyl-phenoxy}-acetic acid ethyl ester (210 mg; 0.40 mmol) was dissolved in ethanol (10 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 144 mg (73%). HPLC-MS: m/z: 498.2 (M+H)+; Rt: 1.97 min.

Example 31

{4-[3-Cyclopentyloxy-5-(3-morpholin-4-yl-prop-1-ynyl)-phenylsulfanyl]-2-methyl-phenoxy}-acetic acid

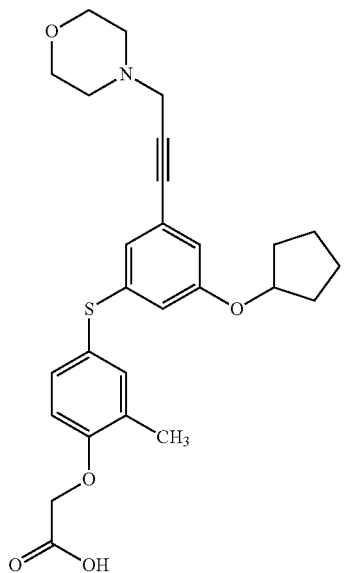 [SMILES: Cc1cc(Sc2cc(C#CCN3CCOCC3)cc(OC3CCCC3)c2)ccc1OCC(=O)O]

Step A: {4-[3-Cyclopentyloxy-5-(3-morpholin-4-yl-prop-1-ynyl)-phenylsulfanyl]-2-methyl-phenoxy}-acetic acid ethyl ester The title product was prepared from [4-(3-Bromo-5-cyclopentyloxy-phenylsulfanyl)-2-methyl-phenoxy]-acetic acid ethyl ester (250 mg; 0.54 mmol) and 4-prop-2-ynyl-morpholine (134.48 mg; 1.07 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 210 mg (95%). HPLC-MS: m/z: 510.2 (M+H)+; Rt: 2.03 min

Step B: {4-[3-Cyclopentyloxy-5-(3-morpholin-4-yl-prop-1-ynyl)-phenylsulfanyl]-2-methyl-phenoxy}-acetic acid {4-[3-Cyclopentyloxy-5-(3-morpholin-4-yl-prop-1-ynyl)-phenylsulfanyl]-2-methyl-phenoxy}-acetic acid ethyl ester (160 mg; 0.31 mmol) was dissolved in ethanol (10 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 105 mg (70%). HPLC-MS: m/z: 482.2 (M+H)+; Rt: 1.77 min.

Example 32

{4-[3-(2-Cyclohexyl-ethoxy)-5-(3-morpholin-4-yl-prop-1-ynyl)-phenylsulfanyl]-2-methyl-phenoxy}-acetic acid

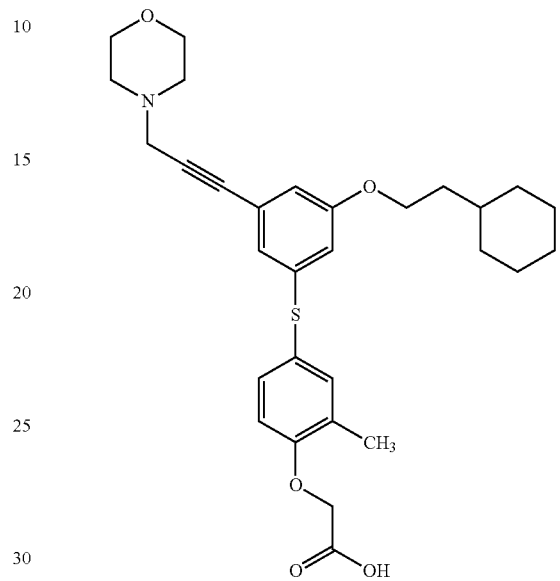

Step A: {4-[3-(2-Cyclohexyl-ethoxy)-5-(3-morpholin-4-yl-prop-1-ynyl)-phenyl-sulfanyl]-2-methyl-phenoxy}-acetic acid ethyl ester The title product was prepared from {4-[3-Bromo-5-(2-cyclohexyl-ethoxy)-phenyl-sulfanyl]-2-methyl-phenoxy}-acetic acid ethyl ester (300 mg; 0.59 mmol) and 4-prop-2-ynyl-morpholine (222.0 mg; 1.77 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 200 mg (30%). HPLC-MS: m/z: 551.8 (M)+; Rt: 2.35 min

Step B: {4-[3-(2-Cyclohexyl-ethoxy)-5-(3-morpholin-4-yl-prop-1-ynyl)-phenyl-sulfanyl]-2-methyl-phenoxy}-acetic acid {4-[3-(2-Cyclohexyl-ethoxy)-5-(3-morpholin-4-yl-prop-1-ynyl)-phenylsulfanyl]-2-methyl-phenoxy}-acetic acid ethyl ester (200 mg; 0.36 mmol) was dissolved in THF (2 mL) and ethanol (4 mL), and aqueous 1 N sodium hydroxide (3 mL) was added. The reaction mixture was stirred for 30 min. acidified with 1 N aqueous hydrochloric acid and extracted with ethyl acetate. The organic phase was dried and evaporated to dryness. Yield: 107 mg (57%). HPLC-MS: m/z: 523.9 (M)+; Rt: 2.06 min.

Example 33

{4-[3-Cyclopentylmethoxy-5-(3-morpholin-4-yl-prop-1-ynyl)-phenylsulfanyl]-2-methyl-phenoxy}-acetic acid

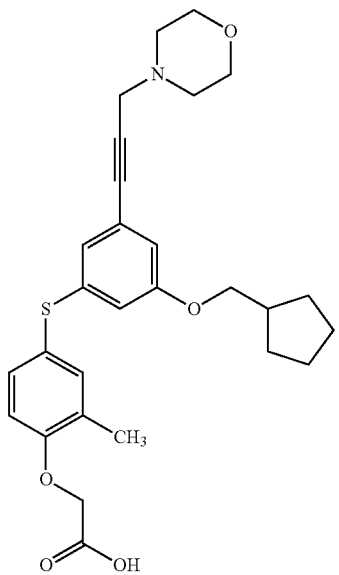 [SMILES: Cc1cc(Sc2cc(C#CCN3CCOCC3)cc(OCC3CCCC3)c2)ccc1OCC(=O)O]

Step A: {4-[3-(2-Cyclohexyl-ethoxy)-5-(3-morpholin-4-yl-prop-1-ynyl)-phenyl-sulfanyl]-2-methyl-phenoxy}-acetic acid ethyl ester The title product was prepared from {4-[3-Bromo-5-cyclopentylmethoxy-phenyl-sulfanyl)-2-methyl-phenoxy]-acetic acid ethyl ester (260 mg; 0.54 mmol) and 4-prop-2-ynyl-morpholine (203.6 mg; 1.63 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 80 mg (28%). HPLC-MS: m/z: 523.9 (M)+; Rt: 2.19 min

Step B: {4-[3-Cyclopentylmethoxy-5-(3-morpholin-4-yl-prop-1-ynyl)-phenylsulfanyl]-2-methyl-phenoxy}-acetic acid {4-[3-Cyclopentylmethoxy-5-(3-morpholin-4-yl-prop-1-ynyl)-phenylsulfanyl]-2-methyl-phenoxy}-acetic acid ethyl ester (80 mg; 0.15 mmol) was dissolved in THF (2 mL) and ethanol (4 mL), and aqueous 1 N sodium hydroxide (3 mL) was added. The reaction mixture was stirred for 30 min. acidified with 1 N aqueous hydrochloric acid and extracted with ethyl acetate. The organic phase was dried and evaporated to dryness. Yield: 43 mg (57%). HPLC-MS: m/z: 495.8 (M)+; Rt: 1.92 min.

Example 34

{4-[3-Cyclopentylmethoxy-5-(3-morpholin-4-yl-prop-1-ynyl)-phenylsulfanyl]-2-methyl-phenoxy}-acetic

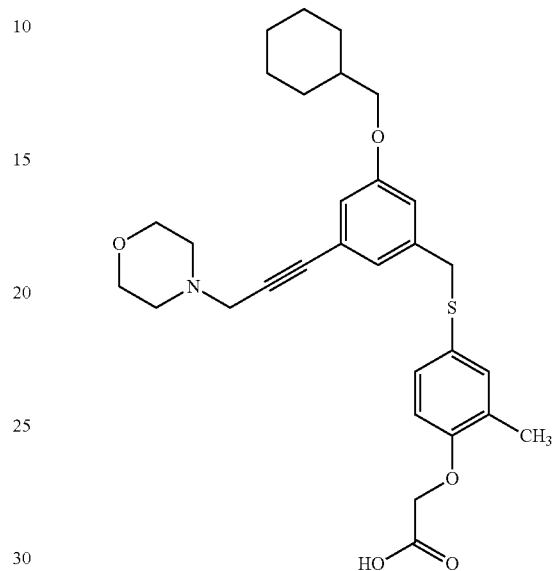

Step A: {4-[3-Cyclopentylmethoxy-5-(3-morpholin-4-yl-prop-1-ynyl)-phenylsulfanyl]-2-methyl-phenoxy}-acetic ethyl ester The title product was prepared from {4-[3-Hydroxy-5-(3-morpholin-4-yl-prop-1-ynyl)-benzylsulfanyl]-2-methyl-phenoxy}-acetic acid ethyl ester (350 mg; 0.77 mmol), cyclohexylmethanol (131.6 mg; 1.15 mmol), tributylphosphine (0.465 mg; 2.31 mmol) and 1,1'-(azodicarbonyl)dipiperidine (0.581 g; 2.31 mmol) were dissolved in THF (50 mL) in a dried reaction flask under an atmosphere of nitrogen. The reaction mixture was stirred for 16 h and purified by column chromatography; ethyl acetate:heptane (5:1). Yield: 120 mg. HPLC-MS: m/z: 552.1 (M+H)+; Rt: 2.19 min.

Step B: {4-[3-Cyclopentylmethoxy-5-(3-morpholin-4-yl-prop-1-ynyl)-phenylsulfanyl]-2-methyl-phenoxy}-acetic {4-[3-Cyclopentylmethoxy-5-(3-morpholin-4-yl-prop-1-ynyl)-phenylsulfanyl]-2-methyl-phenoxy}-acetic ethyl ester (120 mg; 0.22 mmol) was dissolved in THF (2 mL) and ethanol (8 mL), and aqueous 1 N sodium hydroxide (2 mL) was added. The reaction mixture was stirred for 16 h. acidified with 1 N aqueous hydrochloric acid and extracted with ethyl acetate. The organic phase was dried and evaporated to dryness. Yield: 110 mg (90%). HPLC-MS: m/z: 524.2 (M+H)+; Rt: 1.97 min.

Example 35

{4-[3-Isobutoxy-5-(3-morpholin-4-yl-prop-1-ynyl)-benzylsulfanyl]-2-methyl-phenoxy}-acetic acid

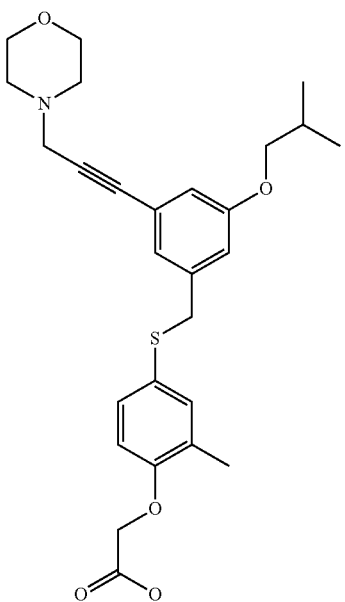 [SMILES: Cc1cc(SCc2cc(C#CCN3CCOCC3)cc(OCC(C)C)c2)ccc1OCC(=O)O]

Step A: {4-[3-Isobutoxy-5-(3-morpholin-4-yl-prop-1-ynyl)-benzylsulfanyl]-2-methyl-phenoxy}-acetic acid ethyl ester The title product was prepared from [4-(3-Bromo-5-isobutoxy-benzylsulfanyl)-2-methyl-phenoxy]-acetic acid ethyl ester (300 mg; 0.64 mmol) and 4-prop-2-ynyl-morpholine (221 mg; 2.6 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 140 mg (44%). HPLC-MS: m/z: 511.9 (M)+; Rt: 2.00 min.

Step B: {4-[3-Isobutoxy-5-(3-morpholin-4-yl-prop-1-ynyl)-benzylsulfanyl]-2-methyl-phenoxy}-acetic acid {{4-[3-Isobutoxy-5-(3-morpholin-4-yl-prop-1-ynyl)-benzylsulfanyl]-2-methyl-phenoxy}-acetic acid ethyl ester (140 mg; 0.27 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness, redissolved in dichloromethane and evaporated to dryness. Yield: 113 mg (86%). HPLC-MS: m/z: 484.9 (M+H)+; Rt: 1.70 min. $\delta_H$ (400 MHz; CDCl$_3$) 1.03 (d, 6H), 2.04-2.12 (m, 1H), 2.24 (s, 3H), 2.90-3.30 (m, 2H), 3.40-3.70 (m, 2H), 3.71 (d, 2H), 3.74 (s, 2H), 3.95-4.05 (m, 4H), 4.17 (s, 2H), 4.69 (s, 2H), 6.14 (m, 1H), 6.53 (d, 1H), 6.77 (dd, 1H), 6.81 (m, 1H), 6.89 (m, 1H), 7.23 (d, 1H).

Example 36

[4-(3-Isobutoxy-5-phenylethynyl-benzylsulfanyl)-2-methyl-phenoxy]-acetic acid

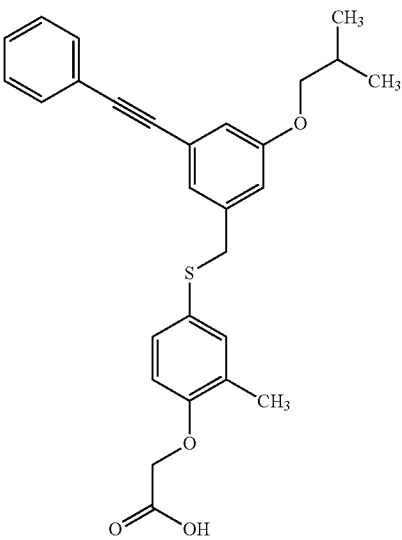 [SMILES: Cc1cc(SCc2cc(C#Cc3ccccc3)cc(OCC(C)C)c2)ccc1OCC(=O)O]

Step A: [4-(3-Isobutoxy-5-phenylethynyl-benzylsulfanyl)-2-methyl-phenoxy]-acetic acid ethyl ester The title product was prepared from [4-(3-Bromo-5-isobutoxy-benzylsulfanyl)-2-methyl-phenoxy]-acetic acid ethyl ester (300 mg; 0.64 mmol) and phenylacetylen (262 mg; 2.6 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 130 mg (45%). HPLC-MS: m/z: 489.1 (M+H)+; Rt: 3.01 min

Step B: [4-(3-Isobutoxy-5-phenylethynyl-benzylsulfanyl)-2-methyl-phenoxy]-acetic acid

[4-(3-Isobutoxy-5-phenylethynyl-benzylsulfanyl)-2-methyl-phenoxy]-acetic acid ethyl ester (130 mg; 0.27 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness, redissolved in dichloromethane and evaporated to dryness. Yield: 120 mg (97%). HPLC-MS: m/z: 461.7 (M+H)+; Rt: 2.82 min.

Example 37

{4-[3-Isobutoxy-5-(4-methanesulfonyl-phenylethynyl)-benzylsulfanyl]-2-methyl-phenoxy}-acetic acid

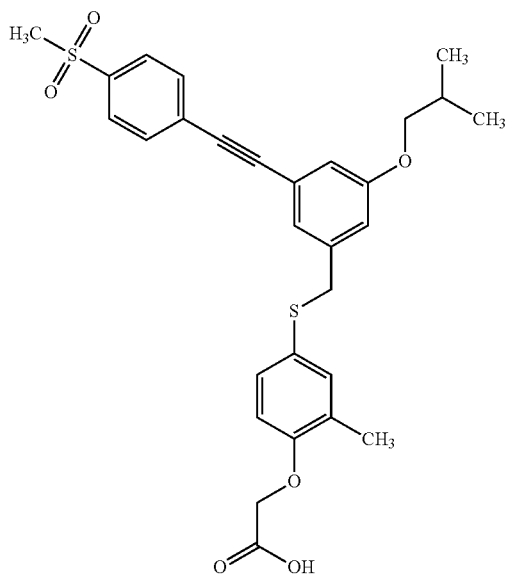 [SMILES: Cc1cc(SCc2cc(C#Cc3ccc(S(C)(=O)=O)cc3)cc(OCC(C)C)c2)ccc1OCC(=O)O]

Step A: [{4-[3-Isobutoxy-5-(4-methanesulfonyl-phenylethynyl)-benzylsulfanyl]-2-methyl-phenoxy}-acetic acid ethyl ester The title product was prepared from [4-(3-Bromo-5-isobutoxy-benzylsulfanyl)-2-methyl-phenoxy]-acetic acid ethyl ester (300 mg; 0.64 mmol) and 1-Ethynyl-4-methanesulfonyl-benzene (347.0 mg; 1.93 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method A). Yield: 260 mg (72%). HPLC-MS: m/z: 567.6 (M+H)+; Rt: 2.77 min Step B: {4-[3-Isobutoxy-5-(4-methanesulfonyl-phenylethynyl)-benzylsulfanyl]-2-methyl-phenoxy}-acetic acid {4-[3-Isobutoxy-5-(4-methanesulfonyl-phenylethynyl)-benzylsulfanyl]-2-methyl-phenoxy}-acetic acid ethyl ester (130 mg; 0.27 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness, redissolved in dichloromethane and evaporated to dryness. Yield: 230 mg (%). HPLC-MS: m/z: 539.5 (M+H)+; Rt: 2.49 min.

Example 38

{4-[3-(4-Methanesulfonyl-phenylethynyl)-5-(5-trifluoromethyl-pyridin-2-yloxy)-phenylsulfanyl]-2-methyl-phenoxy}-acetic acid

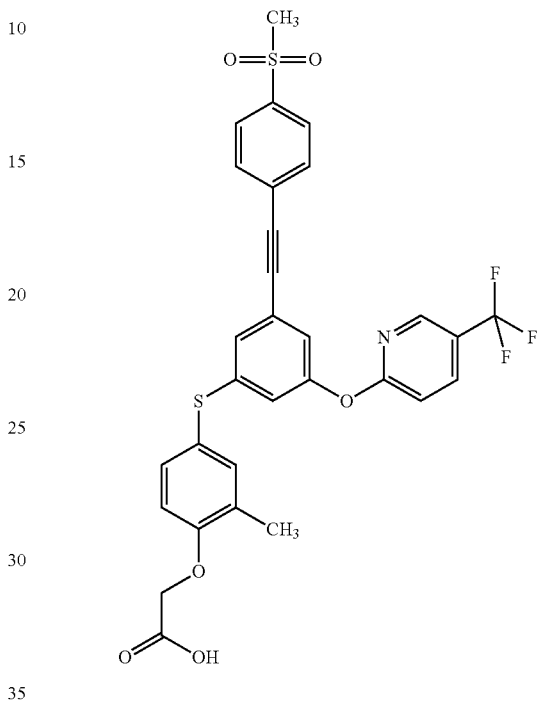

Step A: {4-[3-(4-Methanesulfonyl-phenylethynyl)-5-(5-trifluoromethyl-pyridin-2-yloxy)-phenylsulfanyl]-2-methyl-phenoxy}-acetic acid ethyl ester The title product was prepared from {4-[3-Bromo-5-(5-trifluoromethyl-pyridin-2-yloxy)-phenylsulfanyl]-2-methyl-phenoxy}-acetic acid ethyl ester (250 mg; 0.46 mmol) and 1-Ethynyl-4-methanesulfonyl-benzene (249.2 mg; 1.38 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 168 mg (57%). HPLC-MS: m/z: 642.1 (M+H)+; Rt: 2.75 min Step B: {4-[3-(4-Methanesulfonyl-phenylethynyl)-5-(5-trifluoromethyl-pyridin-2-yloxy)-phenylsulfanyl]-2-methyl-phenoxy}-acetic acid {{4-[3-(4-Methanesulfonyl-phenylethynyl)-5-(5-trifluoromethyl-pyridin-2-yloxy)-phenylsulfanyl]-2-methyl-phenoxy}-acetic acid ethyl ester (168 mg; 0.26 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 120 mg (75%). HPLC-MS: m/z: 614.1 (M+H)+; Rt: 2.45 min.

Example 39

{4-[3-(4-Methanesulfonyl-phenylethynyl)-5-(3-trifluoromethyl-pyridin-2-yloxy)-phenylsulfanyl]-2-methyl-phenoxy}-acetic acid

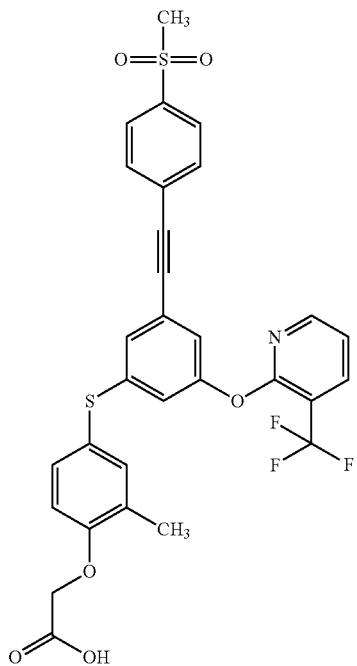 [SMILES: Cc1cc(Sc2cc(C#Cc3ccc(S(C)(=O)=O)cc3)cc(Oc3ncccc3C(F)(F)F)c2)ccc1OCC(=O)O]

Step A: {4-[3-(4-Methanesulfonyl-phenylethynyl)-5-(3-trifluoromethyl-pyridin-2-yloxy)-phenylsulfanyl]-2-methyl-phenoxy}-acetic acid ethyl ester The title product was prepared from {4-[3-Bromo-5-(3-trifluoromethyl-pyridin-2-yloxy)-phenylsulfanyl]-2-methyl-phenoxy}-acetic acid ethyl ester (250 mg; 0.46 mmol) and 1-Ethynyl-4-methanesulfonyl-benzene (249.2 mg; 1.38 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 197 mg (67%). HPLC-MS: m/z: 642.4 (M+H)+; Rt: 2.73 min Step B: {4-[3-(4-Methanesulfonyl-phenylethynyl)-5-(3-trifluoromethyl-pyridin-2-yloxy)-phenylsulfanyl]-2-methyl-phenoxy}-acetic acid {4-[3-(4-Methanesulfonyl-phenylethynyl)-5-(3-trifluoromethyl-pyridin-2-yloxy)-phenylsulfanyl]-2-methyl-phenoxy}-acetic acid ethyl ester (197 mg; 0.31 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 150 mg (80%). HPLC-MS: m/z: 614.4 (M+H)+; Rt: 2.42 min.

Example 40

{2-Methyl-4-[3-(3-morpholin-4-yl-prop-1-ynyl)-5-(3-trifluoromethyl-pyridin-2-yloxy)-phenylsulfanyl]-phenoxy}-acetic acid

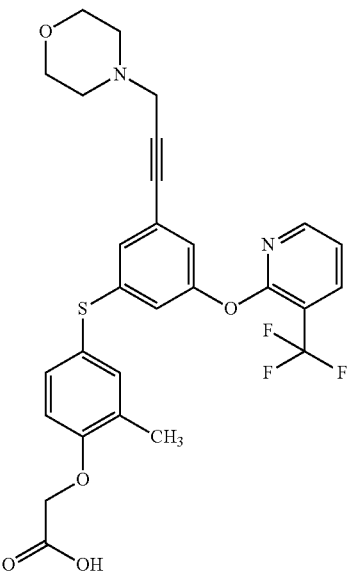 [SMILES: Cc1cc(Sc2cc(C#CCN3CCOCC3)cc(Oc3ncccc3C(F)(F)F)c2)ccc1OCC(=O)O]

Step A: {2-Methyl-4-[3-(3-morpholin-4-yl-prop-1-ynyl)-5-(3-trifluoromethyl-pyridin-2-yloxy)-phenylsulfanyl]-phenoxy}-acetic acid ethyl ester The title product was prepared from {4-[3-Bromo-5-(3-trifluoromethyl-pyridin-2-yloxy)-phenylsulfanyl]-2-methyl-phenoxy}-acetic acid ethyl ester (250 mg; 0.46 mmol) and 4-prop-2-ynyl-morpholine (173.09 mg; 1.38 mmol) applying the procedure described for {4-[3-[2-(4-Chloro-phenyl)-ethoxy]-5-(4-hydroxymethyl-phenylethynyl)-phenylsulfanyl]-2-methylphenoxy}-acetic acid ethyl ester. The crude product was purified by preparative HPLC (method B). Yield: 262 mg (97%). HPLC-MS: m/z: 587.5 (M+H)+; Rt: 2.03 min Step B: {2-Methyl-4-[3-(3-morpholin-4-yl-prop-1-ynyl)-5-(3-trifluoromethyl-pyridin-2-yloxy)-phenylsulfanyl]-phenoxy}-acetic acid {2-Methyl-4-[3-(3-morpholin-4-yl-prop-1-ynyl)-5-(3-trifluoromethyl-pyridin-2-yloxy)-phenylsulfanyl]-phenoxy}-acetic acid ethyl ester (262 mg; 0.45 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 178 mg (72%). HPLC-MS: m/z: 559.5 (M+H)+; Rt: 1.78 min.

Example 41

{2-Methyl-4-[3-(3-morpholin-4-yl-prop-1-ynyl)-5-(5-trifluoromethyl-pyridin-2-yloxy)-phenylsulfanyl]-phenoxy}-acetic acid

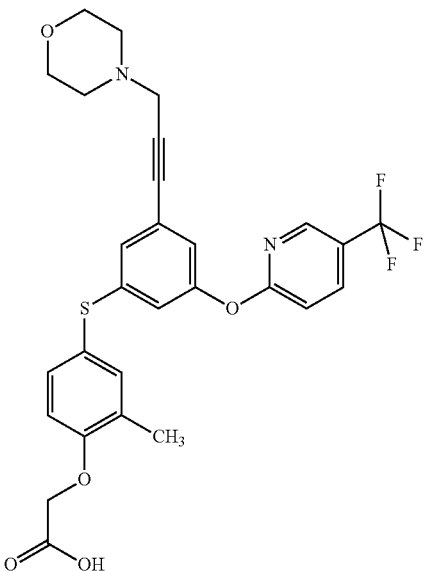 [SMILES: Cc1cc(Sc2cc(C#CCN3CCOCC3)cc(Oc3ccc(C(F)(F)F)cn3)c2)ccc1OCC(=O)O]

Step A: {2-Methyl-4-[3-(3-morpholin-4-yl-prop-1-ynyl)-5-(5-trifluoromethyl-pyridin-2-yloxy)-phenylsulfanyl]-phenoxy}-acetic acid ethyl ester The title product was prepared from {4-[3-Bromo-5-(5-trifluoromethyl-pyridin-2-yloxy)-phenylsulfanyl]-2-methyl-phenoxy}-acetic acid ethyl ester (250 mg; 0.46 mmol) and 4-prop-2-ynyl-morpholine (173.09 mg; 1.38 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 270 mg (100%). HPLC-MS: m/z: 587.5 (M+H)+; Rt: 2.03 min

Step B: {2-Methyl-4-[3-(3-morpholin-4-yl-prop-1-ynyl)-5-(5-trifluoromethyl-pyridin-2-yloxy)-phenylsulfanyl]-phenoxy}-acetic acid {2-Methyl-4-[3-(3-morpholin-4-yl-prop-1-ynyl)-5-(5-trifluoromethyl-pyridin-2-yloxy)-phenylsulfanyl]-phenoxy}-acetic acid ethyl ester (262 mg; 0.45 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 174 mg (68%). HPLC-MS: m/z: 559.5 (M+H)+; Rt: 1.81 min.

Example 42

{2-Methyl-4-[3-(3-morpholin-4-yl-prop-1-ynyl)-5-(3-trifluoromethyl-phenoxy)-phenylsulfanyl]-phenoxy}-acetic acid

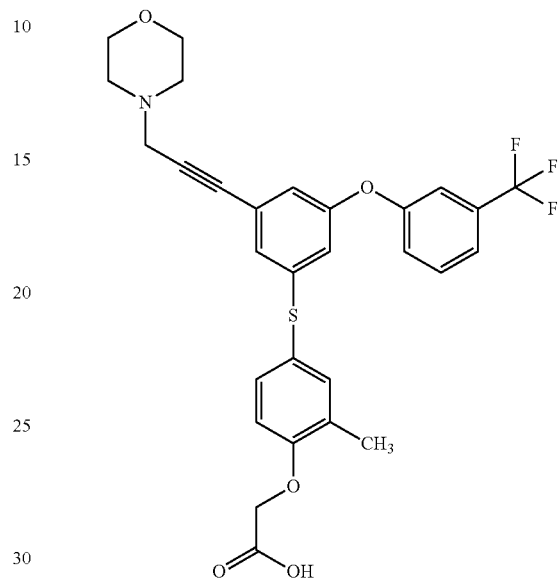

Step A: {2-Methyl-4-[3-(3-morpholin-4-yl-prop-1-ynyl)-5-(3-trifluoromethyl-phenoxy)-phenylsulfanyl]-phenoxy}-acetic acid ethyl ester The title product was prepared from {4-[3-Bromo-5-(3-trifluoromethyl-phenoxy)-phenylsulfanyl]-2-methyl-phenoxy}-acetic acid ethyl ester (230 mg; 0.43 mmol) and 4-prop-2-ynyl-morpholine (159.5 mg; 1.28 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method A). Yield: 160 mg. HPLC-MS: m/z: 586.5 (M+H)+; Rt: 2.18 min

Step B: {2-Methyl-4-[3-(3-morpholin-4-yl-prop-1-ynyl)-5-(3-trifluoromethyl-phenoxy)-phenylsulfanyl]-phenoxy}-acetic acid {2-Methyl-4-[3-(3-morpholin-4-yl-prop-1-ynyl)-5-(3-trifluoromethyl-phenoxy)-phenylsulfanyl]-phenoxy}-acetic acid ethyl ester (160 mg; 0.27 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 128 mg (84%). HPLC-MS: m/z: 558.4 (M+H)+; Rt: 1.91 min. $\delta_H$ (400 MHz; CDCl$_3$) 2.26 (s, 3H), 3.05-3.55 (m, 4H), 3.91-4.04 (m, 4H), 4.11 (s, 2H), 4.70 (s, 2H), 6.71-6.78 (m, 3H), 6.81-6.84 (m, 1H), 7.11-7.16 (m, 1H), 7.19-7.23 (m, 1H), 7.27-7.33 (m, 2H), 7.37-7.41 (m, 1H), 7.43-7.49 (m, 1H).

Example 43

{4-[3-(4-Methanesulfonyl-phenylethynyl)-5-(3-trif-luoromethyl-phenoxy)-phenylsulfanyl]-2-methyl-phenoxy}-acetic acid

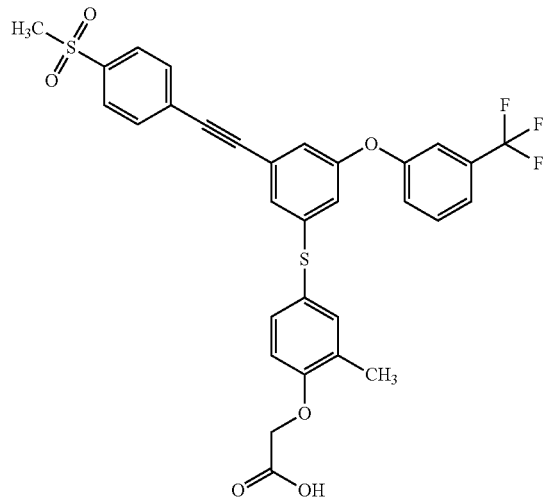 [SMILES: Cc1cc(Sc2cc(C#Cc3ccc(S(C)(=O)=O)cc3)cc(Oc3cccc(C(F)(F)F)c3)c2)ccc1OCC(=O)O]

Step A: {4-[3-(4-Methanesulfonyl-phenylethynyl)-5-(3-trifluoromethyl-phenoxy)-phenylsulfanyl]-2-methyl-phenoxy}-acetic acid ethyl ester The title product was prepared from {4-[3-Bromo-5-(3-trifluoromethyl-phenoxy)-phenylsulfanyl]-2-methyl-phenoxy}-acetic acid ethyl ester (230 mg; 0.43 mmol) and 1-Ethynyl-4-methanesulfonyl-benzene (229.7 mg; 1.28 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method A). Yield: 140 mg. HPLC-MS: m/z: 641.5 (M+H)+; Rt: 2.89 min

Step B: {4-[3-(4-Methanesulfonyl-phenylethynyl)-5-(3-trifluoromethyl-phenoxy)-phenylsulfanyl]-2-methyl-phenoxy}-acetic acid {4-[3-(4-Methanesulfonyl-phenylethynyl)-5-(3-trifluoromethyl-phenoxy)-phenyl-sulfanyl]-2-methyl-phenoxy}-acetic acid ethyl ester (140 mg; 0.22 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate, dried and evaporated to dryness. The organic phase was purified by preparative HPLC (method B). Yield: 100 mg (75%). HPLC-MS: m/z: 635.1 (M+Na); Rt: 2.62 min.

Example 44

{2-Methyl-4-[3-phenylethynyl-5-(5-trifluoromethyl-pyridin-2-yloxy)-phenylsulfanyl]-phenoxy}-acetic acid

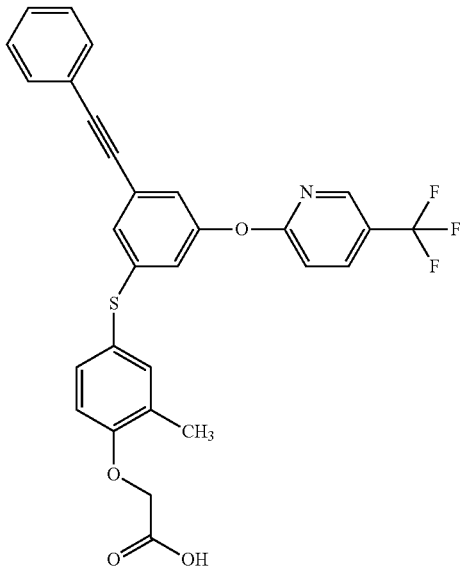 [SMILES: Cc1cc(Sc2cc(C#Cc3ccccc3)cc(Oc3ccc(C(F)(F)F)cn3)c2)ccc1OCC(=O)O]

Step A: {2-Methyl-4-[3-phenylethynyl-5-(5-trifluoromethyl-pyridin-2-yloxy)-phenylsulfanyl]-phenoxy}-acetic acid ethyl ester The title product was prepared from {4-[3-Bromo-5-(3-trifluoromethyl-phenoxy)-phenylsulfanyl]-2-methyl-phenoxy}-acetic acid ethyl ester (300 mg; 0.55 mmol) and phenylacetylene (113 mg; 1.11 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method A). Yield: 150 mg. HPLC-MS: m/z: 564.5 (M+H)+; Rt: 3.00 min

Step B: {2-Methyl-4-[3-phenylethynyl-5-(5-trifluoromethyl-pyridin-2-yloxy)-phenylsulfanyl]-phenoxy}-acetic acid {2-Methyl-4-[3-phenylethynyl-5-(5-trifluoromethyl-pyridin-2-yloxy)-phenylsulfanyl]-phenoxy}-acetic acid ethyl ester (150 mg; 0.266 mmol) was dissolved in THF (2 mL) and ethanol (4 mL), and aqueous 1 N sodium hydroxide (3 mL) was added. The reaction mixture was stirred for ½ h. acidified with 5% aqueous citric acid and extracted with ethyl acetate, dried and evaporated to dryness. Yield: 100 mg (75%). HPLC-MS: m/z: 535.7 (M)+; Rt: 2.78 min.

Example 45

{4-[3-Cyclopropylmethoxy-5-(3-morpholin-4-yl-prop-1-ynyl)-benzylsulfanyl]-2-methyl-phenoxy}-acetic acid

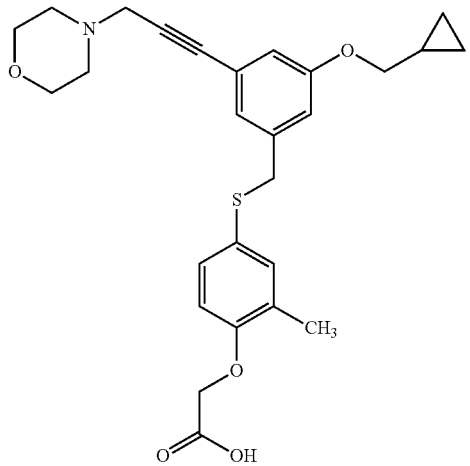 [SMILES: Cc1cc(SCc2cc(C#CCN3CCOCC3)cc(OCC3CC3)c2)ccc1OCC(=O)O]

Step A: {4-[3-Cyclopropylmethoxy-5-(3-morpholin-4-yl-prop-1-ynyl)-benzylsulfanyl]-2-methyl-phenoxy}-acetic acid acid ethyl ester The title product was prepared from [4-(3-Bromo-5-cyclopropylmethoxy-benzylsulfanyl)-2-methyl-phenoxy]-acetic acid ethyl ester (200 mg; 0.43 mmol) and 4-prop-2-ynyl-morpholine (161 mg; 1.3 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 173 mg; 79%. HPLC-MS: m/z: 510.1 (M)+; Rt: 1.9 min.

Step B: {4-[3-Cyclopropylmethoxy-5-(3-morpholin-4-yl-prop-1-ynyl)-benzylsulfanyl]-2-methyl-phenoxy}-acetic acid {4-[3-Cyclopropylmethoxy-5-(3-morpholin-4-yl-prop-1-ynyl)-benzylsulfanyl]-2-methyl-phenoxy}-acetic acid acid ethyl ester (173 mg; 0.34 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness. Yield: 107 mg; 66%. HPLC-MS: m/z: 482.0 (M+H)+; Rt: 1.62 min.

Example 46

{4-[3-Cyclopropylmethoxy-5-(3-morpholin-4-yl-prop-1-ynyl)-phenylsulfanyl]-2-methyl-phenoxy}-acetic acid

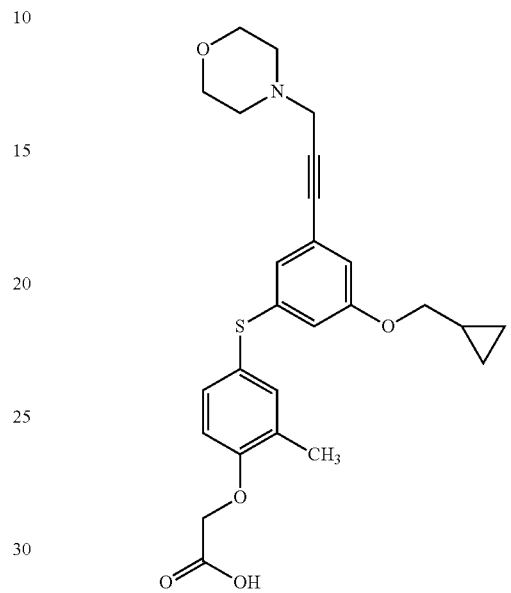

Step A: {4-[3-Cyclopropylmethoxy-5-(3-morpholin-4-yl-prop-1-ynyl)-phenylsulfanyl]-2-methyl-phenoxy}-acetic acid ethyl ester The title product was prepared from [4-(3-Bromo-5-cyclopropylmethoxy-phenyl-sulfanyl)-2-methyl-phenoxy]-acetic acid ethyl ester (250 mg; 0.55 mmol) and 4-prop-2-ynyl-morpholine (208 mg; 1.7 mmol) applying the procedure described for {4-[3-[2-(4-Chlorophenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 205 mg; 75%. HPLC-MS: m/z: 496.1 (M+H)+; Rt: 2.04 min.

Step B: {4-[3-Cyclopropylmethoxy-5-(3-morpholin-4-yl-prop-1-ynyl)-phenylsulfanyl]-2-methyl-phenoxy}-acetic acid {4-[3-Cyclopropylmethoxy-5-(3-morpholin-4-yl-prop-1-ynyl)-phenylsulfanyl]-2-methyl-phenoxy}-acetic acid ethyl ester (205 mg; 0.41 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness. Yield: 160 mg; 83%. HPLC-MS: m/z: 468.1 (M+H)+; Rt: 1.78 min.

Example 47

{4-[3-Isobutoxy-5-(3-morpholin-4-yl-prop-1-ynyl)-phenylsulfanyl]-2,5-dimethyl-phenoxy}-acetic acid

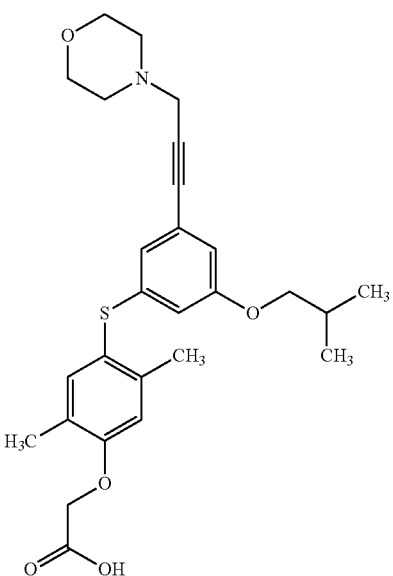 [SMILES: Cc1cc(Sc2cc(C#CCN3CCOCC3)cc(OCC(C)C)c2)c(C)cc1OCC(=O)O]

Step A: {4-[3-Isobutoxy-5-(3-morpholin-4-yl-prop-1-ynyl)-phenylsulfanyl]-2,5-dimethyl-phenoxy}-acetic acid ethyl ester The title product was prepared from [4-(3-Bromo-5-isobutoxy-phenylsulfanyl)-2,5-dimethyl-phenoxy]-acetic acid ethyl ester (400 mg; 0.86 mmol) and 4-prop-2-ynyl-morpholine (321.3 mg; 2.6 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 350 mg; 80%. HPLC-MS: m/z: 512.2 (M+H)+; Rt: 2.09 min.

Step B: {4-[3-Isobutoxy-5-(3-morpholin-4-yl-prop-1-ynyl)-phenylsulfanyl]-2,5-dimethyl-phenoxy}-acetic acid {4-[3-Isobutoxy-5-(3-morpholin-4-yl-prop-1-ynyl)-phenylsulfanyl]-2,5-dimethyl-phenoxy}-acetic acid ethyl ester (350 mg; 0.68 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 250 mg; 76%. HPLC-MS: m/z: 484.6 (M+H)+; Rt: 1.87 min.

Example 48

{4-[3-Isobutoxy-5-(3-morpholin-4-yl-prop-1-ynyl)-phenoxy]-2-methyl-phenoxy}-acetic acid

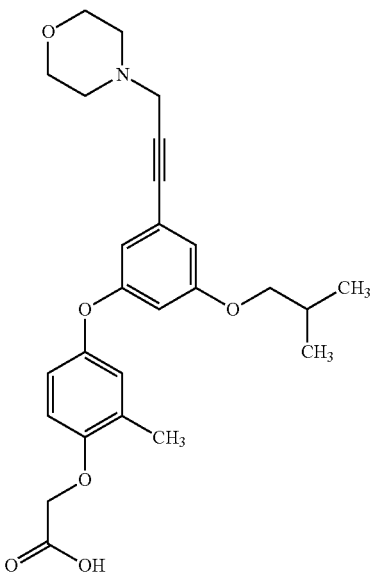 [SMILES: Cc1cc(Oc2cc(C#CCN3CCOCC3)cc(OCC(C)C)c2)ccc1OCC(=O)O]

Step A: {4-[3-Isobutoxy-5-(3-morpholin-4-yl-prop-1-ynyl)-phenoxy]-2-methyl-phenoxy}-acetic acid ethyl ester The title product was prepared from [4-(3-Bromo-5-isobutoxy-phenylsulfanyl)-2,5-dimethyl-phenoxy]-acetic acid ethyl ester (300 mg; 0.71 mmol) and 4-prop-2-ynyl-morpholine (266.1 mg; 2.1 mmol) applying the procedure described for {4-[3-[2-(4-Chloro-phenyl)-ethoxy]-5-(4-hydroxymethyl-phenylethynyl)-phenylsulfanyl]-2-methyl-phenoxy}-acetic acid ethyl ester. The crude product was purified by preparative HPLC (method B). Yield: 260 mg; 79%. HPLC-MS: m/z: 468.7 (M+H)+; Rt: 1.94 min Step B: {4-[3-Isobutoxy-5-(3-morpholin-4-yl-prop-1-ynyl)-phenoxy]-2-methyl-phenoxy}-acetic acid {4-[3-Isobutoxy-5-(3-morpholin-4-yl-prop-1-ynyl)-phenoxy]-2-methyl-phenoxy}-acetic acid ethyl ester (260 mg; 0.56 mmol) was dissolved in ethanol (15 mL), and aqueous 1 N sodium hydroxide (3 mL) was added. The reaction mixture was stirred for 16 h. acidified with 1 N aqueous hydrochloric acid and extracted with ethyl acetate. The organic phase was dried and evaporated to dryness and purified by prep HPLC (method B). Yield: 180 mg; 72%. HPLC-MS: m/z: 454.6 (M+H)+; Rt: 1.77 min. $\delta_H$ (400 MHz; CDCl$_3$) 1.01 (d, 6H), 2.02-2.10 (m, 1H), 2.28 (s, 3H), 3.10-3.55 (m, 4H), 3.68 (d, 2H), 3.93-4.07 (m, 4H), 4.10 (s, 2H), 4.67 (s, 2H), 6.47 (m, 1H), 6.57-6.59 (m, 1H), 6.66-6.69 (m, 1H), 6.71 (d, 1H), 6.79 (dd, 1H), 6.86 (d, 1H).

Pharmacological Methods
In Vitro PPAR-δ Activation Activity
The PPAR transient transactivation assay is based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50-80% at transfection. A total of 0.8 µg DNA containing 0.64 µg pM1α/γLBD, 0.1 µg pCMVβGal, 0.08 µg pGL2(Gal4)₅ and 0.02 µg pADVANTAGE was transfected per well using FuGene transfection reagent according to the manufacturers instructions (Roche). Cells were allowed to express protein for 48 h followed by addition of compound.

Plasmids: Human PPAR-δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARδ: aa 128-C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (Webster et al. (1988), Nucleic Acids Res. 16, 8192) into the vector pGL2 promotor (Promega) generating the plasmid pGL2(GAL4)₅. pCMVβGal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments.

Luciferase assay: Medium including test compound was aspirated and 100 µl PBS incl. 1 mM Mg++ and Ca++ were added to each well. The luciferase assay was performed using the LucLite kit according to the manufacturer's instructions (Packard Instruments). Light emission was quantified by counting on a Packard LumiCounter. To measure β-galactosidase activity 25 µl supernatant from each transfection lysate was transferred to a new microplate. β-Galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.).

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated for PPAR-δ mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately ans in any combination thereof be material for realising the invention in diverse forms thereof.

Preferred Features of the Invention:

1. A compound of formula I:

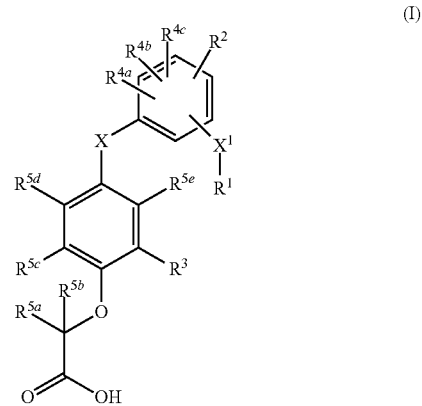

(I)

or a pharmaceutically acceptable salt thereof, wherein:

X is selected from O, S, OCH₂, and SCH₂;

X¹ is O or S;

R¹ is selected from H, $C_{1-8}$ alkyl, $C_{2-8}$ alkenyl, aryl, heteroaryl, $C_{3-10}$ cycloalkyl, and a heterocyclyl, wherein each R¹ group is substituted with 0-4 $R^{1a}$;

$R^{1a}$, at each occurrence, is selected from S substituted with 0-1 $R^{1b}$, O substituted with 0-1 $R^{1b}$, halogen, NH₂ substituted with 0-2 $R^{1b}$, —CN, NO₂, $C_{1-6}$ alkyl substituted with 0-3 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, heteroaryl substituted with 0-2 $R^{1b}$, $C_{3-10}$ cycloalkyl substituted with 0-2 $R^{1b}$, and heterocycle substituted with 0-2 $R^{1b}$;

$R^{1b}$, at each occurrence, is selected from S substituted with 0-1 $R^{1c}$, O substituted with 0-1 $R^{1c}$, halogen, methanesulfonyl, NH₂ substituted with 0-2 $R^{1c}$, —CN, NO₂, $C_{1-6}$ alkyl substituted with 0-3 $R^{1c}$, $C_{2-6}$ alkenyl substituted with 0-2

$R^{1c}$, aryl substituted with 0-2 $R^{1c}$, heteroaryl substituted with 0-2 $R^{1c}$, $C_{3-10}$ cycloalkyl substituted with 0-2 $R^{1c}$, and a heterocycle substituted with 0-2 $R^{1c}$;

$R^{1c}$, at each occurrence, is selected from S substituted with 0-1 $R^{1d}$, O substituted with 0-1 $R^{1d}$, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, heteroaryl substituted with 0-2 $R^{1d}$, $C_{3-10}$ cycloalkyl substituted with 0-2 $R^{1d}$, and a heterocycle substituted with 0-2 $R^{1d}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH═CH—$R^{2a}$, aryl substituted with 0-3 $R^{2a}$, and heteroaryl substituted with 0-3 $R^{2a}$;

$R^{2a}$, at each occurrence, is selected from S substituted with 0-1 $R^{2b}$, O substituted with 0-1 $R^{2b}$, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, heteroaryl substituted with 0-2 $R^{2b}$, $C_{3-10}$ cycloalkyl substituted with 0-2 $R^{2b}$, and a heterocycle substituted with 0-2;

$R^{2b}$, at each occurrence, is selected from S substituted with 0-1 $R^{2c}$, O substituted with 0-1 $R^{2c}$, halogen, methanesulfonyl, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, heteroaryl substituted with 0-2 $R^{2c}$, $C_{3-10}$ cycloalkyl substituted with 0-2 $R^{2c}$, and a heterocycle substituted with 0-2 $R^{2c}$;

$R^{2c}$, at each occurrence, is selected from S substituted with 0-1 $R^{2d}$, O substituted with 0-1 $R^{2d}$, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, heteroaryl substituted with 0-2 $R^{2d}$, $C_{3-10}$ cycloalkyl substituted with 0-2 $R^{2d}$, and a heterocycle substituted with 0-2 $R^{2d}$ $R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH—C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and N($C_{1-4}$ alkyl)$_2$;

$R^{4b}$, at each occurrence, is selected from H, halogen, and $C_{1-6}$ alkyl substituted with 0-2 $R^{4e}$;

$R^{4e}$, at each occurrence, is selected from OH, O, halogen, $NH_2$, NH—$C_{1-4}$ alkyl, and N($C_{1-4}$ alkyl)$_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and N($C_{1-4}$ alkyl)$_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

2. A compound of clause 1 wherein:

X is selected from O, S, $OCH_2$, and $SCH_2$;

$X^1$ is O or S;

$R^1$ is selected from H, $C_{1-8}$ alkyl, $C_{2-8}$ alkenyl, aryl, 5-10 membered heteroaryl consisting of carbon atoms and 1-4 heteroatoms selected from O, N, and $S(O)_{0-2}$, $C_{3-10}$ cycloalkyl, and a 3-8 membered heterocycle consisting of carbon atoms and 1-3 heteroatoms selected from O, N, and $S(O)_{0-2}$, wherein each $R^1$ group is substituted with 0-4 $R^{1a}$;

$R^{1a}$, at each occurrence, is selected from OH substituted with 0-1 $R^{1b}$, SH substituted with 0-1 $R^{1b}$, S, O, halogen, $NH_2$ substituted with 0-2 $R^{1b}$, —CN, $NO_2$, $C_{1-6}$ alkyl substituted with 0-3 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-3 heteroatoms selected from O, N, and $S(O)_{0-2}$;

$R^{1b}$, at each occurrence, is selected from OH substituted with 0-1 $R^{1c}$, SH substituted with 0-1 $R^{1c}$, S, O, halogen, methanesulfonyl, $NH_2$ substituted with 0-2 $R^{1c}$, —CN, $NO_2$, $C_{1-6}$ alkyl substituted with 0-3 $R^{1c}$, $C_{2-6}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-10}$ cycloalkyl substituted with 0-2 $R^{1c}$, and a 3-8 membered heterocycle substituted with 0-2 $R^{1c}$ and consisting of carbon atoms and 1-3 heteroatoms selected from O, N, and $S(O)_{0-2}$;

$R^{1c}$, at each occurrence, is selected from OH substituted with 0-1 $R^{1d}$, SH substituted with 0-1 $R^{1d}$, S, O, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-10}$ cycloalkyl substituted with 0-2 $R^{1d}$, and a 3-8 membered heterocycle substituted with 0-2 $R^{1d}$ and consisting of carbon atoms and 1-3 heteroatoms selected from O, N, and $S(O)_{0-2}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH═CH—$R^{2a}$ substituted with 0-2 $R^{2a}$, aryl substituted with 0-3 $R^{2a}$, and 5-10 membered heteroaryl substituted with 0-3 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, S, O, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-10}$ cycloalkyl substituted with 0-2 $R^{2b}$, and a 3-8 membered heterocycle substituted with 0-2 $R^{2b}$ and consisting of carbon atoms and 1-3 heteroatoms selected from O, N, and $S(O)_{0-2}$;

$R^{2b}$, at each occurrence, is selected from OH substituted with 0-1 $R^{2c}$, SH substituted with 0-1 $R^{2c}$, S, O substituted with 0-1 $R^{2c}$, halogen, methanesulfonyl, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-10}$ cycloalkyl substituted with 0-2 $R^{2c}$, and a 3-8 membered heterocycle substituted with 0-2 $R^{2c}$ and consisting of carbon atoms and 1-3 heteroatoms selected from O, N, and $S(O)_{0-2}$;

$R^{2c}$, at each occurrence, is selected from OH substituted with 0-1 $R^{2d}$, SH substituted with 0-1 $R^{2d}$, S, O, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, 5-10 membered heteroaryl substituted with 0-2 $R^{2d}$ and consisting of carbon atoms and 1-4 heteroatoms selected from O, N, and $S(O)_{0-2}$, $C_{3-10}$ cycloalkyl substituted with 0-2 $R^{2d}$, and a 3-8 membered heterocycle substituted with 0-2 $R^{2d}$ and consisting of carbon atoms and 1-3 heteroatoms selected from O, N, and $S(O)_{0-2}$;

$R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH$—$C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and $N(C_{1-4}$ alkyl$)_2$;

$R^{4b}$, at each occurrence, is selected from H, halogen, and $C_{1-6}$ alkyl substituted with 0-2 $R^{4e}$;

$R^{4e}$, at each occurrence, is selected from OH, O, halogen, $NH_2$, NH—$C_{1-4}$ alkyl, and $N(C_{1-4}$ alkyl$)_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and $N(C_{1-4}$ alkyl$)_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

3. A compound of clause 1 or 2 wherein:

X is selected from O, S, $OCH_2$, and $SCH_2$;

$X^1$ is O or S;

$R^1$ is selected from H, $C_{1-8}$ alkyl, $C_{2-8}$ alkenyl, aryl, 5-10 membered heteroaryl consisting of carbon atoms and 1-4 heteroatoms selected from O, N, and $S(O)_{0-2}$, $C_{3-10}$ cycloalkyl, and a 3-8 membered heterocycle consisting of carbon atoms and 1-3 heteroatoms selected from O, N, and $S(O)_{0-2}$, wherein each $R^1$ group is substituted with 0-4 $R^{1a}$;

$R^{1a}$, at each occurrence, is selected from OH substituted with 0-1 $R^{1b}$, SH substituted with 0-1 $R^{1b}$, S, O, halogen, $NH_2$ substituted with 0-2 $R^{1b}$, —CN, $NO_2$, $C_{1-6}$ alkyl substituted with 0-2 $R^{1b}$, $C_{2-6}$ alkenyl substituted with 0-2 $R^{1b}$, $C_{2-6}$ alkynyl substituted with 0-2 $R^{1b}$, aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-3 heteroatoms selected from O, N, and $S(O)_{0-2}$;

$R^{1b}$, at each occurrence, is selected from OH substituted with 0-1 $R^{1c}$, SH substituted with 0-1 $R^{1c}$, S, O, halogen, $NH_2$ substituted with 0-2 $R^{1c}$, —CN, $NO_2$, $C_{1-6}$ alkyl substituted with 0-2 $R^{1c}$, $C_{2-6}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-10}$ cycloalkyl substituted with 0-2 $R^{1c}$, and a 3-8 membered heterocycle substituted with 0-2 $R^{1c}$ and consisting of carbon atoms and 1-3 heteroatoms selected from O, N, and $S(O)_{0-2}$;

$R^{1c}$, at each occurrence, is selected from OH substituted with 0-1 $R^{1d}$, SH substituted with 0-1 $R^{1d}$, S, O, halogen, $NH_2$ substituted with 0-2 $R^{1d}$, —CN, $NO_2$, $C_{1-6}$ alkyl substituted with 0-2 $R^{1d}$, $C_{2-6}$ alkenyl substituted with 0-2 $R^{1d}$, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-10}$ cycloalkyl substituted with 0-2 $R^{1d}$, and a 3-8 membered heterocycle substituted with 0-2 $R^{1d}$ and consisting of carbon atoms and 1-3 heteroatoms selected from O, N, and $S(O)_{0-2}$;

$R^{1d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^2$ is selected from —C≡C—$R^{2a}$, —CH=CH—$R^{2a}$ substituted with 0-2 $R^{2a}$, aryl substituted with 0-3 $R^{2a}$, and 5-10 membered heteroaryl substituted with 0-3 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, S, O, halogen, $NH_2$ substituted with 0-2 $R^{2b}$, —CN, $NO_2$, $C_{1-6}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-10}$ cycloalkyl substituted with 0-2 $R^{2b}$, and a 3-8 membered heterocycle substituted with 0-2 $R^{2b}$ and consisting of carbon atoms and 1-3 heteroatoms selected from O, N, and $S(O)_{0-2}$;

$R^{2b}$, at each occurrence, is selected from OH substituted with 0-1 $R^{2c}$, SH substituted with 0-1 $R^{2c}$, S, O, halogen, $NH_2$ substituted with 0-2 $R^{2c}$, —CN, $NO_2$, $C_{1-6}$ alkyl substituted with 0-2 $R^{2c}$, $C_{2-6}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-10}$ cycloalkyl substituted with 0-2 $R^{2c}$, and a 3-8 membered heterocycle substituted with 0-2 $R^{2c}$ and consisting of carbon atoms and 1-3 heteroatoms selected from O, N, and $S(O)_{0-2}$;

$R^{2c}$, at each occurrence, is selected from OH substituted with 0-1 $R^{2d}$, SH substituted with 0-1 $R^{2d}$, S, O, halogen, $NH_2$ substituted with 0-2 $R^{2d}$, —CN, $NO_2$, $C_{1-6}$ alkyl substituted with 0-2 $R^{2d}$, $C_{2-6}$ alkenyl substituted with 0-2 $R^{2d}$, aryl substituted with 0-2 $R^{2d}$, 5-10 membered heteroaryl substituted with 0-2 $R^{2d}$ and consisting of carbon atoms and 1-4 heteroatoms selected from O, N, and $S(O)_{0-2}$, $C_{3-10}$ cycloalkyl substituted with 0-2 $R^{2d}$, and a 3-8 membered heterocycle substituted with 0-2 $R^{2d}$ and consisting of carbon atoms and 1-3 heteroatoms selected from O, N, and $S(O)_{0-2}$;

$R^{2d}$, at each occurrence, is selected from OH, SH, S, O, halogen, $NH_2$, —CN, $NO_2$, $C_{1-6}$ alkyl, $C_{2-6}$ alkenyl, aryl, $CF_3$, and $OCF_3$;

$R^3$ is selected from halogen and $C_{1-6}$ alkyl substituted with 0-2 $R^{3a}$;

$R^{3a}$, at each occurrence, is selected from OH, O, S, halogen, $C(O)NH_2$, $C(O)NH$—$C_{1-4}$ alkyl, and $C(O)N(C_{1-4}$ alkyl$)_2$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, halogen, and $C_{1-6}$ alkyl substituted with 0-2 $R^{4d}$;

$R^{4d}$, at each occurrence, is selected from OH, O, halogen, $NH_2$, NH—$C_{1-4}$ alkyl, and $N(C_{1-4}$ alkyl$)_2$;

$R^{4b}$, at each occurrence, is selected from H, halogen, and $C_{1-6}$ alkyl substituted with 0-2 $R^{4e}$;

$R^{4e}$, at each occurrence, is selected from OH, O, halogen, $NH_2$, NH—$C_{1-4}$ alkyl, and $N(C_{1-4}$ alkyl$)_2$;

$R^{4c}$, at each occurrence, is selected from H, halogen, and $C_{1-6}$ alkyl substituted with 0-2 $R^{4f}$;

$R^{4f}$, at each occurrence, is selected from OH, O, halogen, $NH_2$, NH—$C_{1-4}$ alkyl, and $N(C_{1-4}$ alkyl$)_2$;

$R^{5a}$, at each occurrence, is selected from H, halogen, $CH_3$, and $CH_2CH_3$;

$R^{5b}$, at each occurrence, is selected from H, halogen, $CH_3$, and $CH_2CH_3$;

$R^{5c}$, at each occurrence, is selected from H, halogen, $CH_3$, and $CH_2CH_3$;

$R^{5d}$, at each occurrence, is selected from H, halogen, $CH_3$, and $CH_2CH_3$; and, $R^{5e}$, at each occurrence, is selected from H, halogen, $CH_3$, and $CH_2CH_3$.

4. A compound of any of the preceding clauses 1-3, wherein the compound is of formula Ia:

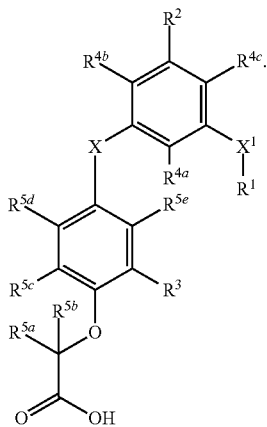

or a pharmaceutically acceptable salt thereof.

5. A compound of clause 1, wherein the compound is of formula II:

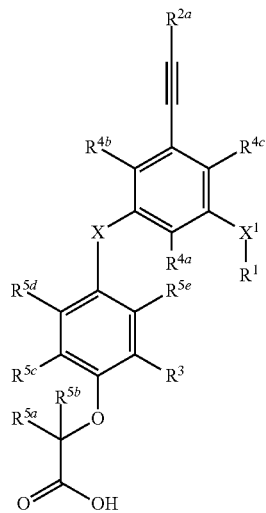

or a pharmaceutically acceptable salt thereof, wherein:

$R^1$ is H, $C_{1-8}$ alkyl, heteroaryl, and $C_{3-10}$ cycloalkyl, wherein each $R^1$ group is substituted with 0-4 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$ and, $C_{3-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, methanesulfonyl, $C_{1-4}$ alkyl substituted with 0-2 $R^{2c}$, $C_{2-4}$ alkenyl substituted with 0-2 $R^{2c}$, aryl substituted with 0-2 $R^{2c}$, heteroaryl substituted with 0-2 $R^{2c}$, $C_{3-6}$ cycloalkyl substituted with 0-2 $R^{2c}$, and a heterocycle substituted with 0-2 $R^{2c}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and heteroaryl substituted with 0-2 $R^{2d}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;

$R^{4b}$, at each occurrence, is selected from H, Cl, F, and $CH_3$;

$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$; and,
$R^{5e}$, at each occurrence, is selected from H, Cl, F, and $CH_3$.

6. A compound of clause 5 wherein:

$R^1$ is H, $C_{1-8}$ alkyl, 5-10 membered heteroaryl consisting of carbon atoms and 1-4 heteroatoms selected from O, N, and $S(O)_{0-2}$, and $C_{3-10}$ cycloalkyl, wherein each $R^1$ group is substituted with 0-4 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, methanesulfonyl, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2c}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$; and,
$R^{5e}$, at each occurrence, is selected from H, Cl, F, and $CH_3$.

7. A compound of clause 5 or 6, wherein:

$R^1$ is H or $C_{1-4}$ alkyl substituted with 1-4 $R^{1a}$;

$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2c}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;

$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$; and,
$R^{5e}$, at each occurrence, is selected from H, Cl, F, and $CH_3$.

8. A compound of clause 5, wherein the compound is of formula IIa:

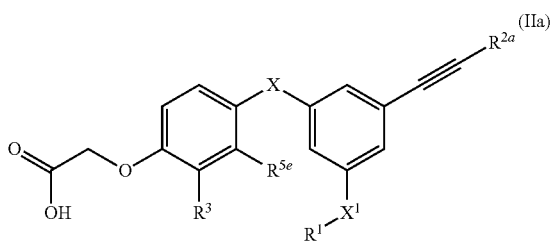

(IIa)

or a pharmaceutically acceptable salt thereof, wherein:

$R^1$ is H, $C_{1-6}$ alkyl, aryl, heteroaryl, and $C_{3-10}$ cycloalkyl, wherein each $R^1$ group is substituted with 0-1 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, heteroaryl substituted with 0-2 $R^{1b}$ and, $C_{5-6}$ cycloalkyl substituted with 0-2 $R^{1b}$, and a heterocycle substituted with 0-2 $R^{1b}$ and;

$R^{1b}$, at each occurrence, is selected from OH, SH, Cl, F, $NH_2$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{5-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{5-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH substituted with 0-1 $R^{2c}$, SH, Cl, F, $NH_2$, —CN, $NO_2$, methanesulfonyl, $C_{1-4}$ alkyl, $C_{2-4}$ alkenyl, aryl, heteroaryl, $C_{5-6}$ cycloalkyl, and a heterocycle;

$R^{2c}$, at each occurrence, is $C_{1-4}$ alkyl;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

9. A compound of clause 8 wherein:

$R^1$ is H, $C_{1-6}$ alkyl, aryl, 5-6 membered heteroaryl consisting of carbon atoms and 1-4 heteroatoms selected from O, N, and $S(O)_{0-2}$, and $C_{3-10}$ cycloalkyl, wherein each $R^1$ group is substituted with 0-1 $R^{1a}$;

$R^{1a}$, at each occurrence, is selected from $C_{1-6}$ alkyl substituted with 0-3 $R^{1b}$; $C_{2-6}$ alkynyl substituted with 0-2 $R^{1b}$; aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, methanesulfonyl, $C_{1-4}$ alkyl substituted with 0-3 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{5-6}$ cycloalkyl substituted with 0-2 $R^{1d}$, and a 5-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O, N, and $S(O)_{0-2}$;

$R^{2b}$, at each occurrence, is selected from OH substituted with 0-1 $R^{2c}$, SH, Cl, F, $NH_2$, —CN, $NO_2$, methanesulfonyl, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$;

$R^{2c}$, at each occurrence, is $C_{1-4}$ alkyl;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

10. A compound of clause 8 or 9 wherein:

$R^1$ is H or $C_{1-4}$ alkyl substituted with 1 $R^{1a}$;

$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{5-6}$ cycloalkyl substituted with 0-2 $R^{1d}$, and a 5-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O, N, and $S(O)_{0-2}$;

$R^{2b}$, at each occurrence, is selected from OH, SH, Cl, F, $NH_2$, —CN, $NO_2$, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$;

$R^3$ is selected from Cl, F, $CH_3$, and $CH_2CH_3$; and, alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$.

11. A compound of clause 8 wherein:

$R^1$ is H, $C_{1-6}$ alkyl, aryl, 5-6 membered heteroaryl consisting of carbon atoms and 1-2 heteroatoms selected from O and N; $C_{3-10}$ cycloalkyl, wherein each $R^1$ group is substituted with 0-1 $R^{1a}$;

$R^{1a}$, at each occurrence, is selected from $C_{1-4}$ alkyl substituted with 0-3 $R^{1b}$; $C_{2-6}$ alkynyl substituted with 0-1 $R^{1b}$ aryl substituted with 0-1 $R^{1b}$, heteroaryl substituted with 0-1 $R^{1b}$, $C_{5-6}$ cycloalkyl substituted with 0-1 $R^{1b}$, and a heterocycle substituted with 0-1 $R^{1b}$;

$R^{1b}$, at each occurrence, is selected from Cl, F, methanesulfonyl, and $C_{1-4}$ alkyl substituted with 0-3 $R^{1c}$, and;

$R^{1c}$, at each occurrence, is selected from Cl, F and a heterocycle;

$R^{2a}$ is selected from $C_{1-6}$ alkyl substituted with 0-2 $R^{2b}$, aryl substituted with 0-2 $R^{2b}$, and heteroaryl substituted with 0-2 $R^{2b}$;

$R^{2b}$, at each occurrence, is selected from OH optionally substituted with $C_{1-4}$ alkyl, Cl, F, methanesulfonyl, aryl, heteroaryl, $C_{5-6}$ cycloalkyl, and a heterocycle;

$R^3$ is selected from Cl, F, $CH_3$, and $CH_2CH_3$.

12. A compound of clause 11 wherein:

$R^1$ is H, $C_{1-6}$ alkyl, aryl, 5-6 membered heteroaryl consisting of carbon atoms and 1-2 heteroatoms selected from O and N; $C_{3-10}$ cycloalkyl, wherein each $R^1$ group is substituted with 0-1 $R^{1a}$;

$R^{1a}$, at each occurrence, is selected from $C_{1-4}$ alkyl substituted with 0-3 $R^{1b}$; $C_{2-6}$ alkynyl substituted with 0-1 $R^{1b}$ aryl substituted with 0-1 $R^{1b}$, 5-6 membered heteroaryl substituted with 0-1 $R^{1b}$ and consisting of carbon atoms and 1-2 heteroatoms selected from O and N, $C_{5-6}$ cycloalkyl substituted with 0-1 $R^{1b}$, and a 5-6 membered heterocycle substituted with 0-1 $R^{1b}$;

$R^{1b}$, at each occurrence, is selected from Cl, F, methanesulfonyl, and $C_{1-4}$ alkyl substituted with 0-3 $R^{1c}$, and;

$R^{1c}$, at each occurrence, is selected from Cl, F and a 5-6 membered heterocycle consisting of carbon atoms and 1-2 heteroatoms selected from O and N;

$R^{2a}$ is selected from $C_{1-6}$ alkyl substituted with 0-2 $R^{2b}$, aryl substituted with 0-2 $R^{2b}$, and 5-6 membered heteroaryl substituted with 0-2 $R^{2b}$ and consisting of carbon atoms and 1-2 heteroatoms selected from O and N;

$R^{2b}$, at each occurrence, is selected from OH optionally substituted with $C_{1-4}$ alkyl, Cl, F, methanesulfonyl, aryl, 5-6 membered heteroaryl consisting of carbon atoms and 1-2 heteroatoms selected from O and N, $C_{5-6}$ cycloalkyl, and a 5-6 membered heterocycle consisting of carbon atoms and 1-2 heteroatoms selected from O and N;

$R^3$ is selected from Cl, F, $CH_3$, and $CH_2CH_3$.

13. A compound of clause 12 wherein $R^1$ is $C_{1-4}$ alkyl substituted with 1 $R^{1a}$ 14. A compound of clause 5, wherein the compound is of formula IIb

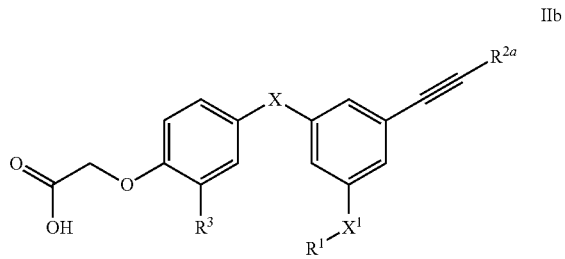

or a pharmaceutically acceptable salt thereof.

15. A compound of clause 14 wherein $R^{2a}$ is selected from aryl substituted with 0-2 $R^{2b}$ and 5-6 membered heteroaryl substituted with 0-2 $R^{2b}$ and consisting of carbon atoms and 1-2 heteroatoms selected from O, N, and $S(O)_{0-2}$.

16. A compound of clause 14, wherein $R^1$ is $C_{1-6}$ alkyl.

17. A compound of clause 14, wherein $R^{2a}$ is $C_{1-4}$ alkyl substituted with a heterocycle.

18. A compound of clause 14, wherein the $R^{2a}$ is $C_{1-4}$ alkyl substituted with morpholinyl.

19. A compound of clause 14, wherein $R^3$ is selected from Cl and $CH_3$.

20. A compound of clause 14, wherein X is selected from S and $SCH_2$.

21. A compound of clause 14, wherein X is S.

22. A compound of clause 14, wherein X is O.

23. A compound of clause 14, wherein X is $SCH_2$.

24. A compound of clause 14, wherein $X^1$ is O.

25. A compound of clause 14, wherein $R^1$ is aryl substituted with 0-1 $R^{1a}$; wherein $R^{1a}$, at each occurrence, is selected from OH, SH, Cl, F, $NH_2$, —CN, $NO_2$, $C_{1-4}$ alkyl.

26. A compound of clause 14, wherein in $R^1$ is $C_{1-6}$ alkyl substituted with $R^{1a}$; and wherein $R^{1a}$ is aryl substituted with 0-1 $R^{1b}$; and wherein $R^{1b}$ is selected from OH, SH, Cl, F, $NH_2$, —CN, $NO_2$, $C_{1-4}$ alkyl.

27. A compound of clause 14, wherein $R^1$ is $C_{1-6}$ alkyl substituted with $R^{1a}$, wherein $R^{1a}$ is heteroaryl substituted with 0-1 $R^{1b}$; and wherein $R^{1b}$ is selected from OH, SH, Cl, F, $NH_2$, —CN, $NO_2$, $C_{1-4}$ alkyl.

28. A compound of clause 14, wherein $R^1$ is $C_{1-6}$ alkyl substituted with $R^{1a}$, wherein $R^{1a}$ is heterocyclyl substituted with 0-1 $R^{1b}$; and wherein $R^{1b}$ is selected from OH, SH, Cl, F, $NH_2$, —CN, $NO_2$, $C_{1-4}$ alkyl.

29. A compound of clause 14, wherein $R^1$ is $C_{1-6}$ alkyl substituted with $R^{1a}$, wherein $R^{1a}$ is $C_{5-6}$ cycloalkyl substituted with 0-2 $R^{1b}$; and wherein $R^{1b}$ is selected from OH, SH, Cl, F, $NH_2$, —CN, $NO_2$, $C_{1-4}$ alkyl.

30. A compound of clause 14, wherein $R^{2a}$ is aryl substituted with $R^{2b}$; wherein $R^{2b}$ is selected from OH, SH, Cl, F, $NH_2$, —CN, $NO_2$, $C_{1-4}$ alkyl.

31. A compound of clause 14, wherein $R^{2a}$ is $C_{1-6}$ alkyl substituted with $R^{2b}$; wherein $R^{2b}$ is selected from aryl substituted with $R^{2c}$; and wherein $R^{2c}$ is selected from OH, SH, Cl, F, $NH_2$, —CN, $NO_2$, $C_{1-4}$ alkyl.

32. A compound of clause 14, wherein $R^{2a}$ is $C_{1-6}$ alkyl substituted with $R^{2b}$; wherein $R^{2b}$ is selected from heteroaryl substituted with $R^{2c}$; and wherein $R^{2c}$ is selected from OH, SH, Cl, F, $NH_2$, —CN, $NO_2$, $C_{1-4}$ alkyl.

33. A compound of clause 1, wherein the compound is selected from:

{2-Chloro-4-[3-(4-chloro-phenylethynyl)-5-(3-piperidin-1-yl-propoxy)-phenylsulfanyl]-phenoxy}-acetic acid;

{2-Methyl-4-[3-(3-morpholin-4-yl-propoxy)-5-phenylethynyl-phenylsulfanyl]-phenoxy}-acetic acid;

{2-Chloro-4-[3-(4-chloro-phenylethynyl)-5-(3-morpholin-4-yl-propoxy)-phenylsulfanyl]-phenoxy}-acetic acid;
{2-Chloro-4-[3-(4-chloro-phenylethynyl)-5-(4-morpholin-4-ylmethyl-benzyloxy)-phenyl-sulfanyl]-phenoxy}-acetic acid;
{2-Chloro-4-[3-(4-chloro-phenylethynyl)-5-(1-methyl-piperidin-4-ylmethoxy)-phenylsulfanyl]-phenoxy}-acetic acid;
{2-Methyl-4-[3-(3-morpholin-4-yl-propoxy)-5-(3-phenyl-prop-1-ynyl)-phenylsulfanyl]-phenoxy}-acetic acid;
{4-[3-(4-Fluoro-benzyloxy)-5-(3-morpholin-4-yl-prop-1-ynyl)-phenylsulfanyl]-2-methyl-phenoxy}-acetic acid;
{4-[3-Cyclohexylmethoxy-5-(3-morpholin-4-yl-prop-1-ynyl)-phenylsulfanyl]-2-methyl-phenoxy}-acetic acid;
{4-[3-Isobutoxy-5-(3-morpholin-4-yl-prop-1-ynyl)-phenylsulfanyl]-2-methyl-phenoxy}-acetic acid;
{4-[3-(4-Chloro-benzyloxy)-5-(3-morpholin-4-yl-prop-1-ynyl)-phenylsulfanyl]-2-methyl-phenoxy}-acetic acid;
{2-Chloro-4-[3-(4-chloro-phenylethynyl)-5-hydroxy-phenylsulfanyl]-phenoxy}-acetic acid;
{4-[3-But-2-ynyloxy-5-(3-morpholin-4-yl-prop-1-ynyl)-phenylsulfanyl]-2-methyl-phenoxy}-acetic acid;
{2-Methyl-4-[3-(2-morpholin-4-yl-ethoxy)-5-phenylethynyl-phenylsulfanyl]-phenoxy}-acetic acid;
{2-Chloro-4-[3-(3-methoxy-prop-1-ynyl)-5-(3-morpholin-4-yl-propoxy)-phenylsulfanyl]-phenoxy}-acetic acid;
{2-Chloro-4-[3-(3-morpholin-4-yl-propoxy)-5-pent-1-ynyl-phenylsulfanyl]-phenoxy}-acetic acid;
{2-Methyl-4-[3-(3-morpholin-4-yl-propoxy)-5-(3-phenyl-prop-1-ynyl)-benzylsulfanyl]-phenoxy}-acetic acid;
{4-[3-(4-Fluoro-benzyloxy)-5-(3-morpholin-4-yl-prop-1 ynyl)-benzylsulfanyl]-2-methyl-phenoxy}-acetic acid; and,
{2-Methyl-4-[3-(3-morpholin-4-yl-ethoxy)-5-(3-phenyl-prop-1-ynyl)-benzylsulfanyl]-phenoxy}-acetic acid;
or a pharmaceutically acceptable salt thereof.

34. A compound of clause 1, wherein the compound is selected from:
{4-[3-Cyclohexylmethoxy-5-(4-methanesulfonyl-phenylethynyl)-phenylsulfanyl]-2-methyl-phenoxy}-acetic acid;
{4-[3-Cyclopentylmethoxy-5-(4-methanesulfonyl-phenylethynyl)-phenylsulfanyl]-2-methyl-phenoxy}-acetic acid;
{4-[3-Isobutoxy-5-(4-methanesulfonyl-phenylethynyl)-phenylsulfanyl]-2-methyl-phenoxy}-acetic acid;
{4-[3-[2-(4-Chloro-phenyl)-ethoxy]-5-(4-methanesulfonyl-phenylethynyl)-phenylsulfanyl]-2-methyl-phenoxy}-acetic acid;
{4-[3-[2-(4-Chloro-phenyl)-ethoxy]-5-(3-morpholin-4-yl-prop-1-ynyl)-phenylsulfanyl]-2-methyl-phenoxy}-acetic acid;
{4-[3-[2-(4-Chloro-phenyl)-ethoxy]-5-(4-hydroxymethyl-phenylethynyl)-phenylsulfanyl]-2-methyl-phenoxy}-acetic acid;
{4-[3-(2-Ethyl-butoxy)-5-phenylethynyl-phenylsulfanyl]-2-methyl-phenoxy}-acetic acid;
[4-(3-Cyclopentyloxy-5-phenylethynyl-phenylsulfanyl)-2-methyl-phenoxy]-acetic acid;
{4-[3-(4-Fluoro-phenylethynyl)-5-(4-methanesulfonyl-benzyloxy)-phenylsulfanyl]-2-methyl-phenoxy}-acetic acid;
[4-(3-Cyclopentylmethoxy-5-phenylethynyl-phenylsulfanyl)-2-methyl-phenoxy]-acetic acid;
{4-[3-(2-Cyclohexyl-ethoxy)-5-phenylethynyl-phenylsulfanyl]-2-methyl-phenoxy}-acetic acid;
{4-[3-(2-Ethyl-butoxy)-5-(3-morpholin-4-yl-prop-1-ynyl)-phenylsulfanyl]-2-methyl-phenoxy}-acetic acid;
{4-[3-Cyclopentyloxy-5-(3-morpholin-4-yl-prop-1-ynyl)-phenylsulfanyl]-2-methyl-phenoxy}-acetic acid;
{4-[3-(2-Cyclohexyl-ethoxy)-5-(3-morpholin-4-yl-prop-1-ynyl)-phenylsulfanyl]-2-methyl-phenoxy}-acetic acid;
{4-[3-Cyclopentylmethoxy-5-(3-morpholin-4-yl-prop-1-ynyl)-phenylsulfanyl]-2-methyl-phenoxy}-acetic acid;
{4-[3-Cyclopentylmethoxy-5-(3-morpholin-4-yl-prop-1-ynyl)-phenylsulfanyl]-2-methyl-phenoxy}-acetic;
{4-[3-Isobutoxy-5-(3-morpholin-4-yl-prop-1-ynyl)-benzylsulfanyl]-2-methyl-phenoxy}-acetic acid;
[4-(3-Isobutoxy-5-phenylethynyl-benzylsulfanyl)-2-methyl-phenoxy]-acetic acid;
{4-[3-Isobutoxy-5-(4-methanesulfonyl-phenylethynyl)-benzylsulfanyl]-2-methyl-phenoxy}-acetic acid;
{4-[3-(4-Methanesulfonyl-phenylethynyl)-5-(5-trifluoromethyl-pyridin-2-yloxy)-phenylsulfanyl]-2-methyl-phenoxy}-acetic acid;
{4-[3-(4-Methanesulfonyl-phenylethynyl)-5-(3-trifluoromethyl-pyridin-2-yloxy)-phenylsulfanyl]-2-methyl-phenoxy}-acetic acid;
{2-Methyl-4-[3-(3-morpholin-4-yl-prop-1-ynyl)-5-(3-trifluoromethyl-pyridin-2-yloxy)-phenylsulfanyl]-phenoxy}-acetic acid;
{2-Methyl-4-[3-(3-morpholin-4-yl-prop-1-ynyl)-5-(5-trifluoromethyl-pyridin-2-yloxy)-phenylsulfanyl]-phenoxy}-acetic acid;
{2-Methyl-4-[3-(3-morpholin-4-yl-prop-1-ynyl)-5-(3-trifluoromethyl-phenoxy)-phenylsulfanyl]-phenoxy}-acetic acid;
{4-[3-(4-Methanesulfonyl-phenylethynyl)-5-(3-trifluoromethyl-phenoxy)-phenylsulfanyl]-2-methyl-phenoxy}-acetic acid; and
{2-Methyl-4-[3-phenylethynyl-5-(5-trifluoromethyl-pyridin-2-yloxy)-phenylsulfanyl]-phenoxy}-acetic acid,
or a pharmaceutically acceptable salt thereof.

35. A compound of clause 1, wherein the compound is of formula III:

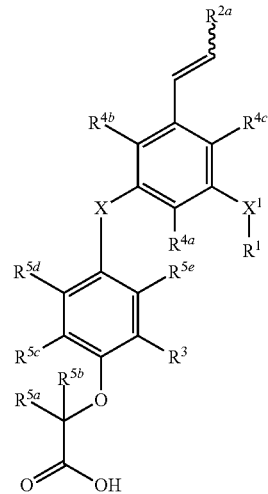

or a pharmaceutically acceptable salt thereof, wherein:
$R^1$ is $C_{1-4}$ alkyl substituted with 1-2 $R^{1a}$;
$R^{1a}$, at each occurrence, is selected from aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$
$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{3-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from aryl substituted with 0-2 $R^{2b}$ and heteroaryl substituted with 0-2 $R^{2b}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, heteroaryl substituted with 0-2 $R^{2c}$, $C_{3-6}$ cycloalkyl substituted with 0-2 $R^{2c}$, and a heterocycle substituted with 0-2 $R^{2c}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and heteroaryl substituted with 0-2 $R^{2d}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

36. A compound of clause 35, wherein:
$R^1$ is $C_{1-4}$ alkyl substituted with 1-2 $R^{1a}$;
$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^{2a}$ is selected from aryl substituted with 0-2 $R^{2b}$ and 5-10 membered heteroaryl substituted with 0-2 $R^{2b}$ and consisting of carbon atoms and 1-4 heteroatoms selected from O, N, and $S(O)_{0-2}$;

$R^{2b}$, at each occurrence, is selected from OH substituted with 0-1 $R^{2c}$, SH substituted with 0-1 $R^{2c}$, Cl, F, $NH_2$ substituted with 0-2 $R^{2c}$, —CN, $NO_2$, $C_{1-4}$ alkyl substituted with 0-2 $R^{2c}$, $C_{2-4}$ alkenyl substituted with 0-2 $R^{2c}$, aryl substituted with 0-2 $R^{2c}$, 5-10 membered heteroaryl substituted with 0-2 $R^{2c}$ and consisting of carbon atoms and 1-4 heteroatoms selected from O, N, and $S(O)_{0-2}$, $C_{3-6}$ cycloalkyl substituted with 0-2 $R^{2c}$, and a 3-6 membered heterocycle substituted with 0-2 $R^{2c}$ and consisting of carbon atoms and 1-2 heteroatoms selected from O, N, and $S(O)_{0-2}$;

$R^{2c}$, at each occurrence, is selected from OH, SH, Cl, F, $NH_2$, —CN, $NO_2$, $C_{1-4}$ alkyl, $C_{2-4}$ alkenyl, aryl substituted with 0-2 $R^{2d}$, and 5-10 membered heteroaryl substituted with 0-2 $R^{2d}$ and consisting of carbon atoms and 1-4 heteroatoms selected from O, N, and $S(O)_{0-2}$;

$R^{2d}$, at each occurrence, is selected from OH, SH, Cl, F, $NH_2$, —CN, $NO_2$, $C_{1-4}$ alkyl, and $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

37. A compound of clause 35, wherein the compound is of formula IIIa

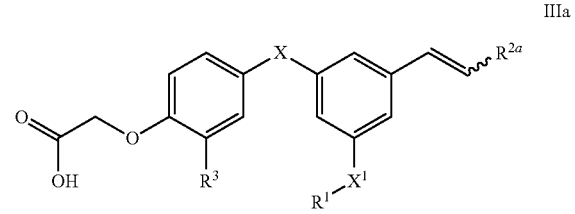

IIIa or a pharmaceutically acceptable salt thereof, wherein:
$R^{1a}$, at each occurrence, is selected from aryl substituted with 0-2 $R^{1b}$, heteroaryl substituted with 0-2 $R^{1b}$, $C_{5-6}$ cycloalkyl substituted with 0-2 $R^{1b}$, and a heterocycle substituted with 0-2 $R^{1b}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{5-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{3-6}$ cycloalkyl substituted with 0-2 $R^{1d}$, and a heterocycle substituted with 0-2 $R^{1d}$;

$R^{2a}$ is selected from aryl substituted with 0-2 $R^{2b}$ and heteroaryl substituted with 0-2 $R^{2b}$ and;

$R^{2b}$, at each occurrence, is selected from OH, SH, Cl, F, $NH_2$, —CN, $NO_2$, $C_{1-4}$ alkyl, $C_{2-4}$ alkenyl, aryl, heteroaryl, $C_{5-6}$ cycloalkyl, and a heterocycle.

38. A compound of clause 37 wherein:

$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{2a}$ is selected from aryl substituted with 0-2 $R^{2b}$ and 5-6 membered heteroaryl substituted with 0-2 $R^{2b}$ and consisting of carbon atoms and 1-2 heteroatoms selected from O, N, and $S(O)_{0-2}$; and, $R^{2b}$, at each occurrence, is selected from OH, SH, Cl, F, $NH_2$, —CN, $NO_2$, $C_{1-4}$ alkyl, $C_{2-4}$ alkenyl, aryl, 5-6 membered heteroaryl consisting of carbon atoms and 1-2 heteroatoms selected from O, N, and $S(O)_{0-2}$, $C_{5-6}$ cycloalkyl, and a 5-6 membered heterocycle and consisting of carbon atoms and 1-2 heteroatoms selected from O, N, and $S(O)_{0-2}$.

39. A compound of clause 4, wherein:

$R^1$ is $C_{1-4}$ alkyl substituted with 1-2 $R^{1a}$;

$R^{1a}$, at each occurrence, is selected from aryl substituted with 0-2 $R^{1b}$, heteroaryl substituted with 0-2 $R^{1b}$, $C_{3-10}$ cycloalkyl substituted with 0-2 $R^{1b}$, and a heterocycle substituted with 0-2 $R^{1b}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, heteroaryl substituted with 0-2 $R^{1c}$, $C_{3-6}$ cycloalkyl substituted with 0-2 $R^{1c}$, and a heterocycle substituted with 0-2 $R^{1c}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, heteroaryl substituted with 0-2 $R^{1d}$, $C_{3-6}$ cycloalkyl substituted with 0-2 $R^{1d}$, and a heterocycle substituted with 0-2 $R^{1d}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^2$ is aryl substituted with 0-3 $R^{2a}$ or heteroaryl substituted with 0-2 $R^{2a}$;

$R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, heteroaryl substituted with 0-2 $R^{2b}$, $C_{3-6}$ cycloalkyl substituted with 0-2 $R^{2b}$, and a heterocycle substituted with 0-2 $R^{2b}$;

$R^{2b}$, at each occurrence, is selected from OH, SH, Cl, F, $NH_2$, —CN, $NO_2$, $C_{1-4}$ alkyl, and, $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

40. A compound of clause 39, wherein:

$R^1$ is $C_{1-4}$ alkyl substituted with 1-2 $R^{1a}$;

$R^{1a}$, at each occurrence, is selected from aryl substituted with 0-2 $R^{1b}$, 5-10 membered heteroaryl substituted with 0-2 $R^{1b}$ and consisting of carbon atoms and 1-4 heteroatoms selected from O, N, and $S(O)_{0-2}$, $C_{3-10}$ cycloalkyl substituted with 0-2 $R^{1b}$, and a 3-8 membered heterocycle substituted with 0-2 $R^{1b}$ and consisting of carbon atoms and 1-2 heteroatoms selected from O, N, and $S(O)_{0-2}$;

$R^{1b}$, at each occurrence, is selected from OH substituted with 0-1 $R^{1c}$, SH substituted with 0-1 $R^{1c}$, Cl, F, $NH_2$ substituted with 0-2 $R^{1c}$, —CN, $NO_2$, $C_{1-4}$ alkyl substituted with 0-2 $R^{1c}$, $C_{2-4}$ alkenyl substituted with 0-2 $R^{1i}$, aryl substituted with 0-2 $R^{1c}$, 5-10 membered heteroaryl substituted with 0-2 $R^{1c}$ and consisting of carbon atoms and 1-4 heteroatoms selected from O, N, and $S(O)_{0-2}$, $C_{3-6}$ cycloalkyl substituted with 0-2 $R^{1c}$, and a 3-6 membered heterocycle substituted with 0-2 $R^{1c}$ and consisting of carbon atoms and 1-2 heteroatoms selected from O, N, and $S(O)_{0-2}$;

$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-10 membered heteroaryl substituted with 0-2 $R^{1d}$ and consisting of carbon atoms and 1-4 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;

$R^{1d}$, at each occurrence, is selected from OH, SH, Cl, F, $NH_2$, —CN, $NO_2$, $C_{1-4}$ alkyl, and $C_{2-4}$ alkenyl;

$R^2$ is aryl substituted with 0-3 $R^{2a}$ or 5-10 membered heteroaryl substituted with 0-2 $R^{2a}$ and consisting of carbon atoms and 1-4 heteroatoms selected from O, N, and $S(O)_{0-2}$;

$R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, 5-10 membered heteroaryl substituted with 0-2 $R^{2b}$ and consisting of carbon atoms and 1-4 heteroatoms selected from O, N, and $S(O)_{0-2}$, $C_{3-6}$ cycloalkyl substituted with 0-2 $R^{2b}$, and a 3-6 membered heterocycle substituted with 0-2 $R^{2b}$ and consisting of carbon atoms and 1-2 heteroatoms selected from O, N, and $S(O)_{0-2}$;

$R^{2b}$, at each occurrence, is selected from OH, SH, Cl, F, $NH_2$, —CN, $NO_2$, $C_{1-4}$ alkyl, and, $C_{2-4}$ alkenyl;

$R^3$ is selected from Cl, F, $CH_3$, and $CH_2CH_3$;

alternatively, $R^3$ and $R^{5e}$ combine to form a 5, 6, or 7 membered ring consisting of carbon atoms and 0-2 heteroatoms selected from O, N, and $S(O)_{0-2}$ and there are 0-2 ring double bonds in the bridging portion formed by $R^3$ and $R^{5e}$;

$R^{4a}$, at each occurrence, is selected from H, Cl, F, and $CH_3$;
$R^{4b}$, at each occurrence, is selected from H, Cl, F, and $CH_3$;
$R^{4c}$, at each occurrence, is selected from H, Cl, F, and $CH_3$;
$R^{5a}$, at each occurrence, is selected from H, Cl, F, and $CH_3$;
$R^{5b}$, at each occurrence, is selected from H, Cl, F, and $CH_3$;
$R^{5c}$, at each occurrence, is selected from H, Cl, F, and $CH_3$;
$R^{5d}$, at each occurrence, is selected from H, Cl, F, and $CH_3$;
and,
$R^{5e}$, at each occurrence, is selected from H, Cl, F, and $CH_3$.

41. A compound of clause 40, wherein the compound is of formula Ib:

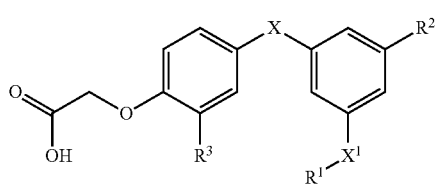

Ib or a pharmaceutically acceptable salt thereof, wherein:
$R^1$ is $C_{1-4}$ alkyl substituted with 1 $R^{1a}$;
$R^{1a}$, at each occurrence, is selected from aryl substituted with 0-2 $R^{1b}$, 5-6 membered heteroaryl substituted with 0-2 $R^{1b}$ and consisting of carbon atoms and 1-2 heteroatoms selected from O, N, and $S(O)_{0-2}$, $C_{5-6}$ cycloalkyl substituted with 0-2 $R^{1b}$, and a 5-6 membered heterocycle substituted with 0-2 $R^{1b}$ and consisting of carbon atoms and 1-2 heteroatoms selected from O, N, and $S(O)_{0-2}$;
$R^{1b}$, at each occurrence, is selected from OH, SH, Cl, F, $NH_2$, —CN, $NO_2$, $C_{1-4}$ alkyl substituted with 0-2 $R^{1c}$, $C_{2-4}$ alkenyl substituted with 0-2 $R^{1c}$, aryl substituted with 0-2 $R^{1c}$, 5-6 membered heteroaryl substituted with 0-2 $R^{1c}$ and consisting of carbon atoms and 1-2 heteroatoms selected from O, N, and $S(O)_{0-2}$, $C_{5-6}$ cycloalkyl substituted with 0-2 $R^{1c}$, and a 5-6 membered heterocycle substituted with 0-2 $R^{1c}$ and consisting of carbon atoms and 1-2 heteroatoms selected from O, N, and $S(O)_{0-2}$;
$R^{1c}$, at each occurrence, is selected from OH, SH, Cl, F, $NH_2$, —CN, $NO_2$, $C_{1-4}$ alkyl, and $C_{2-4}$ alkenyl, aryl substituted with 0-2 $R^{1d}$, 5-6 membered heteroaryl substituted with 0-2 $R^{1d}$ and consisting of carbon atoms and 1-2 heteroatoms selected from O, N, and $S(O)_{0-2}$, $C_{3-6}$ cycloalkyl substituted with 0-2 $R^{1d}$, and a 3-6 membered heterocycle substituted with 0-2 $R^{1d}$ and consisting of carbon atoms and 1-2 heteroatoms selected from O, N, and $S(O)_{0-2}$;
$R^2$ is aryl substituted with 0-2 $R^{2a}$ or 5-6 membered heteroaryl substituted with 0-2 $R^{2a}$ and consisting of carbon atoms and 1-2 heteroatoms selected from O, N, and $S(O)_{0-2}$; and,
$R^{2a}$, at each occurrence, is selected from OH substituted with 0-1 $R^{2b}$, SH substituted with 0-1 $R^{2b}$, Cl, F, $NH_2$ substituted with 0-2 $R^{2b}$, —CN, $NO_2$, $C_{1-4}$ alkyl substituted with 0-2 $R^{2b}$, $C_{2-6}$ alkenyl substituted with 0-2 $R^{2b}$, aryl substituted with 0-2 $R^{2b}$, 5b-6 membered heteroaryl substituted with 0-2 $R^{2b}$ and consisting of carbon atoms and 1-2 heteroatoms selected from O, N, and $S(O)_{0-2}$, $C_{5-6}$ cycloalkyl substituted with 0-2 $R^{2b}$, and a 5-6 membered heterocycle substituted with 0-2 $R^{2b}$ and consisting of carbon atoms and 1-2 heteroatoms selected from O, N, and $S(O)_{0-2}$.

42. A pharmaceutical composition, comprising: a pharmaceutically acceptable carrier and a compound of one of clauses 1-41 or a pharmaceutically acceptable salt.

43. A pharmaceutical composition for treating type 2 diabetes, comprising a compound according to any of the clauses 1-41 together with one or more pharmaceutically acceptable carriers or excipients.

44. A pharmaceutical composition for treating dyslipidemia, syndrome X (including the metabolic syndrome, e.g., hypertension, impaired glucose tolerance (IGT), insulin resistance, hypertrigyceridaemia, and obesity), cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke), hyperglycemia, hyperlipidemia, hypercholesterolemia, and hyperinsulinemia, comprising a compound according to any of the clauses 1-41 together with one or more pharmaceutically acceptable carriers or excipients.

45. A pharmaceutical composition for treating dyslipidemia comprising a compound according to any of the clauses 1-41 together with one or more pharmaceutically acceptable carriers or excipients.

46. A pharmaceutical composition for treating syndrome X (including the metabolic syndrome, e.g., hypertension, impaired glucose tolerance (IGT), insulin resistance, hypertrigyceridaemia, and obesity), comprising a compound according to any of the clauses 1-41 together with one or more pharmaceutically acceptable carriers or excipients.

47. A pharmaceutical composition for treating cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke), comprising a compound according to any of the clauses 1-41 together with one or more pharmaceutically acceptable carriers or excipients 48. A pharmaceutical composition for treating hyperglycemia comprising a compound according to any of the clauses 1-41 together with one or more pharmaceutically acceptable carriers or excipients.

49. A pharmaceutical composition for treating hyperlipidemia comprising a compound according to any of the clauses 1-41 together with one or more pharmaceutically acceptable carriers or excipients.

50. A pharmaceutical composition for treating hypercholesterolemia comprising a compound according to any of the clauses 1-41 together with one or more pharmaceutically acceptable carriers or excipients 51. A pharmaceutical composition for treating hyperinsulinemia comprising a compound according to any of the clauses 1-41 together with one or more pharmaceutically acceptable carriers or excipients 52. A pharmaceutical composition according to any one of the clauses 42-51 for oral, nasal, transdermal, pulmonal or parenteral administration.

53. Use of a compound according to any one of the clauses 1-41 as a pharmaceutical composition.

54. Use of a compound according to any one of the clauses 1-41 for the preparation of a pharmaceutical composition for treating type 2 diabetes.

55. Use of a compound according to any one of the clauses 1-41 for the preparation of a pharmaceutical composition for treating dyslipidemia, syndrome X (including the metabolic syndrome, e.g., hypertension, impaired glucose tolerance (IGT), insulin resistance, hypertrigyceridaemia, and obesity), cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke), hyperglycemia, hyperlipidemia, hypercholesterolemia, and hyperinsulinemia.

56. Use of a compound according to any one of the clauses 1-41 for the preparation of a pharmaceutical composition for treating dyslipidemia.

57. Use of a compound according to any one of the clauses 1-41 for the preparation of a pharmaceutical composition for treating syndrome X (including the metabolic syndrome, e.g., hypertension, impaired glucose tolerance (IGT), insulin resistance, hypertrigyceridaemia, and obesity).

58. Use of a compound according to any one of the clauses 1-41 for the preparation of a pharmaceutical composition for treating cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke).

59. Use of a compound according to any one of the clauses 1-41 for the preparation of a pharmaceutical composition for treating hyperglycemia.

60. Use of a compound according to any one of the clauses 1-41 for the preparation of a pharmaceutical composition for treating hyperlipidemia.

61. Use of a compound according to any one of the clauses 1-41 for the preparation of a pharmaceutical composition for treating hypercholesterolemia.

62. Use of a compound according to any one of the clauses 1-41 for the preparation of a pharmaceutical composition for treating hyperinsulinemia 63. A method of treating type 2 diabetes, comprising: administering a therapeutically effective amount of a compound of one of clauses 1-41 or a pharmaceutically acceptable salt.

64. A method of treating a disease, comprising: administering a therapeutically effective amount of a compound of one of clauses 1-41 or a pharmaceutically acceptable salt, wherein the disease is selected from dyslipidemia, syndrome X (including the metabolic syndrome, e.g., hypertension, impaired glucose tolerance (IGT), insulin resistance, hypertrigyceridaemia, and obesity), cardiovascular diseases (e.g., atherosclerosis and related diseases, including mortality reduction, coronary artery diseases, coronary heart diseases, heart attack, myocardial ischemia, myocardial infarct, coronary infarct, transient ischemic attack (TIA), and stroke), hyperglycemia, hyperlipidemia, hypercholesterolemia, and hyperinsulinemia.

65. A compound of one of clauses 1-41 or a pharmaceutically acceptable salt thereof, wherein the compound has a solubility in water of at least 0.1 mg/L as determined at 25° C. and pH 7.0.

66. The compound of clause 65, wherein the compound has a solubility in water of at least 0.5 mg/L.

67. The compound of clause 66, wherein the compound has a solubility in water of at least 1 mg/L.

68. The compound of clause 67, wherein the compound has a solubility in water of at least 2 mg/L.

69. The compound of clause 68, wherein the compound has a solubility in water of at least 10 mg/L.

70. The compound of clause 69, wherein the compound has a solubility in water of at least 50 mg/L.

71. The compound of clause 70, wherein the compound has a solubility in water of at least 200 mg/L.

72. A compound of one of clauses 1-41 or a pharmaceutically acceptable salt thereof, wherein the compound has an $IC_{50}$ value of less than 1 μm as determined by the PPAR transient transactivation assay.

73. The compound of clause 72, wherein the compound has an $IC_{50}$ value of less than 500 nm.

74. The compound of clause 73, wherein the compound has an $IC_{50}$ value of less than 100 nm.

75. The compound of clause 74, wherein the compound has an $IC_{50}$ value of less than 50 nm.

76. The compound of clause 75, wherein the compound has an $IC_{50}$ value of less than 25 nm.

77. The compound of clause 76, wherein the compound has an $IC_{50}$ value of less than 10 nm.

78. The compound of clause 77, wherein the compound has an $IC_{50}$ value of less than 5 nm.

79. A compound of one of clauses 1-41, wherein the compound has a molecular weight of less than 750 g/mol.

80. The compound of clause 79, wherein the compound has a molecular weight of less than 600 g/mol.

81. The compound of clause 80, wherein the compound has a molecular weight of less than 550 g/mol.

82. The compound of clause 81, wherein the compound has a molecular weight of less than 500 g/mol.

83. The compound of clause 82, wherein the compound has a molecular weight of less than 400 g/mol.

84. A compound of one of clauses 1-41, wherein the compound is ionized at a pH of from 5.5-9.

85. The compound of clause 84, wherein the compound has only one ionized carboxylic acid group at a pH of from 6-8.

86. The compound of clause 85, wherein the compound has only one ionized carboxylic acid group at a pH of from 6.5-7.5.

87. The compound of clause 86, wherein the compound has only one ionized carboxylic acid group at pH 7.4.

88. A compound of one of clauses 1-41, wherein the compound is a zwitter-ion with one ionized amine group and one ionized carboxylic acid group at a pH of from 5.5-9.

89. The compound of clause 88, wherein the compound is a zwitter-ion with one ionized amine group and one ionized carboxylic acid group at a pH of from 6-8.

90. The compound of clause 89, wherein the compound is a zwitter-ion with one ionized amine group and one ionized carboxylic acid group at a pH of from 6.5-7.5

91. The compound of clause 90, wherein the compound is a zwitter-ion with one ionized amine group and one ionized carboxylic acid group at pH 7.4.

What is claimed is:

1. A method of treating a renal disease selected from the group consisting of glomerulonephritis, glomerulosclerosis, nephrotic syndrome, and hypertensive nephrosclerosis comprising: administering to a human subject {4-[3-isobutoxy-5-(3-morpholin-4-yl-prop-1-ynyl)-phenylsulfanyl]-2-methylphenoxy}-acetic acid or a pharmaceutically acceptable salt thereof.

2. A method of treating a renal disease selected from the group consisting of glomerulonephritis, glomerulosclerosis, nephrotic syndrome, and hypertensive nephrosclerosis comprising: administering to a human subject {4-[3-isobutoxy-5-(3-morpholin-4-yl-prop-1-ynyl)-benzylsulfanyl]-2-methylphenoxy}-acetic acid or a pharmaceutically acceptable salt thereof.

3. A method of treating a cardiovascular disease selected from the group consisting of atherosclerosis, mortality reduction, coronary artery disease, coronary heart diseases, heart attack, myocardial ischemia, myocardial infarct, coronary infarct, transient ischemic attack (TIA), and stroke comprising: administering to a human subject {4-[3-isobutoxy-5-(3-morpholin-4-yl-prop-1-ynyl)-phenylsulfanyl]-2-methylphenoxy}-acetic acid or a pharmaceutically acceptable salt thereof.

4. A method of treating a cardiovascular disease selected from the group consisting of atherosclerosis, mortality reduction, coronary artery disease, coronary heart diseases, heart attack, myocardial ischemia, myocardial infarct, coronary infarct, transient ischemic attack (TIA), and stroke comprising: administering to a human subject {4-[3-isobutoxy-5-(3-morpholin-4-yl-prop-1-ynyl)-benzylsulfanyl]-2-methyl-phenoxy}-acetic acid or a pharmaceutically acceptable salt thereof.

\* \* \* \* \*

UNITED STATES PATENT AND TRADEMARK OFFICE
CERTIFICATE OF CORRECTION

| | |
|---|---|
| PATENT NO. | : 8,426,473 B2 |
| APPLICATION NO. | : 13/466191 |
| DATED | : April 23, 2013 |
| INVENTOR(S) | : Soren Ebdrup |

It is certified that error appears in the above-identified patent and that said Letters Patent is hereby corrected as shown below:

On Title page, item (73), in "Assignee", in column 1, line 1, Delete "Pharnaceuticals," and insert -- Pharmaceuticals, --, therefor.

On Title page, item (56), in "Foreign Patent Documents", in column 2, line 3, After "WO 01/25226" Delete "8/1997" and insert -- 04/2001 --, therefor.

Title page 2, under "OTHER PUBLICATIONS", in column 2, line 20, Delete "Homestasis" and insert -- Homeostasis --, therefor.

Title page 2, under "OTHER PUBLICATIONS", in column 2, line 27, Delete "cheolesterol" and insert -- cholesterol --, therefor.

Signed and Sealed this
Second Day of July, 2013

Teresa Stanek Rea
*Acting Director of the United States Patent and Trademark Office*